US010233197B2

(12) United States Patent
Yu

(10) Patent No.: US 10,233,197 B2
(45) Date of Patent: *Mar. 19, 2019

(54) HIGH PENETRATION PRODRUG COMPOSITIONS OF ANTIMICROBIALS AND ANTIMICROBIAL-RELATED COMPOUNDS

(75) Inventor: Chongxi Yu, Plainfield, IL (US)

(73) Assignee: TECHFIELDS PHARMA CO., LTD., Suzhou, Jiangsu (CN)

(*) Notice: Subject to any disclaimer, the term of this patent is extended or adjusted under 35 U.S.C. 154(b) by 0 days.

This patent is subject to a terminal disclaimer.

(21) Appl. No.: 13/550,361

(22) Filed: Jul. 16, 2012

(65) Prior Publication Data
US 2013/0018029 A1    Jan. 17, 2013

Related U.S. Application Data

(60) Division of application No. 12/482,373, filed on Jun. 10, 2009, now abandoned, which is a continuation-in-part of application No. PCT/IB2006/054724, filed on Dec. 10, 2006.

(51) Int. Cl.
| | |
|---|---|
| *C07D 501/16* | (2006.01) |
| *C07D 501/18* | (2006.01) |
| *A61K 31/545* | (2006.01) |
| *A61P 31/04* | (2006.01) |
| *C07D 499/00* | (2006.01) |

(52) U.S. Cl.
CPC ............ *C07D 499/00* (2013.01); *A61P 31/04* (2018.01)

(58) Field of Classification Search
CPC .. C07D 501/16; C07D 501/18; A61K 31/545; A61P 31/04
USPC .................................................. 514/200, 209
See application file for complete search history.

(56) References Cited

U.S. PATENT DOCUMENTS

| | | | |
|---|---|---|---|
| 2,593,852 A | 4/1952 | Cooper | |
| 2,694,031 A | 11/1954 | Frederiksen et al. | |
| 2,694,061 A | 11/1954 | Frederiksen et al. | |
| 2,694,063 A | 11/1954 | Frederiksen | |
| 3,957,764 A | 5/1976 | Lund | |
| 4,081,546 A | 3/1978 | Ferres | |
| 4,150,157 A | 4/1979 | Ferres | |
| 4,215,120 A | 7/1980 | Ferres | |
| 4,285,960 A * | 8/1981 | Ferres .................. | C07D 499/00 514/195 |
| 4,311,706 A | 1/1982 | Bodor et al. | |
| 4,428,935 A | 1/1984 | Myers | |
| 4,496,574 A | 12/1985 | Muto et al. | |
| 4,690,920 A | 9/1987 | Kanno et al. | |
| 4,699,920 A | 10/1987 | Skuballa et al. | |
| 4,746,509 A | 5/1988 | Haggiage et al. | |
| 5,321,020 A | 6/1994 | Jasys | |
| 5,629,019 A * | 5/1997 | Lee et al. .................. | 424/489 |
| 5,929,086 A | 7/1999 | Watts et al. | |
| 6,011,049 A | 1/2000 | Whitcomb | |
| 6,191,143 B1 | 2/2001 | Watts et al. | |
| 7,052,715 B2 | 5/2006 | Fishman | |
| 7,256,210 B2 | 8/2007 | Man et al. | |
| 2004/0229920 A1 | 11/2004 | Garvey et al. | |
| 2005/0277634 A1 | 12/2005 | Janott et al. | |
| 2006/0058219 A1 | 3/2006 | Miller | |
| 2006/0222692 A1* | 10/2006 | Lane .............................. | 424/449 |

FOREIGN PATENT DOCUMENTS

| | | |
|---|---|---|
| AU | 457864 | 1/1975 |
| DE | 858699 | 12/1952 |
| EP | 0262744 B1 | 3/1994 |
| ES | 409580 A1 | 12/1975 |
| FR | 2132447 B1 | 4/1976 |
| GB | 759603 | 10/1956 |
| GB | 768347 | 2/1957 |
| GB | 1454726 | 11/1976 |
| GB | 1470154 | 4/1977 |
| GB | 2040926 | 9/1980 |

(Continued)

OTHER PUBLICATIONS

Weingarten, C. "Randomized, comparative study of oral cefadroxil and cephalexin in lower respiratory infections in adults" Journal of Antimicrobial Chemotherapy, 1982, vol. 10, suppl. B., pp. 109-113.*
Kumar et al. "Comparative Study of Cephalexin Hydrochloride and Cephalexin Monohydrate in the Treatment of Skin and Soft Tissue Infection" Antimicrobial Agents and Chemotherapy, Jun. 1988, pp. 882-885.*
Woodhead et al. "Guidelines for the management of adult lower respiratory tarct infections" Eur Respir J, 2005, vol. 26, pp. 1138-1180.*
Cannon, J. G., "Analog Design," Burger's Medicinal Chemistry and Drug Discovery, Ch. 19, 5th Ed., vol. 1: Principles and Practice, Wiley-Interscience, 1995, pp. 783-802.
Godfrey, A. J., et al., "Penetration of Beta-Lactams Through Pseudomonas Aeruginosa Porin Channels," Antimicrobial Agents & Chemotherapy 31(8):1216-1221 (1987).

(Continued)

*Primary Examiner* — Kendra D Carter
(74) *Attorney, Agent, or Firm* — Finnegan, Henderson, Farabow, Garrett & Dunner, L.L.P.

(57) ABSTRACT

The invention provides compositions of novel high penetration compositions (HPC) or high penetration prodrugs (HPP) of antimicrobials and antimicrobial-related compounds, which are capable of crossing biological barriers with high penetration efficiency. The HPPs are capable of being converted to parent active drugs or drug metabolites after crossing the biological barrier and thus can render treatments for the conditions that the parent drugs or metabolites can. Additionally, the HPPs are capable of reaching areas that parent drugs may not be able to access or to render a sufficient concentration at the target areas and therefore render novel treatments. The HPPs can be administered to a subject through various administration routes, e.g., locally delivered to an action site of a condition with a high concentration or systematically administered to a biological subject and enter the general circulation with a faster rate.

13 Claims, 6 Drawing Sheets

(56) References Cited

FOREIGN PATENT DOCUMENTS

| | | |
|---|---|---|
| GB | 2157284 A | 10/1985 |
| JP | 54-019993 | 2/1979 |
| JP | 02254425 A2 | 10/1990 |
| JP | B-03-015622 | 3/1991 |
| WO | WO 93/07902 | 4/1993 |
| WO | WO 1997/42954 A1 | 11/1997 |
| WO | WO 2000/047589 A1 | 8/2000 |
| WO | WO 02/056916 A2 | 7/2002 |
| WO | WO 2003/022270 A1 | 3/2003 |
| WO | WO 2004/009538 A1 | 1/2004 |
| WO | WO 2007/117687 A2 | 10/2007 |
| WO | WO 2008/007171 A1 | 1/2008 |
| WO | WO 2008/010025 A1 | 1/2008 |
| WO | WO 2008/012602 A1 | 1/2008 |
| WO | WO 2008/012603 A1 | 1/2008 |
| WO | WO 2008/021605 A1 | 1/2008 |
| WO | WO 2008/017903 A1 | 2/2008 |
| WO | WO 2008/020270 A1 | 2/2008 |
| WO | WO 2008/026776 | 3/2008 |
| WO | WO 2008/029199 A1 | 3/2008 |
| WO | WO 2008/029200 A1 | 3/2008 |
| WO | WO 2008/044095 A1 | 4/2008 |
| WO | WO 2008/056207 A1 | 5/2008 |
| WO | WO 2008/072032 A1 | 6/2008 |
| WO | WO 2008/093173 A1 | 8/2008 |
| WO | WO 2008/149181 A1 | 12/2008 |

OTHER PUBLICATIONS

Andrews, J. M., "Determination of Minimum Inhibitory Concentrations," Journal of Antimicrobial Chemotherapy 48, suppl. S1: 5-16 (2001).

Arora, P., et al., "Design Development, Physiochemical, and In Vitro and In Vivo Evaluation of Transdermal Patches Containing Diclofenac Diethylammonium Salt," J. Pham. Sci. 91:2076-2089 (2002).

Bagyalakshmi, J., et al., "Pharmacodynamics of Ampicillin Sodium Transdermal Patches in an In Vitro Infection Model," Indian Journal of Pharmaceutical Sciences 68(4):540-541 (2006).

Barnden, R. L., et al., "Some Preparative Uses of Benzylpenicillinic Ethoxyformic Anhydride," J. Chem. Soc. pp. 3733-3739 (1953).

Berge, S.M., et al., "Pharmaceutical Salts," J. Pharm. Sci. 66(1):1-19 (1977).

Farkas, E. R., et al., "Synthesis of Penicillin Sulfoxides and Their Esters," Magyar Kemiai Folyoirat 84(6):257-260 (1978).

Giraldez, A., et al., "Kinetics of DAN-523. Modification of an Antibiotic from the Group of Semisynthetic Penicillins of Selective Exrcretion Through Milk," Archives of Pharmacol. Toxicol. 2(3):311-314 (1976).

Hatanaka, T., et al., "Ion Pair Skin Transport of a Zwitterionic Drug, Cephalexin," Journal of Controlled Release 66(1):63-71 (2000).

Ilankumaran, P., et al., "Prop-2-ynyl as a Protective Group for Carboxylic Acids: A Mild Method for the Highly Selective Deprotection of Prop-2-ynyl Esters Using Tetrathiomolybdate," Chem. Commun. 1957-1957 (1996).

Jansen, A. B. A., et al., "Some Novel Penicillin Derivatives," J. Chem Soc. 2127-2132 (1965).

Johnson, D. A., "Carboxy Derivatives of Benzylpenicillin," J. Am. Chem. Soc. 75:3636-3637 (1953).

Korean Intellectual Property Office, International Preliminary Report on Patentability for PCT/IB2006/054724, dated Jun. 10, 2009.

Lazaro, A., et al., "Pharmacokinetic Evaluation and Mammary Excretion of Tamethicillin in the Healthy Goat," Am J Vet Res 40(8):1173-1176 (1979).

Mandell, G. L., et al., Ch. 46: Antimicrobial Agents, Goodman Gilman's the Pharmacological Basis of Therapeutics. 8th ed., McGraw-Hill, Inc. 1991, vol. II, pp. 1065-1097.

Milosovich, S., et al., "Testosteronyl-4-Dimethylaminobutyrate-HCI: A Prodrug with Improved Skin Penetration Rate," J. Pharm. Sci. 82(2):227-228 (1993).

Tanaka, R., et al., " Structure-Activity Relationships of Penem Antibiotics: Crystallographic Structures and Implications for Their Antimicrobial Activities," Bioorganic & Medicinal Chemistry 5(7):1389-1399 (1997).

Ziv, G., et al., "Concentrations of Methicillin in Blood, Normal Milk and Mastitic Milk of Cows After Intramuscular Injection of Methicillin and Tamethicillin," J. Vet. Pharmacol. Therap. 6(1):41-48 (1983).

Database Caplus [Online] Chemical Abstracts Service, Columbus, OH, US; "Effect of Penicillinase on Certain Salts and Esters of Penicillin," retrieved from STN database accession No. 61:33936 (2001).

Ohlenschlaeger, K., et al., "Scleroderma Treated with the Diethylamine-Ethylester Hydriodide Salt of Penicillin G.," Dermatologica 134:129-134 (1967).

Sheridan, R. P., "The Most Common Chemical Replacements in Drug-Like Compounds," J. Chem. Inf. Comput. Sci. 42:103-108 (2002).

Battaglino, R., et al., "Fluoxetine Treatment Increases Trabecular Bone Formation in Mice (Fluoxetine Affects Bone Mass)," J. Cell Biochem. 100(6):1387-1394 (2007).

Carrico, D., et al., "In Vitro and In Vivo Antimalarial of Peptidomimetic Protein Farnesyltransferase Inhibitors with Improved Membrane Permeability," Bioorg. Med. Chem. 12(24):6517-6526 (2004).

Drachman, D.B., et al., "Cycloxygenase 2 Inhibition Protects Motor Neurons and Prolongs Survival in a Transgenic Mouse Model of ALS," Annals of Neurology 52:771-778 (2002).

Erlanson-Albertsson, C., et al., "Enterostatin—A Peptide Regulating Fat Intake," Obes. Res. 5(4):360-372 (1997).

Ginaldi, L., et al., "Osteoporosis, Inflammation and Ageing," Immunity & Ageing 2:14 (2005).

Hovgaard, L., et al., "Drug Delivery Studies in Caco-2 Monolayers. Synthesis, Hydrolysis, and Transport of O-Cyclopropane Carboxylic Acid Ester Prodrugs of Various B-Blocking Agents," Pharm. Res. 12(3):387-392 (1995).

Hovgaard, L., et al., "Permeation Studies on O-Cyclopropanoyl Ester Prodrugs of B-Blockers in Caco-2 Cell Monolayers," Proceed. Intern: Symp. Control. Rel. Bioact. Mater. 20:238-239 (1993).

Pan, D.S., et al., "Inhibitory Effect of Progesterone on Inflammatory Factors after Experimental Traumatic Brain Injury," Biomed. Environ. Sci. 20(5):432-438 (2007).

Raisz, L., "Pathogenesis of Osteoporosis: Concepts, Conflicts, and Prospects," J. Clin. Invest. 115(12):3318-3325 (2005).

Roof, R.L., et al., "Gender Differences in Acute CNS Trauma and Stroke: Neuroprotective Effects of Estrogen and Progesterone," J. Neurotrauma 17(5):367-388 (2000).

Scott, I. L., "Keystone Symposia: Inflammation and Cancer, Breckenridge, CO, USA, Feb. 27-Mar. 3, 2005," Technical Reports 10(13)1-17.

Sorhede, M., et al., "Enterostatin: A Gut-Brain Peptide Regulating Fat Intake in Rat," J. Physiol. 87(4):273-275 (1993).

St. Rose, S. G., et al., "Effect of penethamate hydriodide treatment on bacteriological cure, somatic cell count and milk production of cows and quarters with chronic subclinical *Streptococcus uberis* or *Streptococcus dysgalactiae* infection," J. Dairy Res. 70:387-394 (2003).

Tozkoparan, B., et al.,"6-Benzylidenethiazolo[3,2-b]-1,24-Triazole-5(6H)-Ones Sybstituted with Ibprofen: Synthesis, Characterization and Evaluation of Anti-Inflammatory Activity," Eur. J. Med. Chem. 35(7-8):743-750 (2000).

Wheeler, W. J., et al., "Orally Active Esters of Cephalosporin Antibiotics. 3. Synthesis and Biological Properties of Aminoacyloxymethyl Esters of 7-[D-(-)-Mandelamido]-3-[[(1-methyl-[H-tetrazol-5-yl)thio]methyl]-3-cephem-4-carboxylic Acid," J. Med. Chem. 22(6):657-661 (1979).

Wright, D.W., et al., "ProTECT: A Randomized Clinical Trial of Progesterone for Acute Traumatic Brain Injury," Ann. Emerg. Med. 49(4):391-402 (2007).

Xiao, G., et al., "Improved Outcomes from the Administration of Progesterone for Patients with Acute Severe ttraumatic bbrain iinjury: A Randomized Controlled Trial," Crit. Care 12:R61 (2008).

Yang, S., et al., "Specificity of RGS10A as a Key Component in the RANKL Signaling Mechanism for Osteoclast Differentiation," J. Cell Sci. 120:3362-3371 (2007).

(56) References Cited

OTHER PUBLICATIONS

Cheng, H., et al., "Cyclooxygenase-2 inhibitor blocks expression of mediators of renal injury in a model of diabetes and hypertension," *Kidney International*, 62:929-939 (2002).
Chinese Intellectual Property Office, International Preliminary Report on Patentability and Written Opinion for PCT/CN2010/073743, dated Dec. 12, 2011 (7 pages).
Chinese Intellectual Property Office, International Search Report for PCT/CN2010/073743, dated Sep. 23, 2010 (6 pages).
Database Caplus [Online] Chemical Abstracts Service. Columbus, OH, US; "Effect of Penicillinase on Certain Salts and Esters of Penicillin," retrieved from STN database RN 91507-51-6, entered Nov. 16, 1984 (1 page).
European Patent Office, Extended European Search Report for EP 06832186.8, dated Aug. 6, 2010 (7 pages).
European Patent Office, Extended European Search Report for EP 10785754.2, dated Feb. 19, 2014 (5 pages).
European Patent Office, Extended European Search Report for EP 13161970.2, dated Oct. 1, 2013 (8 pages).
Jensen, K.A., et al., "Investigation of Penicillin Preparations and Dosage Schedules," *Ugeskrift for Laeger*, 112:1043-1046 (1950).
Jensen, K.A., et al., "Studies of Penicillin Preparations and Dosage," *Ugeskrift for Laeger*, 112(31):1075-1080 (1950).
Korean Intellectual Property Office, International Search Report for PCT/IB2006/054724, dated Aug. 22, 2007 (3 pages).
Raether, W., et al., "Comparison of Two Different Techniques in Primary Mycological Screening: Standard Serial Dilution Tests and Microtitration Test," *Mykosen*, 27(1):14-28 (1984).
Petri, W. A., Ch. 45: Antimicrobial Agents: Penicillins, Cephalosporins, and other ß-Lactam Antibiotics, Goodman Gilman's the Pharmacological Basis of Therapeutics. 10th ed., McGraw-Hill Professional, 2001, pp. 1189-1218.
Gould, P. L., "Salt selection for basic drugs", *International Journal of Pharmaceutics*, 33 (1986), p. 201-217.

\* cited by examiner

Figure 1a1
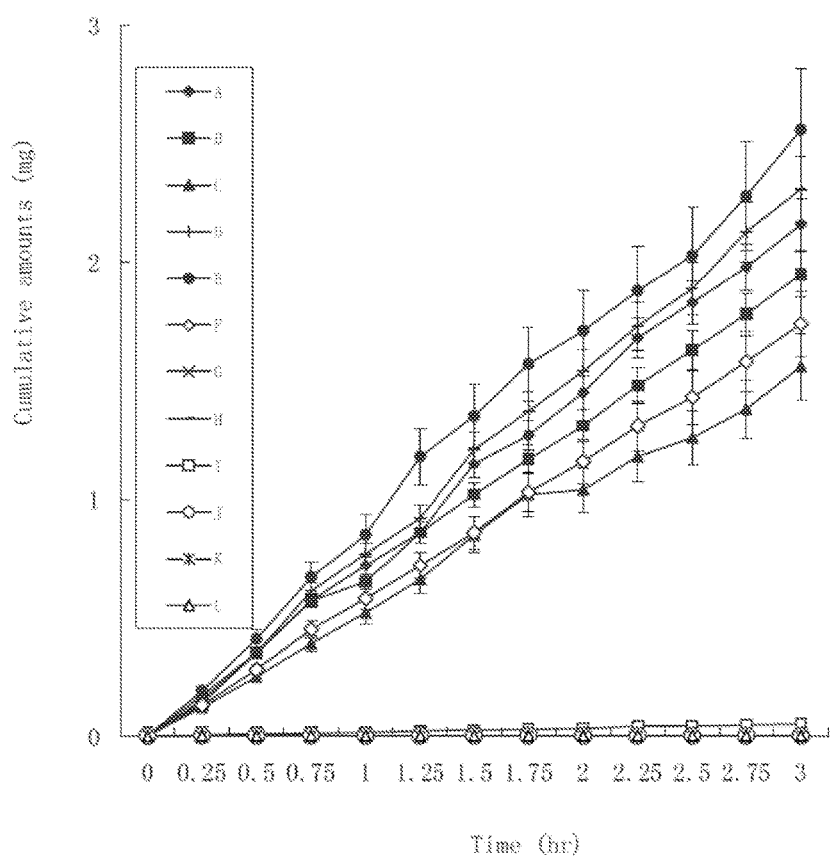

Figure 1a2
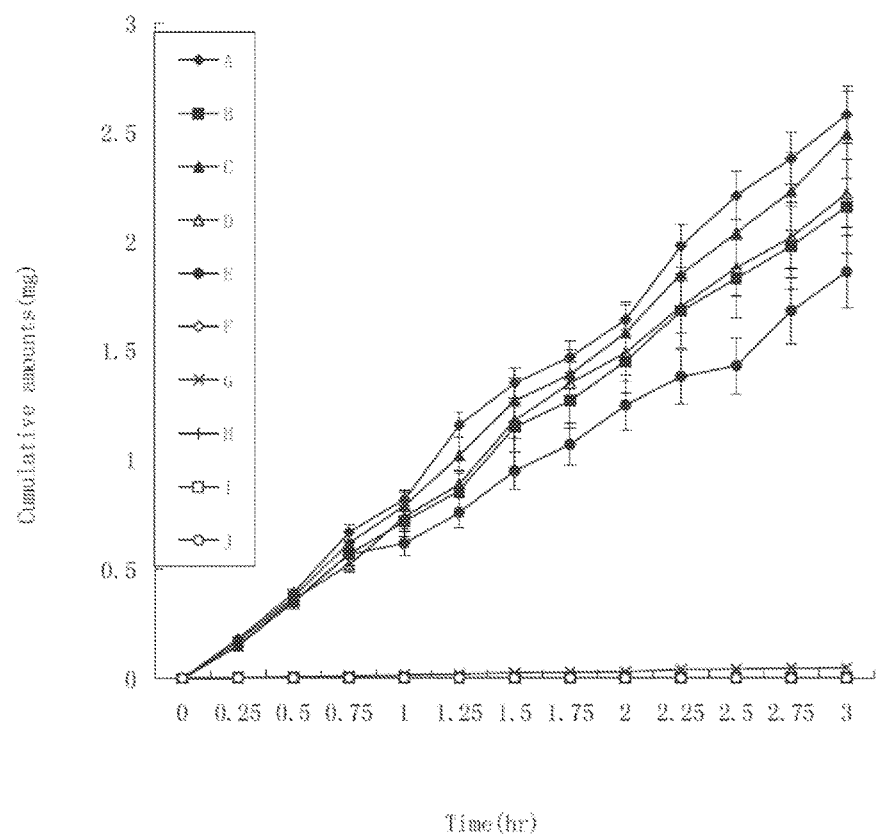

Figure 1a3
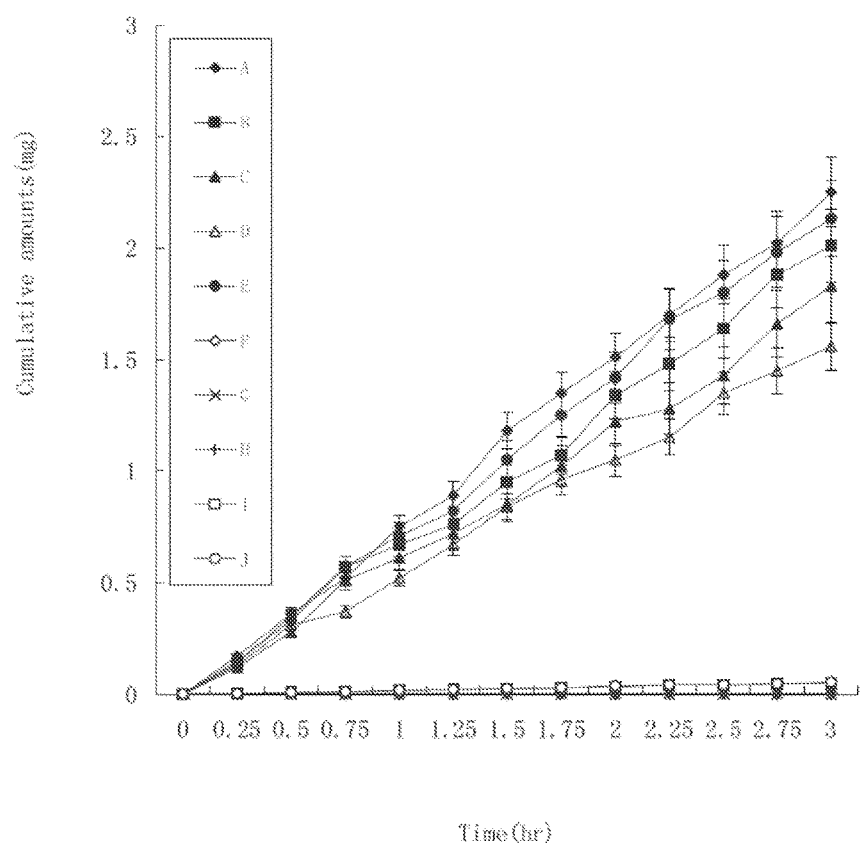

Figure 1a4
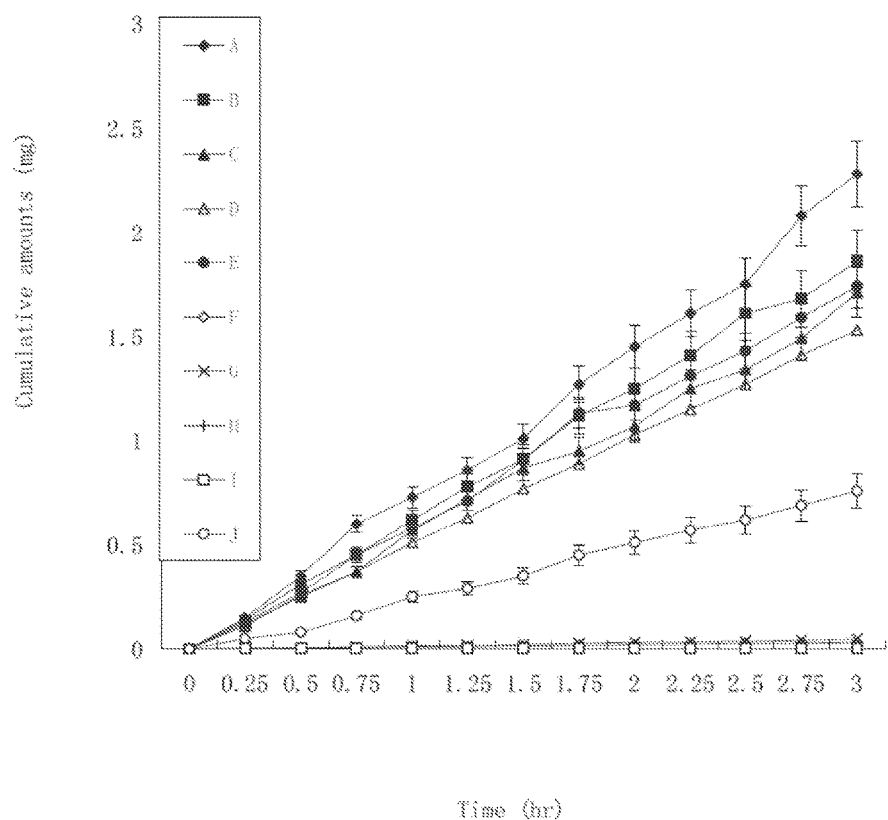

HIGH PENETRATION PRODRUG COMPOSITIONS OF ANTIMICROBIALS AND ANTIMICROBIAL-RELATED COMPOUNDS

CROSS-REFERENCE TO RELATED APPLICATIONS

The present application is a divisional application of U.S. application Ser. No. 12/482,373, filed Jun. 10, 2009, which is a continuation-in-part application of International Application PCT/IB2006/054724, filed Dec. 10, 2006 and published Jun. 19, 2008 with International Publication Number WO2008/072032, both of which are incorporated herein by reference in their entirety.

FIELD OF THE INVENTION

This invention relates to the field of pharmaceutical compositions capable of penetrating one or more biological barriers and methods of using the pharmaceutical compositions for preventing, diagnosing and/or treating condition or disease in human and animals that are treatable by antimicrobials and antimicrobial-related compounds. The invention also relates to methods of using the pharmaceutical compositions for screening new drug candidates and methods of using the pharmaceutical compositions for diagnosing a condition in a biological subject.

BACKGROUND OF THE INVENTION

Antimicrobials are substances that kill or inhibit the growth of microorganisms such as bacteria, fungi, or protozoans, as well as destroying viruses. The main classes of antimicrobials include, for example, antibiotics that treat bacterial-related conditions, antivirals that treat viral-related conditions, antifungals that treat fungal-related conditions and antiprotozoals that treat protozoans-related conditions.

Beta-lactam antibiotics are a class of antibiotics that comprise a four-member ring beta-lactam nucleus in their molecular structures. Over a hundred thousand of beta-lactam antibiotics have been prepared by partial or total chemical synthesis (L. A. Mitscher, et al., Antibiotic and Antimicrobial Drugs, in D. F. Smith, Ed., Handbook of Stereoisomers: Therapeutic Drugs, Boca Raton, Fla., CRC Press, 1989; R. B. Morin and M. Gorman Eds., Chemistry and Biology of Beta-lactam Antibiotics, Volumes 1-3, New York, Academic Press, 1982; and A. L. Demain and N. A. Solomon, Eds., Antibiotics Containing the Beta-lactam Structure, Vols, 1 and 2, Handbook of experimental Pharmacology, vol. 67, New York, Springer, 1983). Examples of beta-lactam antibiotics include penicillin derivatives, cephalospotrins, monobactams, carbapenems, beta-lactamase inhibitors, sulfonamide and quinolones.

Along with the extensive use of antimicrobials, drug resistance becomes a common and serious problem as the pathogens mutate over time. Therefore, it is an urgent and challenging task to develop new antimicrobials.

A wide variety of antimicrobial are administered through Intravenous infusion, intramuscular injection, subcutaneous, buccal, oral, and rectal routes. Oral administration has disadvantage of poor absorption of the antibiotics from GI tract. Intravenous, subcutaneous and intramuscular routes are not only painful, but also require administration by trained individuals and may incur other risks such as needle injury, infection, and other trauma.

One alternative method of drug administration is topical delivery. Topical drug delivery has several advantages. This method avoids inactivation of a drug caused by first pass metabolism in the liver and gastro-intestinal tract. It also provides local delivery of appropriate concentrations of a drug to the intended site of action without systemic exposure. Fishman (Fishman; Robert, U.S. Pat. No. 7,052,715) indicated that an additional problem associated with oral medications, is that the concentration levels which must be achieved in the bloodstream must be significant in order to effectively treat distal areas of pain, inflammation, or infection. These levels are often much higher than would be necessary if the drugs were accurately delivered to the particular site of pain or injury. For most of antimicrobials, topical administration cannot deliver an effective therapeutic level.

Therefore, a need exists in the art for novel compositions that are capable of being delivered efficiently and effectively to the action site of a condition (e.g., a disease) to prevent, reduce or treat conditions as well as minimize adverse side effects.

SUMMARY OF THE INVENTION

One aspect of the invention is directed to a high penetration prodrug (HPP) or high penetration composition (HPC) comprising a functional unit covalently linked to a transportational unit through a linker. The terms "HPP" and "HPC" are used alone or together herein and are interchangeable unless specifically noted.

In certain embodiments, a functional unit of a HPP or HPC comprises a moiety of a parent drug, wherein the efficient and effective delivery of the parent drug to a biological subject and/or transportation of the parent drug across one or more biological barriers are/is desired.

In certain embodiments, a functional unit may be hydrophilic, lipophilic, or amphiphilic (i.e., both hydrophilic and lipophilic). For example, the lipophilic nature of a function unit may be inherent or achieved by converting the hydrophilic moieties of a functional unit to lipophilic moieties. In certain embodiments, a carboxyl group, amino group, guanidine group or other hydrophilic group of a functional unit is protected with an alkyl, aryl, or heteroaryl ester or amide group to make the HPP or HPC more lipophilic.

In certain embodiments, a functional unit of a HPP or HPC comprises a moiety of an antimicrobial or an antimicrobial-related compound. An antimicrobial is a substance that kills or inhibits the growth of microorganisms such as bacteria, fungi, or protozoans, as well as destroying viruses. An antimicrobial-related compound is a compound comprising an antimicrobial structure, an antimicrobial metabolite, or an agent that can be metabolized into an antimicrobial or antimicrobial metabolite after a HPP or HPC penetrates one or more biological barriers. An antimicrobial-related compound further includes a compound that is an analog or mimic of an antimicrobial or an antimicrobial metabolite, or an agent that can be metabolized into an analogue or mimic of an antimicrobial or an antimicrobial metabolite, after a HPP or HPC penetrates one or more biological barriers.

Examples of antimicrobials include, for example, antibiotics that treat bacterial-related conditions, antivirals that treat viral-related conditions, antifungals that treat fungal-related conditions and antiprotozoals that treat protozoans-related conditions.

Examples of antibiotics include, without limitation, beta-lactam antibiotics, sulfonamides and quinolones. Examples of beta-lactam antibiotics include, but are not limited to, penicillin derivatives, cephalosporins, penems, monobactams, carbapenems, beta-lactamase inhibitors and combinations thereof. Examples of penicillin derivatives include, but are not limited to, aminopenicillins (e.g. amoxicillin, ampicillin, and epicillin); carboxypenicillins (e.g. carbenicillin, ticarcillin, and temocillin); ureidopenicillins (e.g. azlocillin, piperacillin and mezlocillin); mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxicillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenem, .doripenem, ertapenem, .imipenem, .meropenem, .and panipenem. Examples of beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam (2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0]heptane-2-carboxylic acid). Other examples of antibiotics include, without limitation, [(N-benzyloxycarbonylamino)methyl]-phosphonic acid mono-(4-nitrophenyl) ester sodium salt, [(N-benzyloxycarbonylamino)methyl]-phosphonic acid mono-(3-pyridinyl) ester sodium salt, sulfanilamide (4-aminobenzenesulfonamide), sulfasalazine (6-oxo-3-(2-[4-(N-pyridin-2-ylsulfamoyl)phenyl]hydrazono)cyclohexa-1,4-dienecarboxylic acid), 1-cyclopropyl-6-fluoro-4-oxo-7-piperazin-1-yl-quinoline-3-carboxylic acid, nalidixic acid (1-ethyl-7-methyl-4-oxo-[1,8]naphthyridine-3-carboxylic acid), Examples of sulfonamides include, without limitation, sulfaisodimidine, sulfanilamide, sulfadiazine, sulfisoxazole, sulfamethoxazole, sulfadimethoxine, sulfamethoxypyridazine, sulfacetamide, sulfadoxine, acetazolamide, bumetanide, chlorthalidone, clopamide, furosemide, hydrochlorothiazide, indapamide, mefruside, metolazone, xipamide, dichlorphenamide, dorzolamide, acetazolamide, ethoxzolamide, sultiame, zonisamide, mafenide, celecoxib, darunavir, probenecid, sulfasalazine, and sumatriptan.

Examples of quinolones include, without limitation, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, garenoxacin, ecinofloxacin, delafloxacin and nalidixic acid.

Examples of antivirals include, without limitation, rifampicin, zanamivir and oseltamivir.

Examples of antifungals include, without limitation, polyene antifungals (e.g. natamycin, rimocidin, filipin, nystatin, amphotericin B, candicin), imidazole antifungals (e.g. miconazole, ketoconazloe, clotrimazole, econazole, bifonazole, butoconazole, fenticonazole, isoconazole, oxiconazole, sertaconazole, sulconazole, and tioconazole), triazoles antifungals (e.g. fluconazole, itraconazole, isavuconazole, ravuconazole, posaconazole, voriconazole, and terconazole), thiazole antifungals (e.g. abafungin), allyamines (e.g. terbinafine, amorolfine, naftifine and butenafine), echinocandins (e.g. anidulafungin, caspofungin and micafungin) and other antifungals such as benzoic acid, ciclopirox, tolnaftate, undecylenic acid, flucytosine, griseofulvin, haloprogin.

Examples of antiprotozoals include, without limitation, elornithine, furazolidone, melarsoprol, metronidazole, ornidazole, paromomycin sulfate, pentamidine, pyrimethamine, and tinidazole.

In certain embodiments, a transportational unit of a HPP or HPC comprises a protonatable amine group that is capable of facilitating or enhancing the transportation or crossing of the HPP or HPC through one or more biological barriers. In certain embodiments, the protonatable amine group is substantially protonated at the pH of the biological barriers through which a HPP or HPC penetrates. In certain embodiments, the amine group can be reversibly protonated or deprotonated.

In certain embodiments, a linker covalently links the functional unit to the transportational unit of a HPP and comprises a bond that is capable of being cleaved after the HPP penetrates across one or more biological barriers. The cleavable bond comprises, for example, a covalent bond, an ether, a thioether, an amide, an ester, a thioester, a carbonate, a carbamate, a phosphate or an oxime bond.

In certain embodiments, a HPP or HPC of an antimicrobial or antimicrobial-related compound comprises one or two primary, secondary or tertiary amine groups that exist in the protonated form at physiological pH. In certain embodiments, the HPP or HPC comprises one primary, secondary or tertiary amine group that exists in the protonated form at physiological pH.

Another aspect of the invention relates to a pharmaceutical composition comprising at least one HPP or HPC of an antimicrobial or antimicrobial-related compound and a pharmaceutically acceptable carrier.

Another aspect of the invention relates to a method for penetrating a biological barrier using a HPP or HPC of an antimicrobial or antimicrobial-related compound.

Another aspect of the invention relates to a method for diagnosing the onset, development, or remission of a condition in a biological subject by using a HPP or HPC of an antimicrobial or antimicrobial-related compound. In certain embodiments, the HPP (or HPC) or the functional unit thereof is detectable. In certain embodiments, the HPP or the functional unit of the HPP is inherently detectable, labeled with, or conjugated to, a detectable marker.

Another aspect of the invention relates to a method for screening functional units, linkers, or transportational units for desired characteristics.

Another aspect of the invention relates to a method for preventing, ameliorating, or treating a condition in a biological subject by administering to the subject a composition in accordance with the invention. In certain embodiments, the method relates to treating a condition in a subject treatable by antimicrobials or antimicrobial-related compounds by administering to the subject a therapeutically effective amount of a HPP of an antimicrobial or antimicrobial-related compound, or a pharmaceutical composition thereof. In certain embodiments, conditions treatable by the method include, without limitation, pain, injuries and microorganism related conditions. Microoranism related conditions are conditions that are caused by microorganisms such as bacteria, fungi, protozoans and viruses. For example, conditions caused by bacteria (bacteria-related conditions), conditions caused by protozoa (protozoa-related conditions), conditions caused by fungi (fungi-related conditions) and conditions caused by virus (virus-related conditions). Bacteria-related conditions include, for example, infections (e.g. infection condition in an organ such as liver, lung, stomach, brain, kidney, heart, ear, eye, nose, mouth, tongue, colon, pancreas, gallbladder, duodenum, rectum stomach, colonrectum, intestine, vein, respiratory system, vascular, anorectum and pruritus ani, respiratory infections, upper respiratory tract infections, urinary tract infections, nosocomial infections, *pseudomonas* infection, Coagulase-positive staphylococcal infections (e.g. skin infection, toxinoses, acute infective endocarditis, septicemia, necrotizing pneumonia), infections of implanted prostheses, opportunistic infections with septicemia and pneumonia), plague (e.g. bubonic plague and pneumonic plague), anthrax (e.g. cutaneous anthrax, pulmonary anthrax and gastrointestinal antrax), lyme diseases, brucellosis, whooping cough, acute enteritis, psittacosis, nongonococcal urethritis, trachoma, inclusion conjunctivitis of the newborn, lymphogranuloma venereum, pseudomembranous colitis, gas gangrene, food poisoning, anaerobic cellulitis, diphtheria, diarrhea, meningitis in infants, hemorrhagic colitis, hemolytic-uremic syndrome, tularemia, pneumonia, bronchitis, peptic ulcer, legionnaire's disease, Pontiac fever, leptospirosis, listeriosis, leprosy, turberculosis, *mycoplasma* pneumonia, gonorrhea, ophthalmia neonatorum, septic arthritis, meningococcal disease, waterhouse-friderichsen syndrome, Rocky mountain spotted fever, typhoid fever type *salmonellosis, salmonellosis* with gastroenteritis and enterocolitis, bacillary dysentery, shigellosis, cystitis, meningitis, septicemia, endometritis, otitis media, sinusitis, syphilis, necrotizing fasciitis, streptococcal pharyngitis, scarlet fever, rheumatic fever, impetigo, erysipelas, puerperal fever, and cholera. Protozoa related conditions include, for example, malaria, sleeping sickness, and toxoplasmosis. Fungi related conditions include, for example, aspergillosis, blastomycosis, ringworm, candidiasis, coccidioidomycois, cryptococcosis, histoplasmosis, paracoccidiomycosis, sporotrichosis, and zygomycosis. Virus related conditions include, for example, influenza, yellow fever and AIDS.

In certain embodiments, a pharmaceutical composition of a HPP or HPC is administrated to a biological subject via various routes including, but not limited to, oral, enteral, buccal, nasal, topical, rectal, vaginal, aerosol, transmucosal, epidermal, transdermal, dermal, ophthalmic, pulmonary, subcutaneous, and/or parenteral routes. In certain preferred embodiments, a pharmaceutical composition of a HPP or HPC is administered orally, transdermally, topically, subcutaneously and/or parenterally.

In accordance with the advantages of the invention, without intending to be limited by any particular mechanism, a therapeutically effective amount of a HPP or HPC can be administered locally to a site of condition with a less dosage at a higher concentration. The advantages of the invention also include, for example, avoidance of systematic administration, reduction of adverse effects (e.g., pain of injection, gastrointestinal/renal effects, and other side effect), and possible novel treatments due to high local concentration of a HPP, HPC or active agent. The advantages further include, for example, systematic administration of a HPP or HPC to a biological subject to achieve faster and more efficient bioavailability, penetration of biological barriers (e.g., the blood brain barrier and the blood milk barrier) which have been difficult to cross, and new indications as a result of passing through biological barriers.

BRIEF DESCRIPTION OF THE FIGURES

FIG. 1*a*1: Cumulative amounts of 6-phenoxyacetacetamidopenicillanic acid 2-diethylaminoethyl ester hydrochloride (A), allylmercaptomethylpenicillinic acid 2-dimethylaminoethyl ester hydrochloride (B), 6-(2,6-dimethoxybenzamido) penicillinic acid 2-dipropylaminoethyl ester hydrochloride (C), 6-(5-methyl-3-phenyl-2-isoxazoline-4-carboxamido) penicillinic acid 4-piperidineethyl ester hydrochloride (D), 6-[3-(o-chlorophenyl)-5-methyl-4-isoxazolecarboxamido] penicillinic acid 3-piperidine ethyl ester hydrochloride (E), 6-[3-(2,6-dichlorophenyl)-5-methyl-4-isoxazolecarboxamido]penicillinic acid 1-piperidineethyl ester hydrochloride (F), penicillin V (G), penicillin O (H), methicillin (I), oxacillin (J), cloxacillin (K), and dicloxacillin (L), crossing isolated human skin tissue in Franz cells (n=5). In each case, the vehicle was pH 7.4 phosphate buffer (0.2 M).

FIG. 1*a*2: Cumulative amounts of 6-[D(-)-α-aminophenylacetamidopenicillinic acid ethyl ester hydrochloride (A), D-α-[(imidazolidin-2-on-1-yl)carbonylamino]benzylpenicillin 2-pyrrolidinemethyl ester hydrochloride (B), 6R-[2-[3-(methylsulfonyl)-2-oxo-1-imidazolidinecarboxamido]-2-phenylacetamido]penicillinic acid 1-pyrrolidineethyl ester hydrochloride (C), 6-DH-α-(4-ethyl-2,3-dioxo-1-piperazinylcarbonylamino)-α-phenylacetamidopenicillinic acid 2-diethylaminoethyl ester hydrochloride (D), 7-(2-thienylacetamido)cephalosporanic acid 2-diethylaminoethyl ester hydrochloride (E), ampicillin (F), azlocillin (G), mezlocillin (H), piperacillion (I), and cephalothin (J), crossing isolated human skin tissue in Franz cells (n=5). In each case, the vehicle was pH 7.4 phosphate buffer (0.2 M).

FIG. 1*a*3: Cumulative amounts of 7-[(hydroxyphenylacetyl)amino]-3-[[(1-methyl-1H-tetrazol-5-yl)thio] methyl]-8-oxo-5-thia-1-azabicyclo[4.2.0]oct-2-ene-2-carboxylic acid 2-diethylaminoethyl ester hydrochloride (A), 3-[[(aminocarbonyl)oxy]methyl]-7-[[2-furanyl(methoxyimino)acetyl]amino]-8-oxo-5-thia-1-azabicyclo[4.2.0]oct-2-ene-2-carboxylic acid 2-diethylaminoethyl ester hydrochloride (B), 3-[[(aminocarbonyl)oxy]methyl]-7-methoxy-8-oxo-7-[(2-thienylacetyl)amino]-5-thia-1-azabicyclo [4.2.0]oct-2-ene-2-carboxylic acid 2-diethylaminoethyl ester hydrochloride (C), 7-[[[2-(acetylaminomethyl)phenyl] acetyl]amino]-3-[[[1-(ethoxylcarbonylmethyl)-1H-tetrazol-5-yl]thio]methyl]-8-oxo-5-thia-1-azabicyclo[4.2.0]oct-2-ene-2-carboxylic acid 2-diethylaminoethyl ester hydrochloride (D), 7-[(acetylaminophenylacetyl)amino]-3-chloro-8-oxo-5-thia-1-azabicyclo[4.2.0]oct-2-ene-2-carboxylic acid 2-diethylaminoethyl ester hydrochloride (E), cefamandole (F), cefuroxime (G), cefoxitin (H), ceforanide (I), and cefaclor (J), crossing isolated human skin tissue in Franz cells (n=5). In each case, the vehicle was pH 7.4 phosphate buffer (0.2 M).

FIG. 1*a*4: Cumulative amounts of 3-[(acetyloxy)methyl]-7-[[(2-acetylamino-4-thiazolyl)(methoxyimino)acetyl] amino]-8-oxo-5-thia-1-azabicyclo[4.2.0]oct-2-ene-2-carboxylic acid 2-diethylaminoethyl ester hydrochloride (A), 7-[[(2-acetylamino-4-thiazolyl)(methoxyimino)acetyl] amino]-8-oxo-5-thia-1-azabicyclo[4.2.0]oct-2-ene-2-carboxylic acid 2-diethylaminoethyl ester hydrochloride (B), 7-[[[[(4-ethyl-2,3-dioxo-1-piperazinyl)carbonyl]amino](4-acetoxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride (C), 7-[2-(2-acetylamino-4-thiazolyl)-2-((Z)-methoxyimino)acetamido]-3-(methoxymethyl)-8-oxo-5-thia-1-azabicyclo[4.2.0]oct-2-ene-2-carboxylic acid 2-diethylaminoethyl ester hydrochloride (D), 7-[2-(2-acetylamino-4-thiazolyl)-2-((Z)-ethoxycarbonylmethoxy)imino]acetamido]-3-(vinyl)-8-oxo-5-thia-1-azabicyclo[4.2.0]oct-2-ene-2-carboxylic acid 2-diethylaminoethyl ester hydrochloride (E), cefotaxime (F), ceftizoxime (G), cefoperazone (H), cefpodoxime proxetil (I), and cefixime (J), crossing isolated human skin tissue in Franz cells (n=5). In each case, the vehicle was pH 7.4 phosphate buffer (0.2 M).

DETAILED DESCRIPTION OF THE INVENTION

Figure 1B:
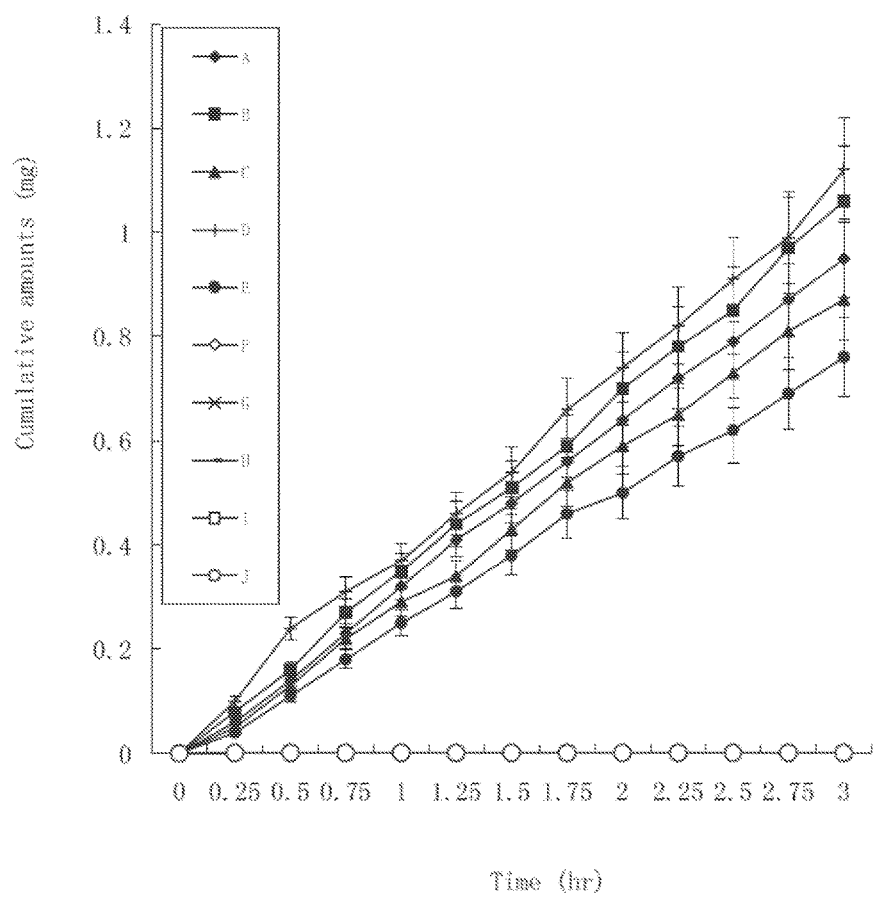
FIG. 1b: Cumulative amounts of [2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt (tazobactam, F), [2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide 1-piperidineethyl ester.HCl salt (tazobactam-PEE, A), 2S,5R)-3,3-dimethyl-7-oxo-4-thia-1-azabicyclo[3.2.0]heptane-2-carboxylic acid 4,4-dioxide sodium (sulbactam, G), 2S,5R)-3,3-dimethyl-7-oxo-4-thia-1-azabicyclo[3.2.0]heptane-2-carboxylic acid 4,4-dioxide N,N-diethylaminoethyl ester.HCl salt (sulbactam-DEE, B), (2R,5R,Z)-3-(2-hydroxyethylidene)-7-oxo-4-oxa-1-aza-bicyclo[3.2.0]heptane-2-carboxylic acid (clavulanic acid, H), (2R,5R,Z)-3-(2-hydroxyethylidene)-7-oxo-4-oxa-1-aza-bicyclo[3.2.0]heptane-2-carboxylic acid 4-piperidineethyl ester.HCl salt (clavulanic acid-PEE, C), [(N-benzyloxycarbonylamino)methyl]-phosphonic acid mono-(4-nitrophenyl) ester sodium salt (I), [(N-benzyloxycarbonylamino)methyl]-phosphonic acid (4-nitrophenyl)(N,N-diethylaminomethyl) ester.HCl salt (D), [(N-benzyloxycarbonylamino)methyl]-phosphonic acid mono-(3-pyridinyl) ester sodium salt (J), and [(N-benzyloxycarbonylamino)methyl]-phosphonic acid (3-pyridinyl)(1-piperidinyl) ester.HCl salt (E), crossing isolated human skin tissue in Franz cells (n=5). In each case, the vehicle was pH 7.4 phosphate buffer (0.2 M).

I. Structures of High Penetration Prodrug (HPP) or High Penetration Composition (HPC)

One aspect of the invention is directed to a high penetration prodrug (HPP) or a high penetration composition (HPC). The term "high penetration prodrug" or "HPP" or "high penetration composition" or "HPC" as used herein refers to a composition comprising a functional unit covalently linked to a transportational unit through a linker.

A functional unit of a HPP or HPC which comprises a moiety of a parent drug has the properties of: 1) the delivery of the parent drug or the HPP/HPC into a biological subject and/or the transportation of the parent drug across a biological barrier are/is desired, 2) the HPP/HPC is capable of penetrating or crossing a biological barrier, and 3) the HPP/HPC is capable of being cleaved so as to turn the moiety of a parent drug into the parent drug or a metabolite of the parent drug.

In certain embodiments, a functional unit may be hydrophilic, lipophilic, or amphiphilic (hydrophilic and lipophilic). The lipophilic moiety of the functional unit may be inherent or achieved by converting one or more hydrophilic moieties of the functional unit to lipophilic moieties. For example, a lipophilic moiety of a functional unit is produced by converting one or more hydrophilic groups of the functional unit to lipophilic groups via organic synthesis. Examples of hydrophilic groups include, without limitation, carboxylic, hydroxyl, thiol, amine, phosphate/phosphonate, guanidine and carbonyl groups. Lipophilic moieties produced via the modification of these hydrophilic groups include, without limitation, ethers, thioethers, esters, thioesters, carbonates, carbamates, amides, phosphates and oximes. In certain embodiments, a functional unit is lipophilicized by acetylation. In certain embodiments, a functional unit is lipophilicized by esterification.

In certain embodiments, a parent drug of a HPP or HPC is selected from the group consisting of an antimicrobial and antimicrobial-related compound. The moiety of an antimicrobial or antimicrobial-related compound can be further converted to a lipophilic moiety as described supra.

Antimicrobials are substances that kill or inhibit the growth of microorganisms such as bacteria, fungi, or protozoans, as well as destroying or inhibit the growth of viruses. The main classes of antimicrobials include, for example, antibiotics that treat bacterial-related conditions, antivirals that treat viral-related conditions, antifungals that treat fungal-related conditions and antiparastics that treat parasite-related conditions.

An antimicrobial-related compound is a compound comprising an antimicrobial structure, an antimicrobial metabolite, or an agent that can be metabolized into an antimicrobial or antimicrobial metabolite after a HPP or HPC penetrates one or more biological barriers. An antimicrobial-related compound further includes a compound that is an analog or mimic of an antimicrobial or an antimicrobial metabolite, or an agent that can be metabolized into an analog or mimic of an antimicrobial or an antimicrobial metabolite, after a HPP or HPC penetrates one or more biological barriers.

Examples of antimicrobials include, for example, antibiotics that treat bacterial-related conditions, antivirals that treat viral-related conditions, antifungals that treat fungal-related conditions and antiprotozoals that treat protozoans-related conditions.

Examples of antibiotics include, without limitation, beta-lactam antibiotics, sulfonamides and quinolones. Beta-lactam antibiotics are well known in the art and are used in connection with various conditions. As used herein, a beta-lactam antibiotics refers to a compound that comprises a beta-lactam nucleus.

Examples of beta-lactam antibiotics include, but are not limited to, penicillin derivatives, cephalosporins, penems, monobactams, carbapenems, beta-lactamase inhibitors and combinations thereof. Examples of penicillin derivatives include, but are not limited to, aminopenicillins (e.g. amoxicillin, ampicillin, and epicillin), carboxypenicillins (e.g. carbenicillin, ticarcillin, and temocillin), ureidopenicillins (e.g. azlocillin, piperacillin and mezlocillin), mecillinam, sulbenicillin, benzathine penicillin, penicillin G (benzylpenicillin), penicillin V (phenoxymethylpenicillin), penicillin O (allylmercaptomethylpenicillinic), procaine penicillin, oxacillin, methicillin, nafcillin, cloxacillin, dicloxacillin, flucloxacillin, pivampicillin, hetacillin, becampicillin, metampicillin, talampicillin, co-amoxiclav (amoxicillin plus clavulanic acid), and piperacillion. Examples of cephalosporins include, but are not limited to, cephalexin, cephalothin, cefazolin, cefaclor, cefuroxime, cefamandole, cefotetan, cefoxitin, ceforanide, ceftriaxone, cefotaxime, cefpodoxime proxetil, ceftazidime, cefepime, cefoperazone, ceftizoxime, cefixime and cefpirome. Examples of penems include, without limitation, faropenem. Examples of monobactams include, without limitation, aztreonam and tigemonam. Examples of carbapenems include, but are not limited to, biapenem, .doripenem, ertapenem, .imipenem, .meropenem, .and panipenem. Examples of beta-lactamase inhibitors include, but are not limited to, tazobactam ([2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt), sulbactam ((2S,5R)-3,3-dimethyl-7-oxo-4-thia-1-azabicyclo[3.2.0]heptane-2-carboxylic acid 4,4-dioxide sodium), and clavulanic acid ((2R,5R,Z)-3-(2-hydroxyethylidene)-7-oxo-4-oxa-1-aza-bicyclo[3.2.0] heptane-2-carboxylic acid). Other examples of antibiotics include, without limitation, [(N-benzyloxycarbonylamino) methyl]-phosphonic acid mono-(4-nitrophenyl) ester sodium salt, [(N-benzyloxycarbonylamino)methyl]-phosphonic acid mono-(3-pyridinyl) ester sodium salt, sulfanilamide (4-aminobenzenesulfonamide), sulfasalazine (6-oxo-3-(2-[4-(N-pyridin-2-ylsulfamoyl)phenyl]hydrazono) cyclohexa-1,4-dienecarboxylic acid), 1-cyclopropyl-6-fluoro-4-oxo-7-piperazin-1-yl-quinoline-3-carboxylic acid, and nalidixic acid (1-ethyl-7-methyl-4-oxo-[1,8]naphthyridine-3-carboxylic acid), Examples of sulfonamides include, without limitation, sulfaisodimidine, sulfanilamide, sulfadiazine, sulfisoxazole, sulfamethoxazole, sulfadimethoxine, sulfamethoxypyridazine, sulfacetamide, sulfadoxine, acetazolamide, bumetanide, chlorthalidone, clopamide, furosemide, hydrochlorothiazide, indapamide, mefruside, metolazone, xipamide, dichlorphenamide, dorzolamide, acetazolamide, ethoxzolamide, sultiame, zonisamide, mafenide, celecoxib, darunavir, probenecid, sulfasalazine, and sumatriptan.

Examples of quinolones include, without limitation, cinoxacin, flumequine, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, gatifloxacin, grepafloxacin, levofloxacin, moxifloxacin, pazufloxacin, sparfloxacin, temafloxacin, tosufloxacin, clinafloxacin, gemifloxacin, sitafloxacin, trovafloxacin, prulifloxacin, garenoxacin, ecinofloxacin, delafloxacin and nalidixic acid.

Examples of antivirals include, without limitation, rifampicin, zanamivir and oseltamivir.

Examples of antifungals include, without limitation, polyene antifungals (e.g. natamycin, rimocidin, filipin, nystatin, amphotericin B and candicin), imidazole antifungals (e.g. miconazole, ketoconazloe, clotrimazole, econazole, bifonazole, butoconazole, fenticonazole, isoconazole, oxiconazole, sertaconazole, sulconazole, and tioconazole), triazoles antifungals (e.g. fluconazole, itraconazole, isavuconazole, ravuconazole, posaconazole, voriconazole, and terconazole), thiazole antifungals (e.g. abafungin), allyamines (e.g. terbinafine, amorolfine, naftifine and butenafine), echinocandins (e.g. anidulafungin, caspofungin and micafungin) and other antifungals such as benzoic acid, ciclopirox, tolnaftate, undecylenic acid, flucytosine, griseofulvin and haloprogin.

Examples of antiprotozoals include, without limitation, eflornithine, furazolidone, melarsoprol, metronidazole, ornidazole, paromomycin sulfate, pentamidine, pyrimethamine, and tinidazole.

In certain embodiments, a functional unit of a HPP of an antimicrobial or antimicrobial-related compound comprises a moiety having a structure of Structure F-1:

Structure F-1

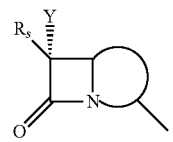

including stereoisomers and pharmaceutically acceptable salts thereof.

Unless otherwise specified in the specification, Y is selected from the group consisting of H, OH, NHCHO, NHC(=O)R$_6$, OC(=O)CH$_3$, OC(=O)R$_6$, OCH$_3$, OC$_2$H$_5$, OR$_6$, CH$_3$SO$_3$, R$_6$SO$_3$, NO$_2$, CN, CF$_3$, OCF$_3$, OC$_2$F$_5$, OC$_3$F$_7$, F, Br, I, Cl, and substituted and unsubstituted alkyloxyl;

is selected from the group consisting of Structure NS-1, Structure NS-2, Structure NS-3, Structure NS-4 and Structure NS-5:

Structure NS-1

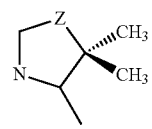

Structure NS-2

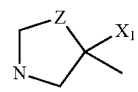

Structure NS-3

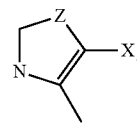

Structure NS-4

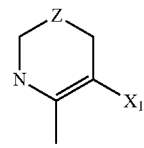

-continued

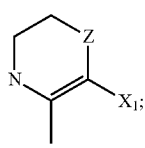
Structure NS-5

$X_1$ is selected from the group consisting of H, OH, $OCH_3$, $OC_2H_5$, $OR_6$, $C(=O)NH_2$, $CH_2OC(=O)NH_2$, $CH_2OC(=O)CH_3$, $CH_2OC(=O)R_6$, $OC(=O)CH_3$, $OC(=O)R_6$, $CH_2OCH_3$, $CH_3$, $C_2H_5$, $R_6$, Cl, F, Br, I, $HC=CHCH_3$, $HC=CH_2$, $CH_2OCH_3$, $CH_2OR_6$, $S(CH_2)_n$—$NHR_7$, Structure $X_1$-1, Structure $X_1$-2, Structure $X_1$-3, Structure $X_1$-4, Structure $X_1$-5, Structure $X_1$-6, Structure $X_1$-7, Structure $X_1$-8, Structure $X_1$-9, Structure $X_1$-10, Structure $X_1$-11, Structure $X_1$-12, Structure $X_1$-13, Structure $X_1$-14, Structure $X_1$-15, Structure $X_1$-16, Structure $X_1$-17, Structure $X_1$-18, Structure $X_1$-19, Structure $X_1$-20, Structure $X_1$-21, Structure $X_1$-22, Structure $X_1$-23, Structure $X_1$-24, Structure $X_1$-25, Structure $X_1$-26, Structure $X_1$-27, Structure $X_1$-28, Structure $X_1$-29, Structure $X_1$-30, Structure $X_1$-31, Structure $X_1$-32, Structure $X_1$-33, Structure $X_1$-34, Structure $X_1$-35, Structure $X_1$-36, Structure $X_1$-37, Structure $X_1$-38, Structure $X_1$-39, Structure $X_1$-40, Structure $X_1$-41, Structure $X_1$-42, Structure $X_1$-43, Structure $X_1$-44, Structure $X_1$-45, Structure $X_1$-46, Structure $X_1$-47, Structure $X_1$-48, Structure $X_1$-49, Structure $X_1$-50, Structure $X_1$-51, Structure $X_1$-52, Structure $X_1$-53, Structure $X_1$-54, Structure $X_1$-55, Structure $X_1$-56, Structure $X_1$-57, Structure $X_1$-58, Structure $X_1$-59, Structure $X_1$-60, Structure $X_1$-61, Structure $X_1$-62, Structure $X_1$-63, Structure $X_1$-64, Structure $X_1$-65, Structure $X_1$-66, Structure $X_1$-67, Structure $X_1$-68, Structure $X_1$-69, Structure $X_1$-70, Structure $X_1$-71, Structure $X_1$-72, Structure $X_1$-73, Structure $X_{17}$-4, Structure $X_1$-75, Structure $X_1$-76, Structure $X_1$-77, Structure $X_1$-78, Structure $X_1$-79, Structure $X_1$-80, Structure $X_1$-81, and Structure $X_1$-82:

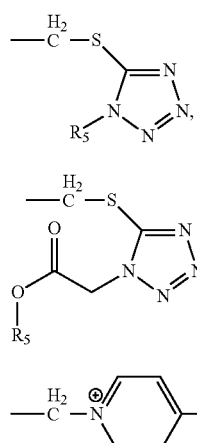
Structure $X_1$-1

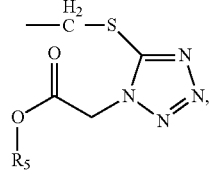
Structure $X_1$-2

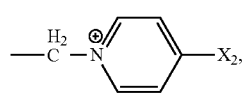
Structure $X_1$-3

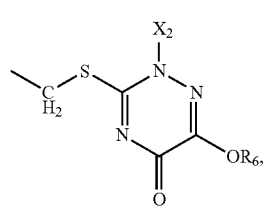
Structure $X_1$-4

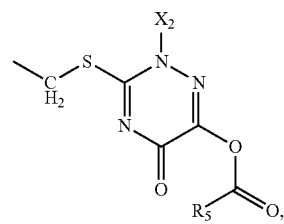
Structure $X_1$-5

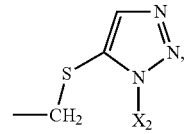
Structure $X_1$-6

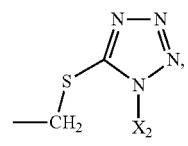
Structure $X_1$-7

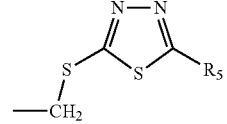
Structure $X_1$-8

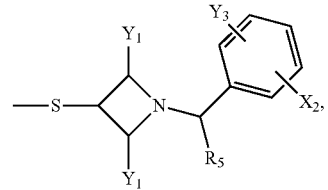
Structure $X_1$-9

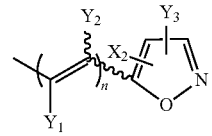
Structure $X_1$-10

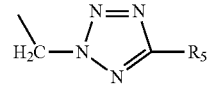
Structure $X_1$-11

Structure $X_1$-12

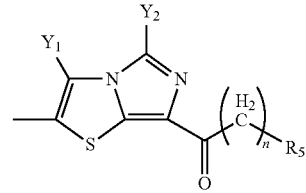
Structure $X_1$-13

-continued
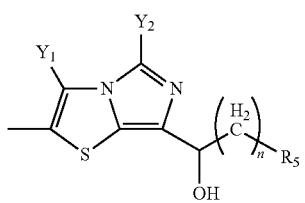
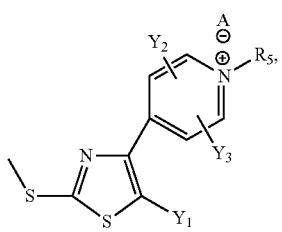
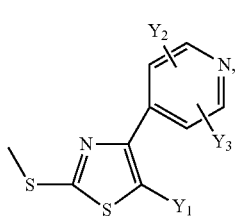
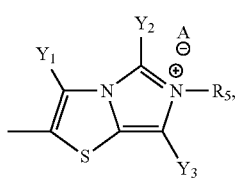
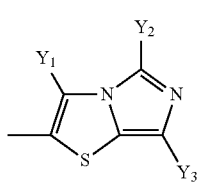
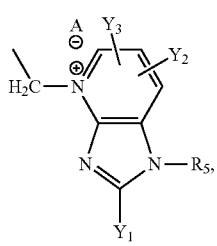
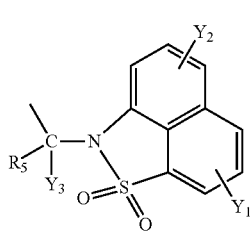
Structure X₁-14
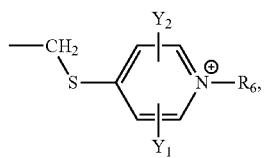
Structure X₁-15
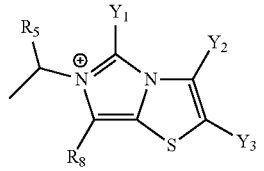
Structure X₁-16
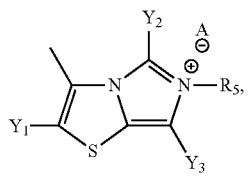
Structure X₁-17
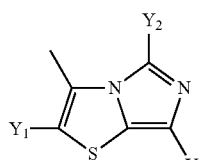
Structure X₁-18
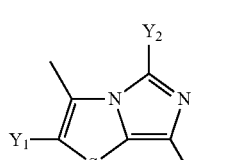
Structure X₁-19
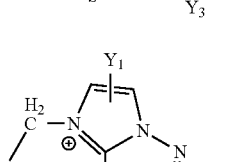
Structure X₁-20
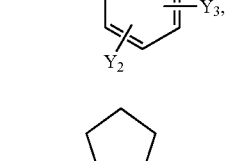
Structure X₁-21
Structure X₁-22
Structure X₁-23
Structure X₁-24
Structure X₁-25
Structure X₁-26
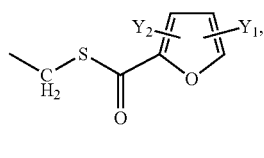
Structure X₁-27
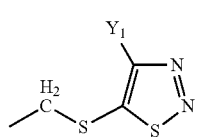
Structure X₁-28
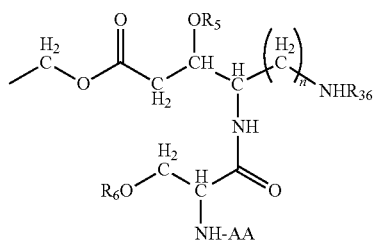
Structure X₁-29

-continued
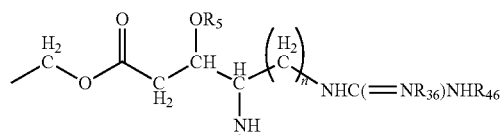
Structure X₁-30
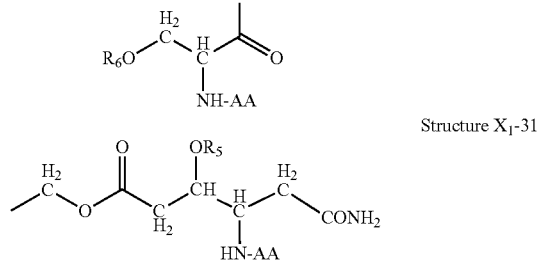
Structure X₁-31
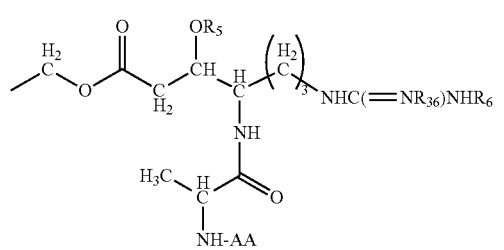
Structure X₁-32
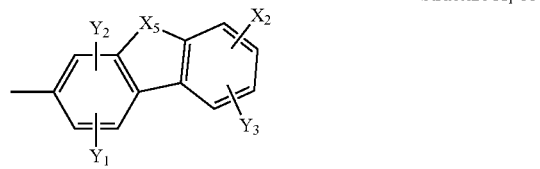
Structure X₁-33
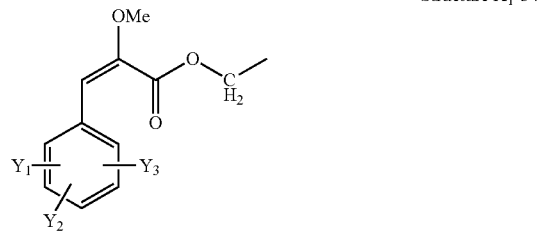
Structure X₁-34
Structure X₁-35
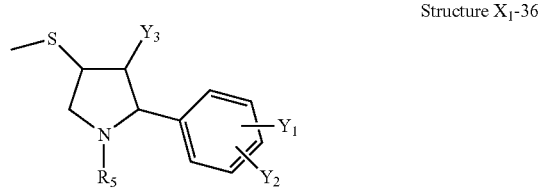
Structure X₁-36
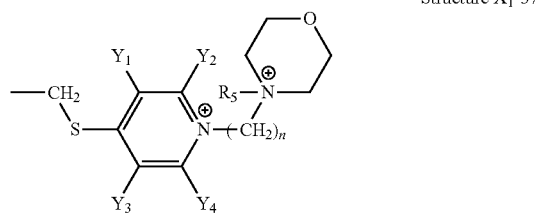
Structure X₁-37
-continued
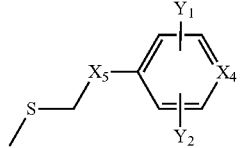
Structure X₁-38
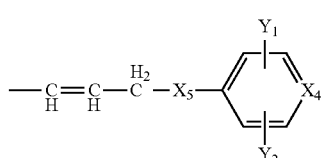
Structure X₁-39
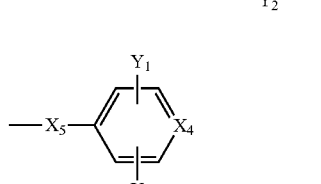
Structure X₁-40
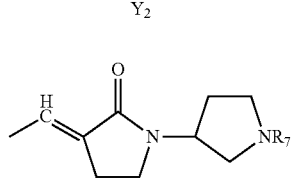
Structure X₁-41
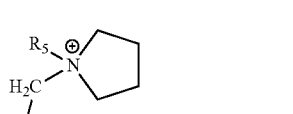
Structure X₁-42
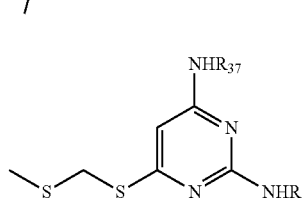
Structure X₁-43
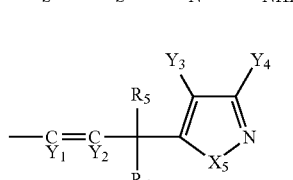
Structure X₁-44
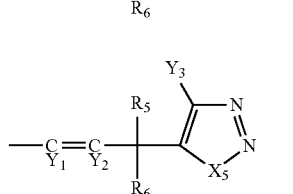
Structure X₁-45
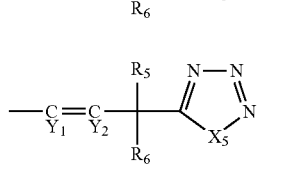
Structure X₁-46
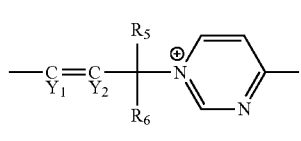
Structure X₁-47

Structure X₁-48
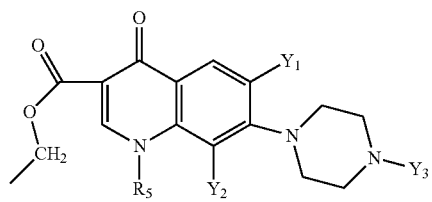
Structure X₁-49
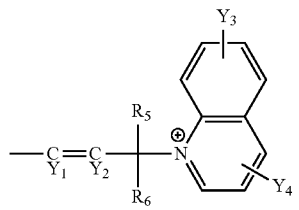
Structure X₁-50
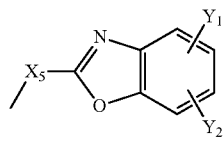
Structure X₁-51
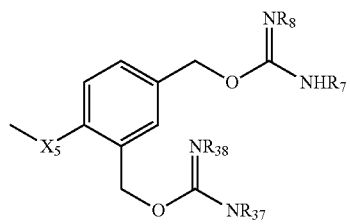
Structure X₁-52
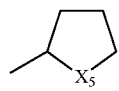
Structure X₁-53
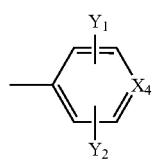
Structure X₁-54
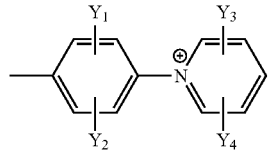
Structure X₁-55
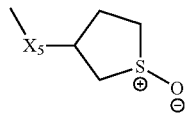
Structure X₁-56
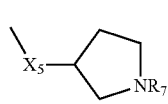
Structure X₁-57
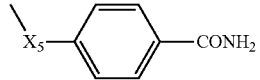
Structure X₁-58
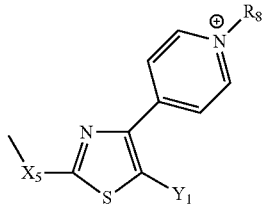
Structure X₁-59
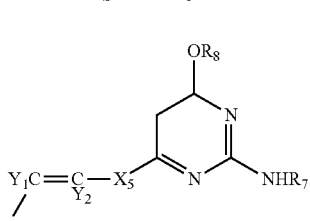
Structure X₁-60
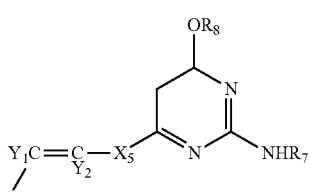
Structure X₁-61
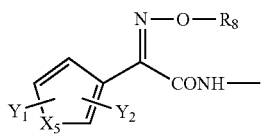
Structure X₁-62
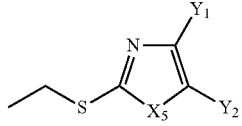
Structure X₁-63
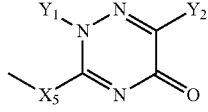
Structure X₁-64
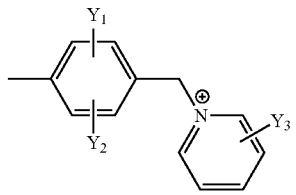
Structure X₁-65
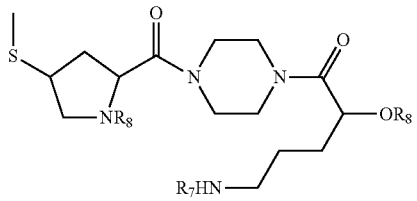
Structure X₁-66
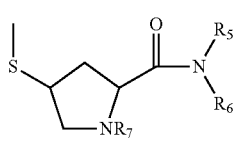

Structure X₁-67
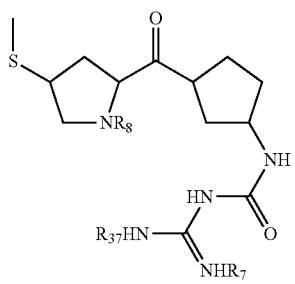

Structure X₁-68
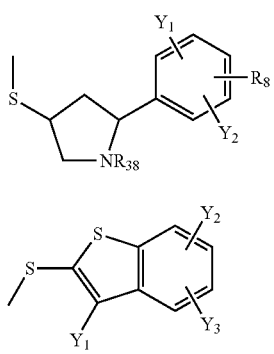

Structure X₁-69
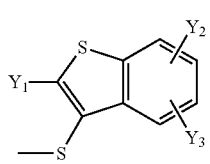

Structure X₁-70
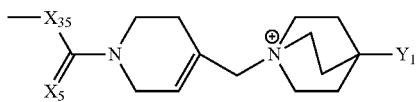

Structure X₁-71
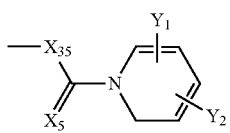

Structure X₁-72
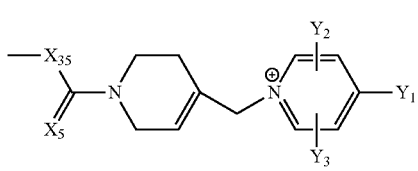

Structure X₁-73
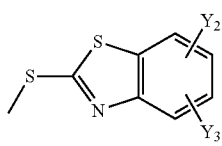

Structure X₁-74
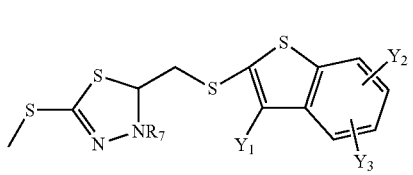

Structure X₁-75
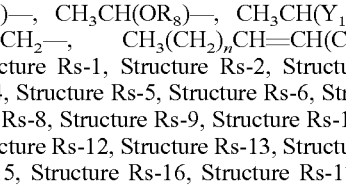

Structure X₁-76
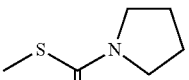

Structure X₁-77
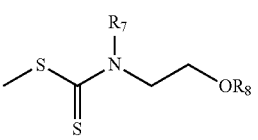

Structure X₁-78
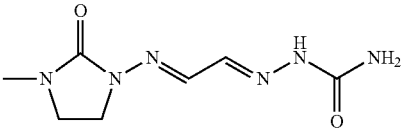

Structure X₁-79
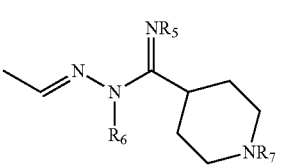

Structure X₁-80
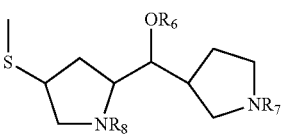

Structure X₁-81
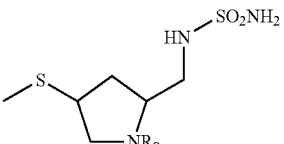

Structure X₁-82
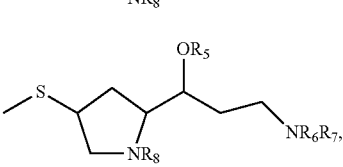

$R_s$— taken together with Y is $R_6OCH_2C(R_5)=$, or by itself is selected from the group consisting of $R_6OOCCH(NHR_7)(CH_2)_nC(=O)NH—$, $R_6OOCCH(NHR_7)(CH_2)_nSC(=O)NH—$, $CF_3SCH_2C(=O)NH—$, $CF_3CH_2C(=O)NH—$, $CHF_2SCH_2C(=O)NH—$, $CH_2FSCH_2C(=O)NH—$, $NH_2C(=O)CHFS—CH_2C(=O)NH—$, $R_7NHCH(C(=O)OW)CH_2SCH_2C(=O)NH—$, $R_7NHCH(L_1\text{-}L_4\text{-}L_2\text{-}W)CH_2SCH_2C(=O)NH—$, $CNCH_2SCH_2C(=O)NH—$, $CH_3(CH_2)_nC(=O)NH—$, $R_7N=CHNR_7CH_2CH_2S—$, $R_7N=C(NHR_7)NHC(=O)—$, $R_7N=C(NHR_7)NHC(=O)CH_2$, $CH_3C(Cl)=CHCH_2SCH_2C(=O)NH—$, $(CH_3)_2C(OR_6)—$, $CNCH_2C(=O)NH—$, $CNCH_2CH_2S—$, $R_7HN=CH(NR_7)CH_2CH_2S—$, $CH_2=CHCH_2SCH_2C(=O)NH—$, $CH_3CH(OH)—$, $CH_3CH(OR_8)—$, $CH_3CH(Y_1)—$, $(CH_3)_2CH—$, $CH_3CH_2—$, $CH_3(CH_2)_nCH=CH(CH_2)_mC(=O)NH—$, Structure Rs-1, Structure Rs-2, Structure Rs-3, Structure Rs-4, Structure Rs-5, Structure Rs-6, Structure Rs-7, Structure Rs-8, Structure Rs-9, Structure Rs-10, Structure Rs-11, Structure Rs-12, Structure Rs-13, Structure Rs-14, Structure Rs-15, Structure Rs-16, Structure Rs-17, Structure Rs-18, Structure Rs-19, Structure Rs-20, Structure Rs-21, Structure Rs-22, Structure Rs-23, Structure Rs-24, Structure Rs-25, Structure Rs-26, Structure Rs-27, Structure Rs-28, Structure Rs-29, Structure Rs-30, Structure Rs-31, Structure Rs-32, Structure Rs-33, Structure Rs-34, Structure Rs-35, Structure Rs-36, Structure Rs-37, Structure Rs-38, Structure Rs-39, Structure Rs-40, Structure Rs-41, Structure Rs-42, Structure Rs-43, Structure Rs-44, Structure Rs-45, and Structure Rs-46:

Structure Rs-1
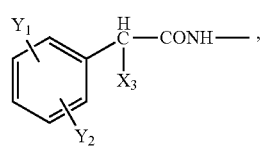

Structure Rs-2
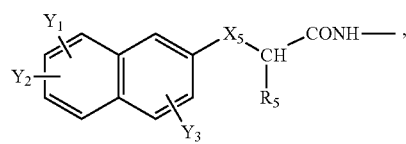

Structure Rs-3
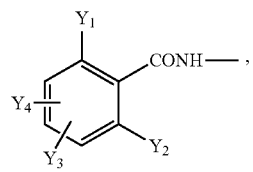

Structure Rs-4
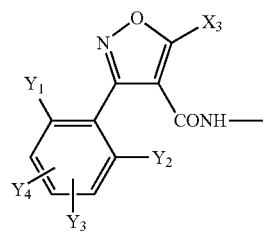

Structure Rs-5
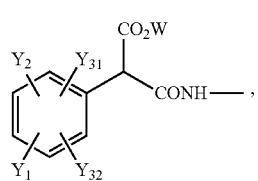

Structure Rs-6
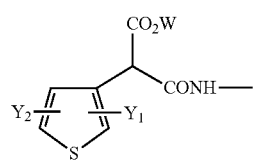

Structure Rs-7
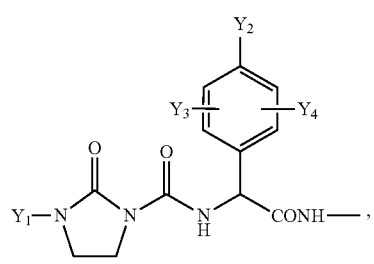

Structure Rs-8
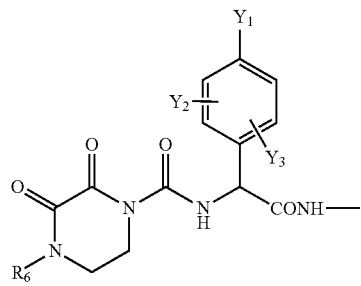

Structure Rs-9
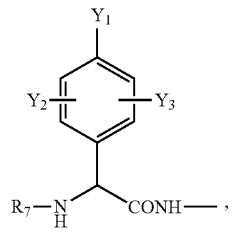

Structure Rs-10
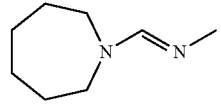

Structure Rs-11
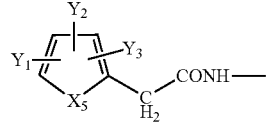

Structure Rs-12
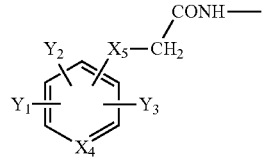

Structure Rs-13
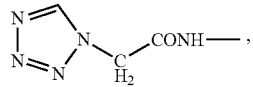

Structure Rs-14
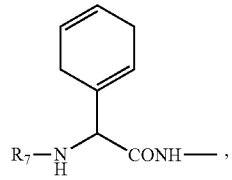

Structure Rs-15
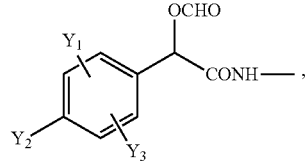

Structure Rs-16
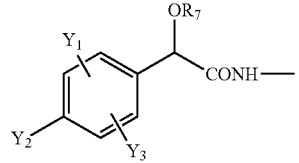

-continued
Structure Rs-17
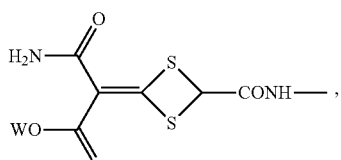
Structure Rs-18
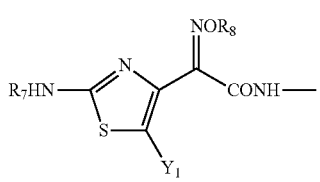
Structure Rs-19
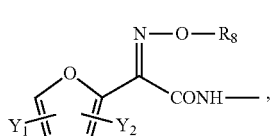
Structure Rs-20
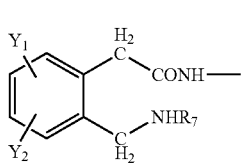
Structure Rs-21
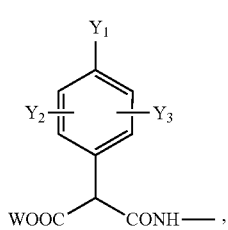
Structure Rs-22
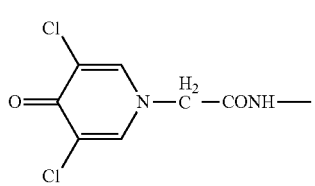
Structure Rs-23
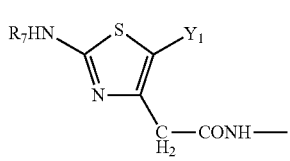
Structure Rs-24
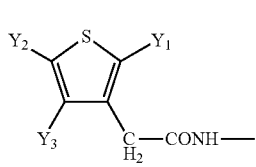
Structure Rs-25
Structure Rs-26
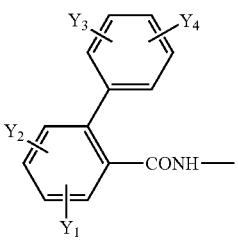
Structure Rs-27
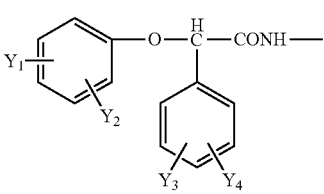
Structure Rs-28
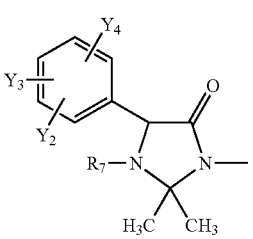
Structure Rs-29
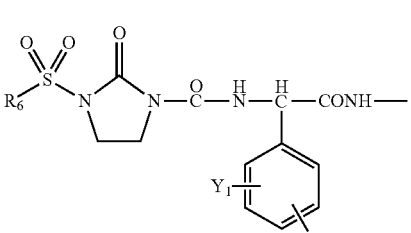
Structure Rs-30
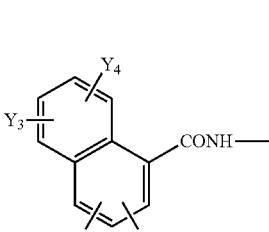
Structure Rs-31
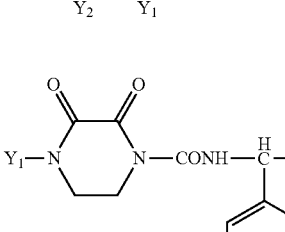
Structure Rs-32
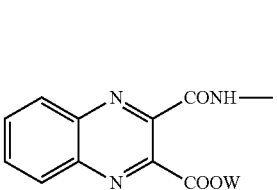

Structure Rs-33
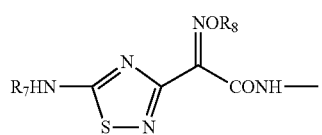
Structure Rs-34
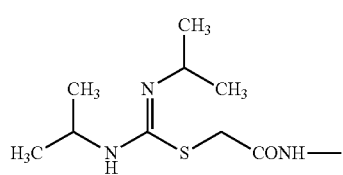
Structure Rs-35
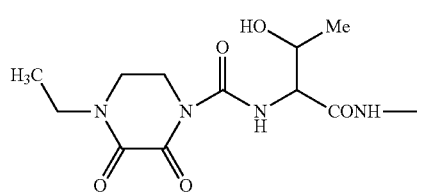
Structure Rs-36
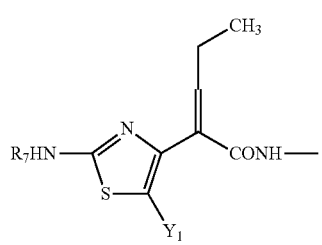
Structure Rs-37
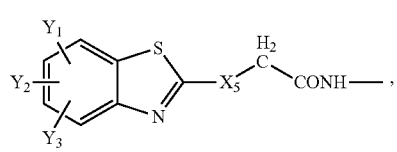
Structure Rs-38
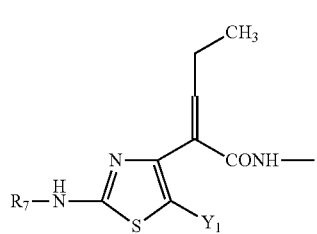
Structure Rs-39
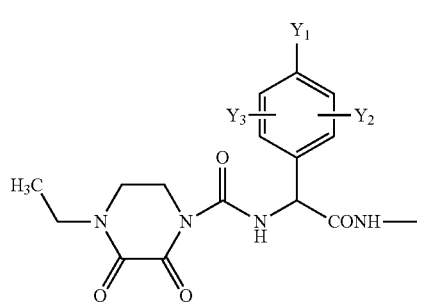
Structure Rs-40
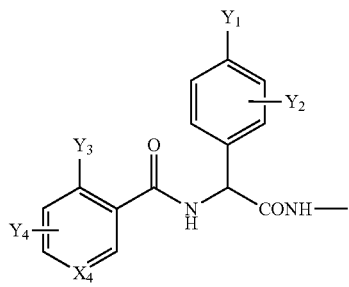
Structure Rs-41
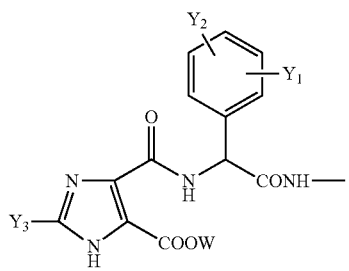
Structure Rs-42
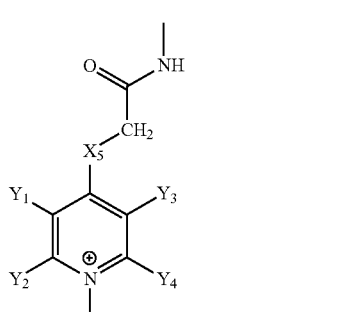
Structure Rs-43
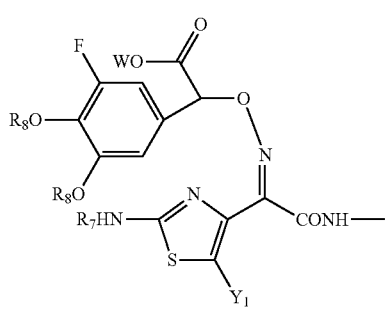
Structure Rs-44
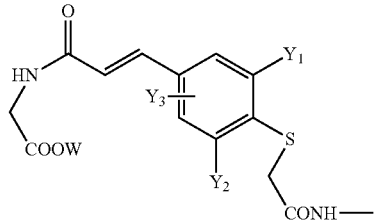
Structure Rs-45
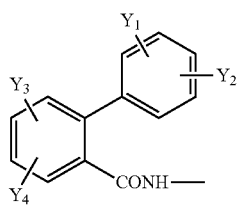

Structure Rs-46

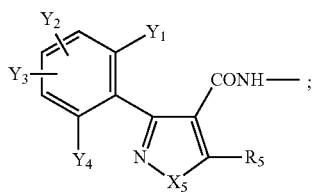

W is selected from the group consisting of H, substituted and unsubstituted alkyl, substituted and unsubstituted alkyloxy, substituted and unsubstituted alkenyl, substituted and unsubstituted alkynyl, substituted and unsubstituted aryl, substituted and unsubstituted heteroaryl, Structure Wa, Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18:

Structure Wa

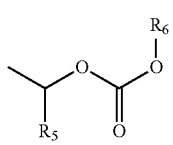

Structure W-1

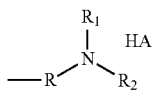

Structure W-2

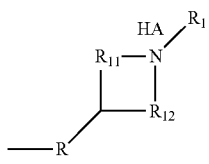

Structure W-3

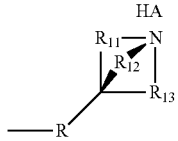

Structure W-4

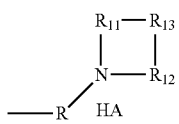

Structure W-5

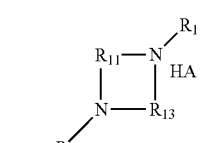

Structure W-6

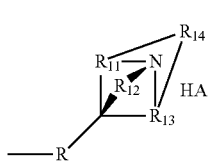

Structure W-7

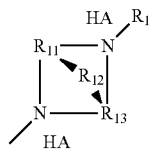

Structure W-8

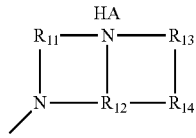

Structure W-9

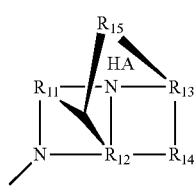

Structure W-10

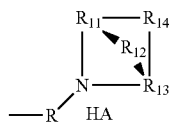

Structure W-11

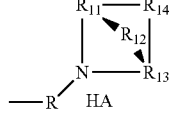

Structure W-12

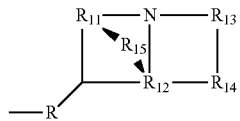

Structure W-13

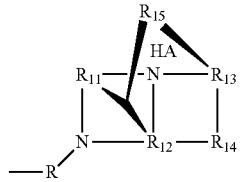

Structure W-14

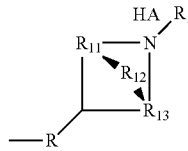

Structure W-15

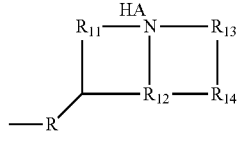

Structure W-16

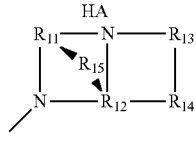

-continued

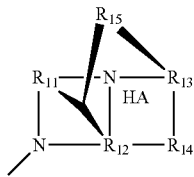

Structure W-17

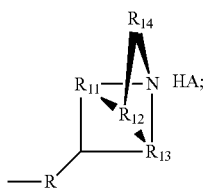

Structure W-18

Z is selected from the group consisting of $CH_2$, S, SO, $SO_2$, NH, $NR_6$, $CHCH_3$, $CHCH_2CH_3$, $CHR_6$, $R_6$, —C(=O)—, and O;

AA represents any amino acids;

each m and n is independently selected from the group of 0 and integer, e.g. 0, 1, 2, 3, 4, 5, 6, 7, 8, 9, 10, 11, 12, 13, 14, 15, 16, 17, 18, 19, 20, . . . ;

HA is selected from the group consisting of nothing, and pharmaceutically acceptable acid, e.g. hydrochloride hydrobromide, hydroiodide, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid and pamoic acid;

R is selected from the group consisting of nothing, H, $CH_2C(=O)OR_6$, substituted and unsubstituted alkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl, wherein any $CH_2$ in R may be further replaced with O, S, P, $NR_6$, or any other pharmaceutically acceptable groups;

$R_1$-$R_3$ are independently selected from the group consisting of H, substituted and unsubstituted alkyl, substituted and unsubstituted alkyloxyl, substituted and unsubstituted alkenyl, substituted and unsubstituted alkynyl, substituted and unsubstituted aryl and substituted and unsubstituted heteroaryl residues;

$R_5$ and $R_{35}$ are independently selected from the group consisting of H, $C(=O)NH_2$, $CH_2CH_2OR_6$, $CH_2CH_2N(CH_3)_2$, $CH_2CH_2N(CH_2CH_3)_2$, Cl, F, Br, I, substituted and unsubstituted alkyl, substituted and unsubstituted cycloalkyl, substituted and unsubstituted alkyloxyl, substituted and unsubstituted cycloalkyloxyl, substituted and unsubstituted aryl, substituted and unsubstituted heteroaryl, substituted and unsubstituted alkylcarbonyl, substituted and unsubstituted alkylamino, —C(=O)—W, $L_1$-$L_4$-$L_2$-W, and W;

$R_6$, $R_{36}$ and $R_{46}$ are independently selected from the group consisting of H, F, Cl, Br, I, $Na^+$, $K^+$, $C(=O)R_5$, 2-oxo-1-imidazolidinyl, phenyl, 5-indanyl, 2,3-dihydro-1H-inden-5-yl, 4-hydroxy-1,5-naphthyridin-3-yl, substituted and unsubstituted alkyl, substituted and unsubstituted cycloalkyl, substituted and unsubstituted alkenyl, substituted and unsubstituted alkynyl, substituted and unsubstituted alkyloxyl, substituted and unsubstituted cycloalkyloxyl, substituted and unsubstituted aryl, substituted and unsubstituted heteroaryl, —C(=O)—W, -$L_1$-$L_4$-$L_2$-W, and W;

$R_7$ and $R_{37}$ are independently selected from the group consisting of H, F, Cl, Br, I, $CH_3NHC(=O)CH_2CH(NHR_8)C(=O)$, $R_5N=C(NHR_6)NHC(=O)$—, $C(=O)CH_3$, $C(=O)R_6$, $PO(OR_5)OR_6$, substituted and unsubstituted alkyl, substituted and unsubstituted alkyloxyl, substituted and unsubstituted alkenyl, substituted and unsubstituted alkynyl, substituted and unsubstituted aryl, substituted and unsubstituted heteroaryl, substituted and unsubstituted alkylcarbonyl, substituted and unsubstituted alkylamino, $L_1$-$L_4$-$L_2$-W, and C—(=O)—W;

$R_8$ and $R_{38}$ are independently selected from the group consisting of H, F, Cl, Br, I, $CH_3$, $C_2H_5$, $CF_3$, $CH_2CH_2F$, $CH_2CH_2Cl$, $CH_2CH_2Br$, $CH_2CH_2I$, $CH_2CHF_2$, $CH_2CF_3$, $CH_2F$, $CH_2Cl$, $CH_2Br$, $CH_2I$, $CH_2NR_6R_7$, $CH(NHR_7)CH_2C(=O)NH_2$, $C_3H_7$, $C_4H_9$, $C_6H_{11}$, $R_6$, $C(=O)R_6$, $C(=O)NH_2$, $CH_2C(=O)NH_2$, $CH_2OC(=O)NH_2$, $PO(OR_5)OR_6$, $C(CH_3)_2C(=O)OR_6$, $CH(CH_3)C(=O)OR_6$, $CH_2C(=O)OR_6$, $C(=O)$—W, $L_1$-$L_4$-$L_2$-W, W, substituted and unsubstituted perfluoroalkyl, substituted and unsubstituted alkoxyl, substituted and unsubstituted alkylamino, substituted and unsubstituted perfluoroalkyl, substituted and unsubstituted alkyl halide and substituted and unsubstituted alkylcarbonyl;

$R_{11}$-$R_{16}$ are independently selected from the group consisting of nothing, H, $CH_2C(=O)OR_{11}$, substituted and unsubstituted alkyl, substituted and unsubstituted alkoxyl, substituted and unsubstituted perfluoroalkyl, substituted and unsubstituted alkyl halide, substituted and unsubstituted alkenyl, substituted and unsubstituted alkynyl, substituted and unsubstituted aryl, and substituted and unsubstituted heteroaryl;

$X_2$ is selected from the group consisting of nothing, H, $CH_2(CH_2)_nOR_8$, Cl, F, Br, I, $NO_2$, CN, $CF_3$, $C_2F_5$, $C_3F_7$, $OCF_3$, $OC_2F_5$, $NH_2$, $NHR_6$, $CH_3$, $C_2H_5$, $R_6$, $C(=O)NH_2$, $CH_2OC(=O)NH_2$, $CH_2C(=O)OR_5$, $CH_2(CH_2)_nN(CH_3)_2$, $CH_2(CH_2)_nSO_3R_5$, substituted and unsubstituted perfluoroalkyl, substituted and unsubstituted alkyl, substituted and unsubstituted alkylthio, and substituted and unsubstituted alkylamino, and substituted and unsubstituted alkyloxyl;

$X_3$ is selected from the group consisting of nothing, H, $N_3$, $SO_3W$, F, Cl, Br, OH, $OCH_3$, $OR_6$, $CH_3$, $R_6$, $C(=O)OW$, OW, $L_1$-$L_4$-$L_2$-W, and I;

$X_4$ is selected from the group consisting of nothing, N, CH, and $CY_1$;

$X_5$ and $X_{35}$ are independently selected from the group consisting of nothing, C(=O), OC(=O), $CH_2$, CH, S, O and $NR_5$;

$Y_1$, $Y_{31}$, $Y_2$, $Y_{32}$, $Y_3$, and $Y_4$ are independently selected from the group consisting of H, OH, OW, OC(=O)W, $L_1$-$L_4$-$L_2$-W, OC(=O)$CH_3$, $CH_3$, $C_2H_5$, $C_3H_7$, $C_4H_9$, $R_6$, $SO_3R_6$, $CH_2OR_6$, $CH_2OC(=O)R_6$, $CH_2C(=O)OR_8$, $OCH_3$, $OC_2H_5$, $OR_6$, $CH_3SO_2$, $R_6SO_2$, $CH_3SO_3$, $R_6SO_3$, $NO_2$, CN, $CF_3$, $OCF_3$, $CH_2(CH_2)_nNR_5R_6$, $CH_2(CH_2)_nOR_6$, $CH(C(=O)NH_2)NHR_6$, $CH_2C(=O)NH_2$, F, Br, I, Cl, CH=CHC(=O)NHCH$_2$C(=O)OW, CH=CHC(=O)NHCH$_2$L$_1$-L$_4$-L$_2$-W, $NR_8C(=O)R_5$, $SO_2NR_5R_8$, $C(=O)R_5$, $SR_5$, substituted and unsubstituted perfluoroalkyl, substituted and unsubstituted alkoxyl, substituted and unsubstituted alkylthio, substituted and unsubstituted alkylamino, substituted and unsubstituted perfluoroalkyl, substituted and unsubstituted alkyl halide and substituted and unsubstituted alkylcarbonyl;

$L_1$ is selected from the group consisting of nothing, O, S, —N($L_3$)-, —N($L_3$)-CH$_2$—O, —N($L_3$)-CH$_2$—N($L_5$)-, —O—CH$_2$—O—, —O—CH($L_3$)-O, and —S—CH($L_3$)-O—;

$L_2$ is selected from the group consisting of nothing, O, S, —N($L_3$)-, —N($L_3$)-CH$_2$—O, —N($L_3$)-CH$_2$—N($L_5$)-, —O—CH$_2$—O—, —O—CH($L_3$)-O—S—CH$_2$($L_3$)-O—, —O-$L_3$-, —N-$L_3$-, —N($L_3$)-$L_5$- and $L_3$;

$L_4$ is selected from the group consisting of C=O, C=S,

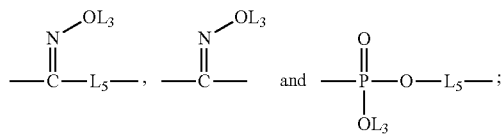

for each $L_1$, $L_2$, and $L_4$, $L_3$ and $L_5$ are independently selected from the group consisting of nothing, H, CH$_2$C(=O)O$L_6$, substituted and unsubstituted alkyl, substituted and unsubstituted cycloalkyl, substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, P, N$L_3$, or any other pharmaceutically acceptable groups;

$L_6$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)O$L_6$, CH=CH, C≡C, CH$L_6$, C$L_6L_7$, aryl, heteroaryl, or cyclic groups;

$L_7$ is independently selected from the group consisting of H, OH, Cl, F, Br, I, substituted and unsubstituted alkyl, substituted and unsubstituted cycloalkyl, and substituted and unsubstituted heterocycloalkyl, substituted and unsubstituted aryl, substituted and unsubstituted heteroaryl, substituted and unsubstituted alkoxyl, substituted and unsubstituted alkylthio, substituted and unsubstituted alkylamino, substituted and unsubstituted perfluoroalkyl, and substituted and unsubstituted alkyl halide, wherein any carbon or hydrogen may be further independently replaced with O, S, N, P(O)O$L_6$, CH=CH, C≡C, CH$L_6$, C$L_6L_7$, aryl, heteroaryl, or cyclic groups; and any CH$_2$ groups may be replaced with O, S, or NH.

In certain embodiments, a functional unit of a HPP or HPC of an antimicrobial or antimicrobial-related compound comprises a moiety having a structure selected from the group consisting of Structure FP-1, Structure FP-2, Structure FP-3, Structure FP-4, Structure FP-5, Structure FP-6, Structure FP-7, Structure FP-8, Structure FP-9, Structure FP-10, Structure FP-11, Structure FP-12, Structure FP-13, Structure FP-14, Structure FP-15, Structure FP-16, Structure FP-17, Structure FP-18, Structure FP-19, Structure FP-20, Structure FP-21, Structure FP-22, Structure FP-23, Structure FP-24, Structure FP-25, Structure FP-26, Structure FP-27, Structure FP-28, Structure FP-29, Structure FP-30, Structure FP-31, Structure FP-32, Structure FP-33, Structure FP-34, Structure FP-35, Structure FP-36, Structure FP-37, Structure FP-38, Structure FP-39, Structure FP-40, Structure FP-41, Structure FP-42, Structure FP-43, Structure FP-44, Structure FP-45, Structure FP-46, Structure FP-47, Structure FP-48, Structure FP-49, Structure FP-50, Structure FP-51, Structure FP-52, Structure FP-53, Structure FP-54, Structure FP-55, Structure FP-56, Structure FP-57, Structure FP-58, Structure FP-59, Structure FP-60, Structure FP-61, Structure FP-62, Structure FP-63, Structure FP-64, Structure FP-65, Structure FP-66, Structure FP-67, Structure FP-68, Structure FP-69, Structure FP-70, Structure FP-71, Structure FP-72, Structure FP-73, Structure FP-74, Structure FP-75, Structure FP-76, Structure FP-77, Structure FP-78, Structure FP-79, Structure FP-80, Structure FP-81, Structure FP-82, Structure FP-83, Structure FP-84, Structure FP-85, Structure FP-86, Structure FI-1, Structure FI-2, Structure FI-3, Structure FI-4, Structure FI-5, Structure FI-6, Structure FI-7, Structure FI-8, Structure FI-9, Structure FI-10, Structure FI-11, Structure FI-12, Structure FI-13, Structure FI-14, Structure FI-15, Structure FI-16, Structure FI-17, Structure FI-18, Structure FI-19, Structure FI-20, Structure FI-21, Structure FI-22, Structure FI-23, Structure FI-24, Structure FI-25, Structure FI-26, Structure FI-27, Structure FI-28, Structure FI-29, Structure FI-30, Structure FI-31, Structure FI-32, Structure FI-33, Structure FS-1, Structure FS-2, Structure FS-3, Structure FS-4, Structure FS-5, Structure FS-6, Structure FS-7, Structure FS-8, Structure FS-9, Structure FS-10, Structure FS-11, Structure FS-12, Structure FS-13, Structure FS-14, Structure FS-15, Structure FS-16, Structure FS-17, Structure FS-18, Structure FS-19, Structure FS-20, Structure FT-1, Structure FT-2, Structure FT-3, Structure FT-4, Structure FT-5, Structure FT-6, Structure FT-7, Structure FT-8, Structure FT-9, Structure FT-10, Structure FT-11, Structure FT-12, Structure FT-13, Structure FT-14, Structure FT-15, and Structure FT-16:

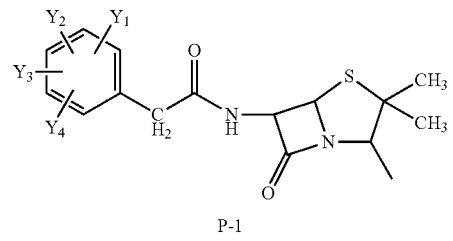

Structure FP-1

P-1

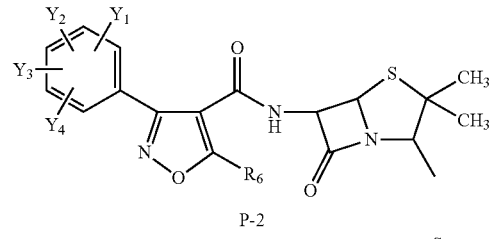

Structure FP-2

P-2

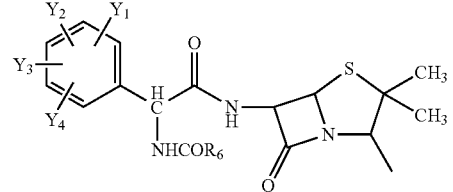

Structure FP-3

Structure FP-4
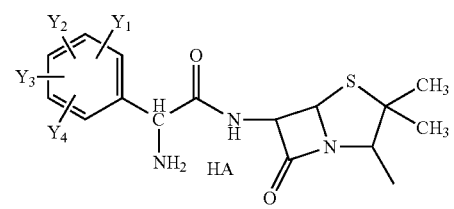
Structure FP-5
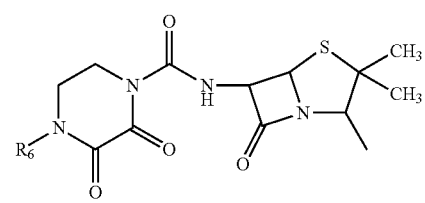
Structure FP-6
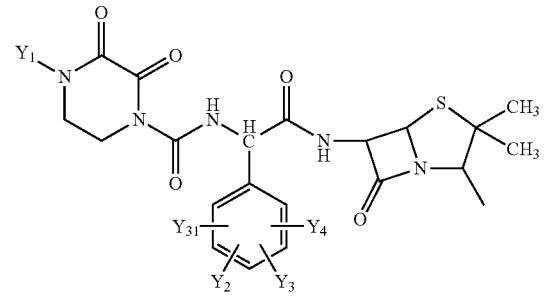
Structure FP-7
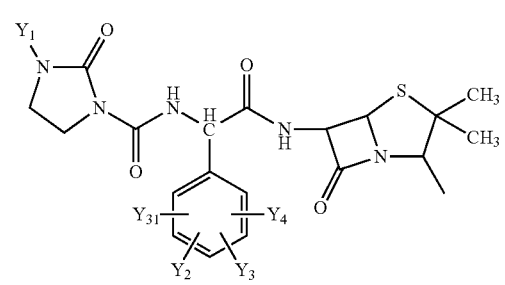
Structure FP-8
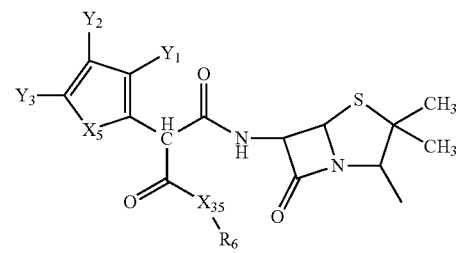
Structure FP-9
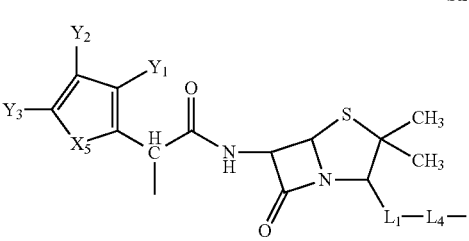
Structure FP-10
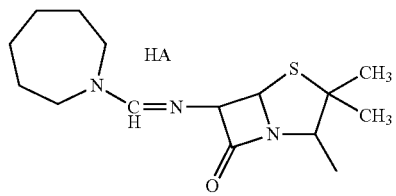
Structure FP-11
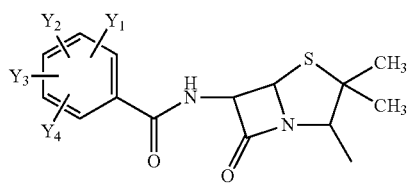
Structure FP-12
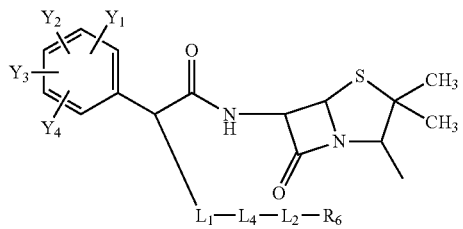
Structure FP-13
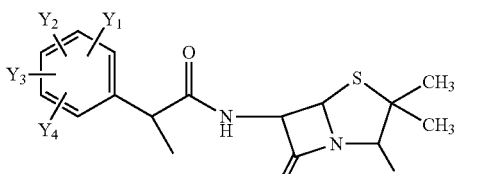
Structure FP-14
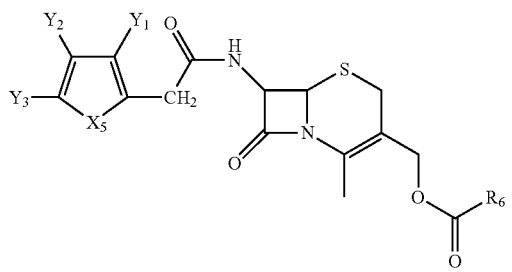
Structure FP-15
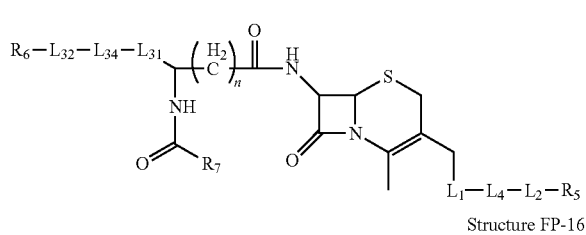
Structure FP-16
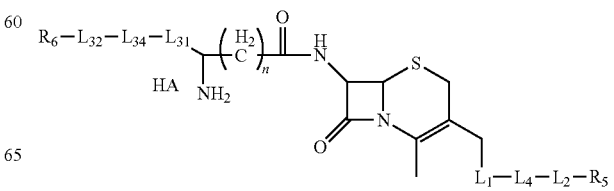

Structure FP-17
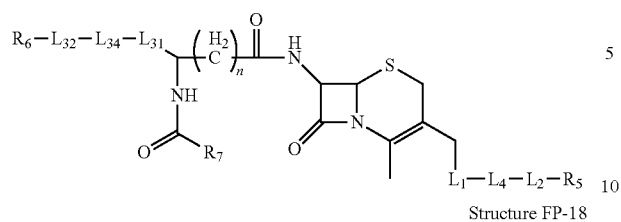
Structure FP-18
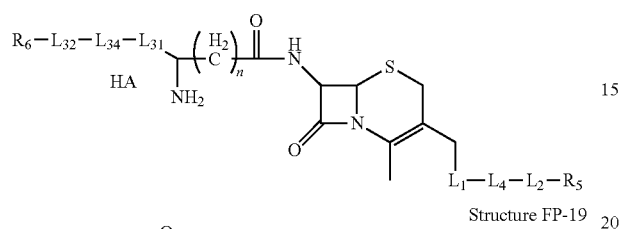
Structure FP-19
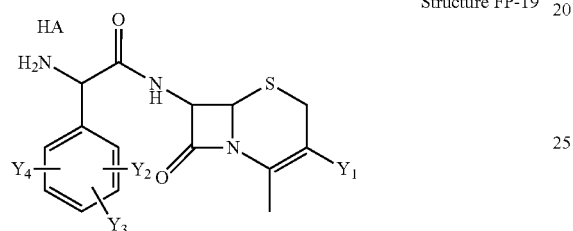
Structure FP-20
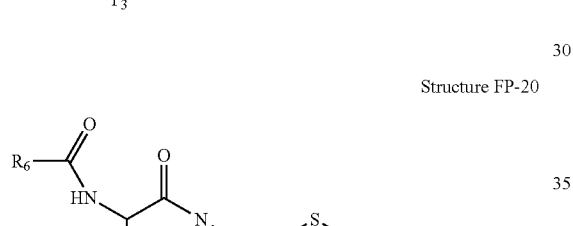
Structure FP-21
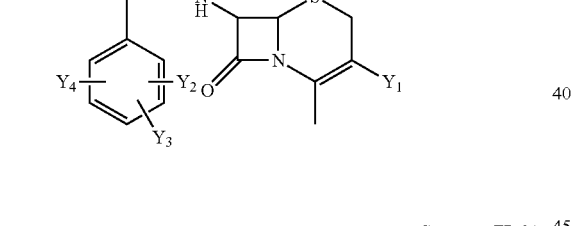
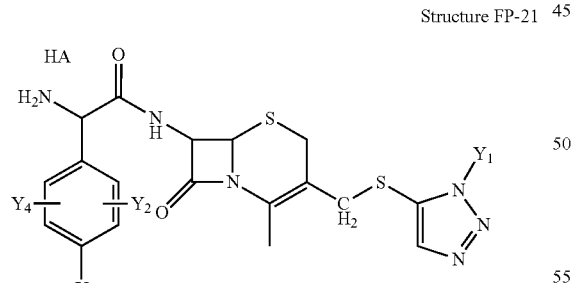
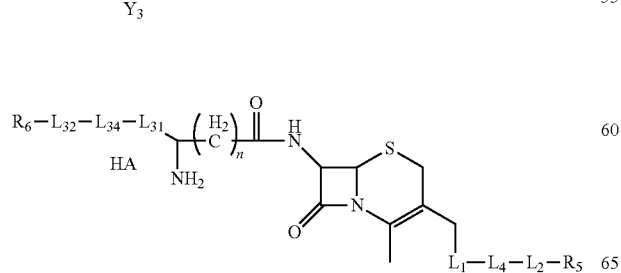
Structure FP-19
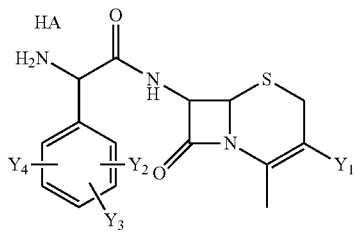
Structure FP-20
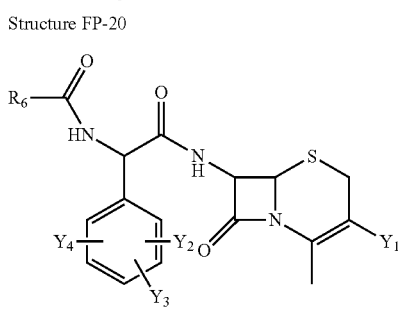
Structure FP-21
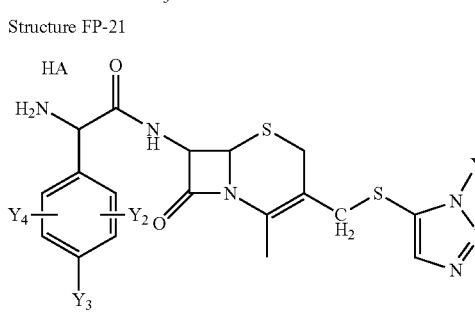
Structure FP-22
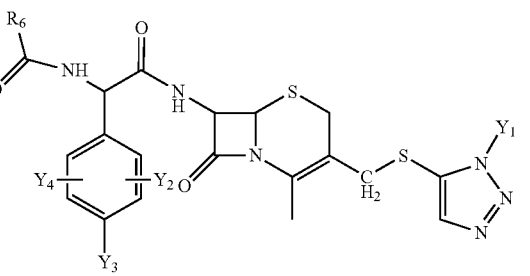
Structure FP-23
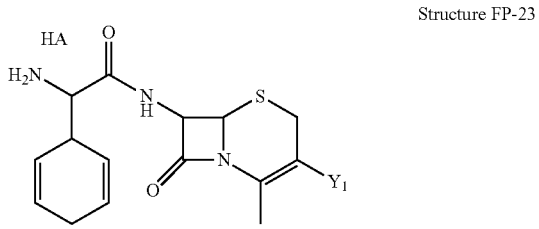
Structure FP-24
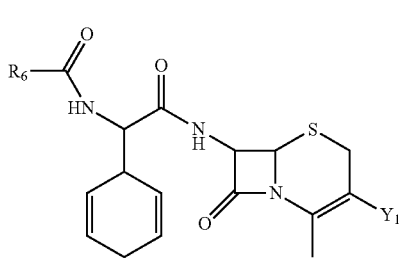

Structure FP-25
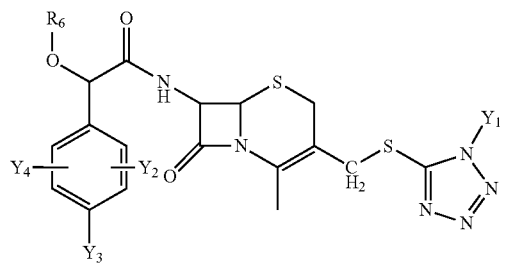
Structure FP-26
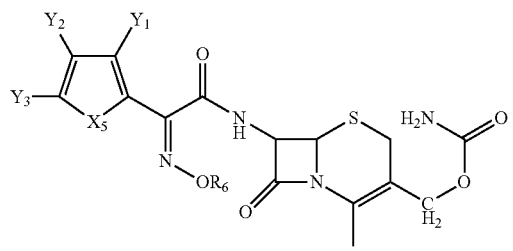
Structure FP-27
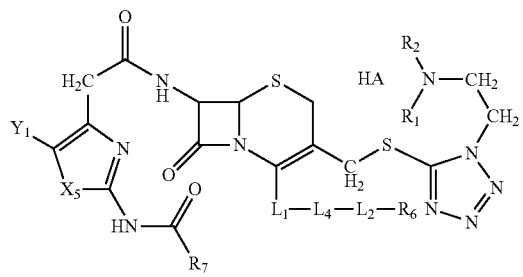
Structure FP-28
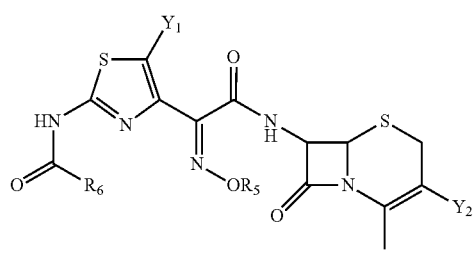
Structure FP-29
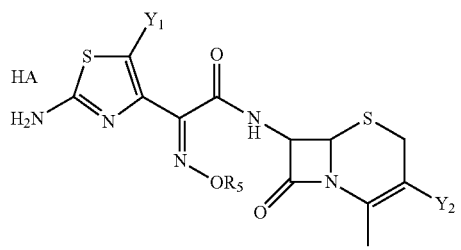
Structure FP-30
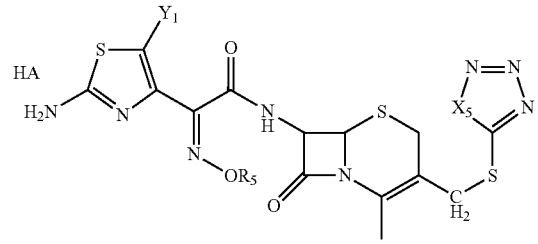
Structure FP-31
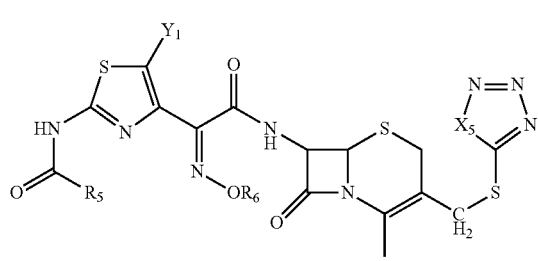
Structure FP-32
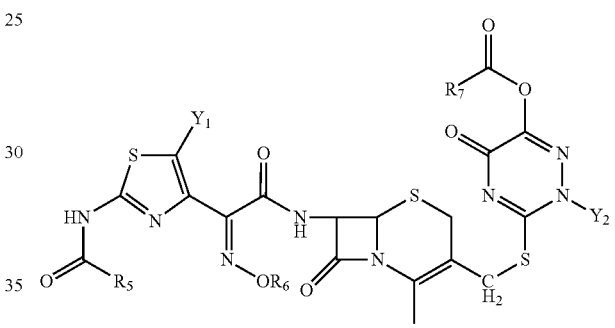
Structure FP-33
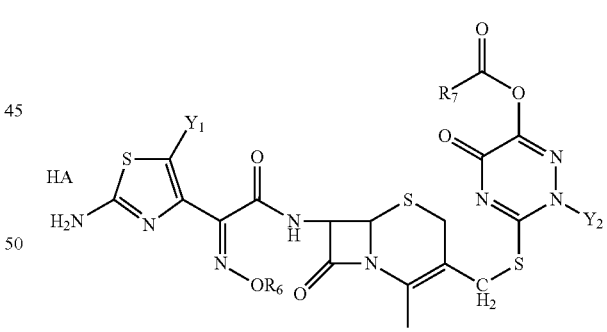
Structure FP-34
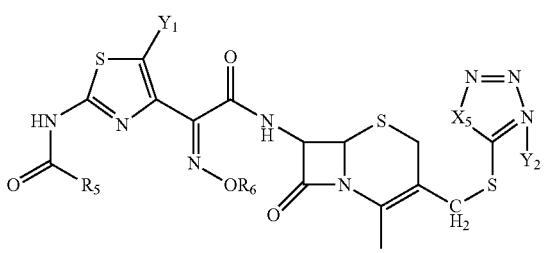

Structure FP-35
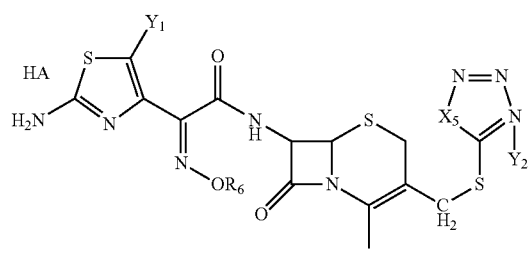
Structure FP-36
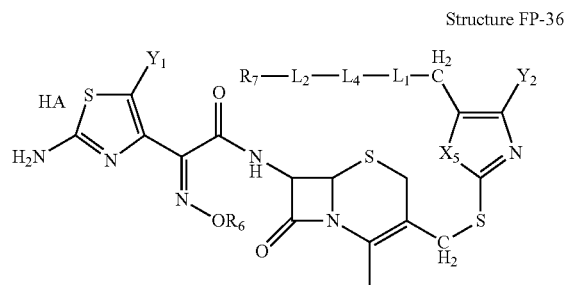
Structure FP-37
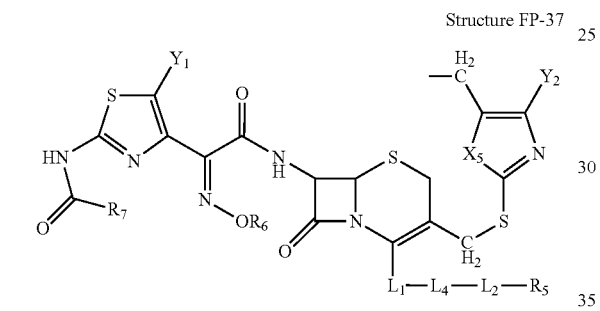
Structure FP-38
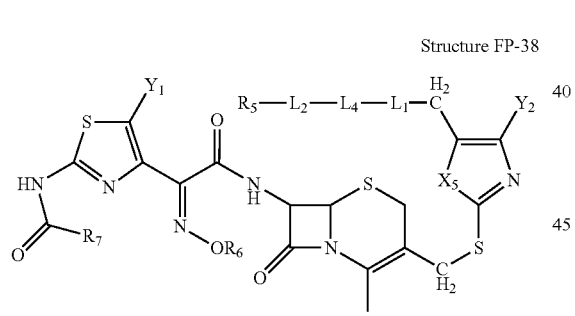
Structure FP-39
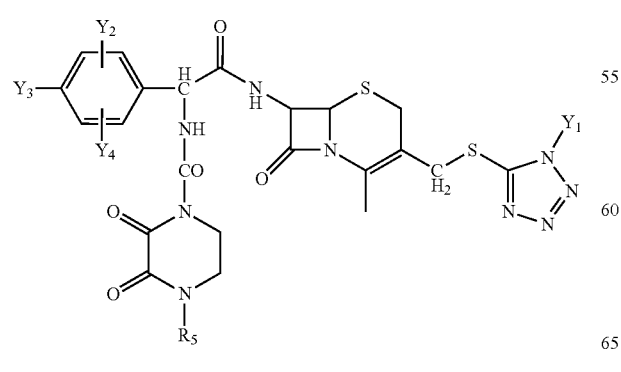
Structure FP-40
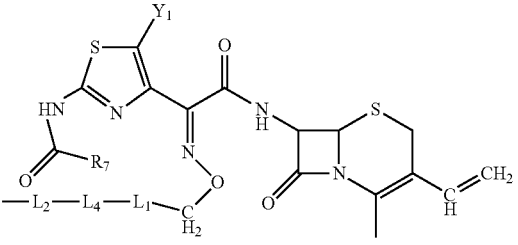
Structure FP-41
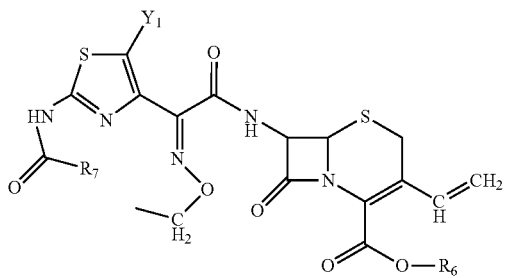
Structure FP-42
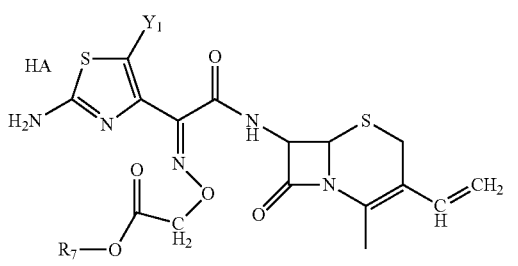
Structure FP-43
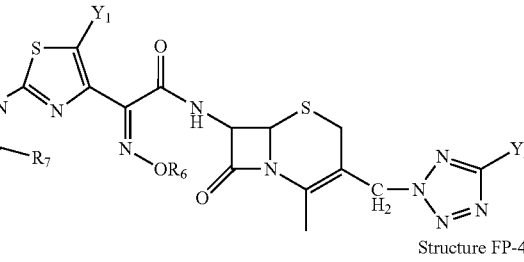
Structure FP-44
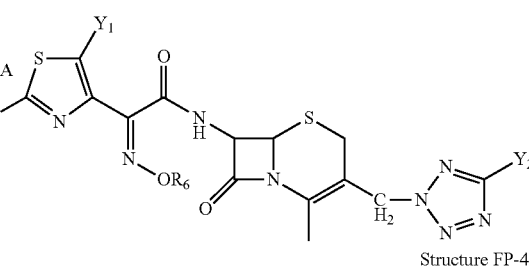
Structure FP-45
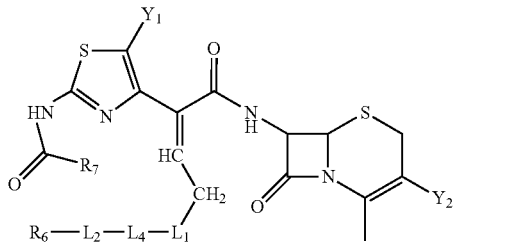

Structure FP-46
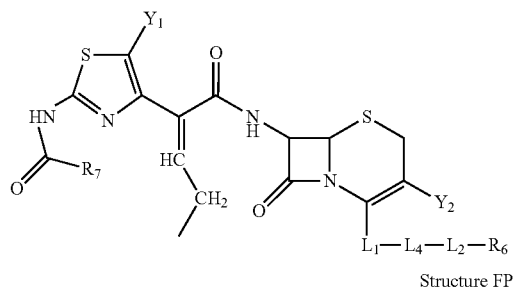
Structure FP-47
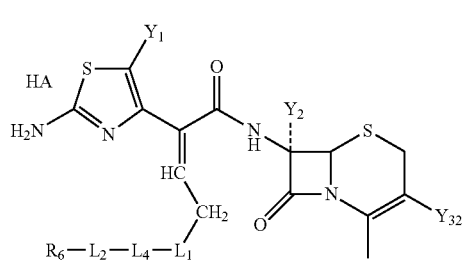
Structure FP-48
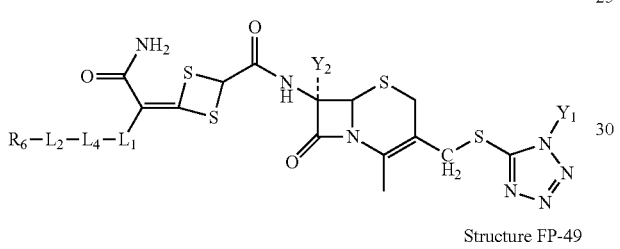
Structure FP-49
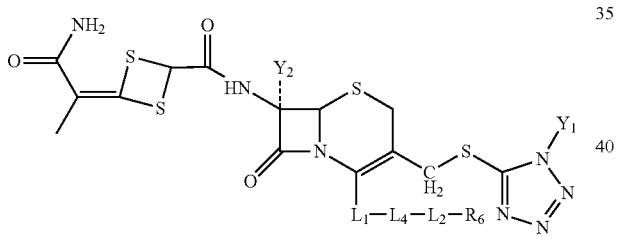
Structure FP-50
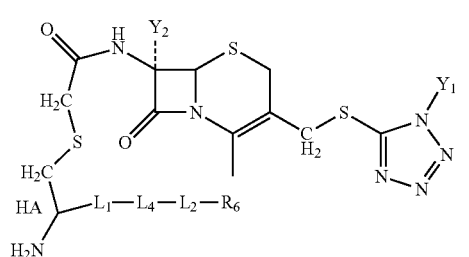
Structure FP-51
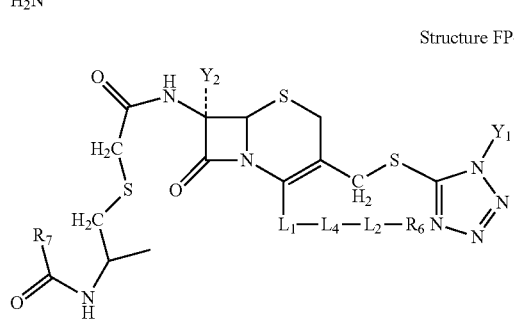
Structure FP-52
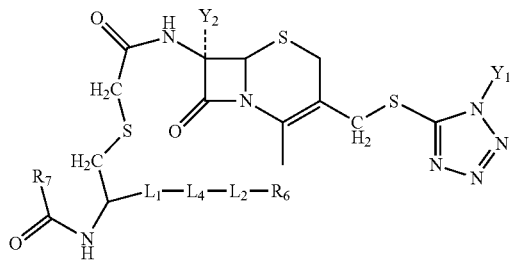
Structure FP-53
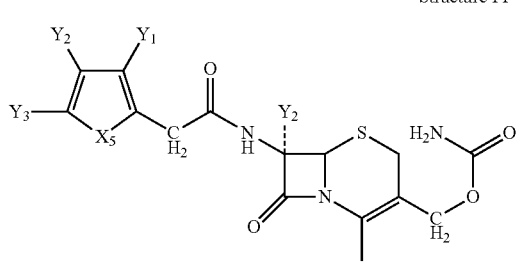
Structure FP-54
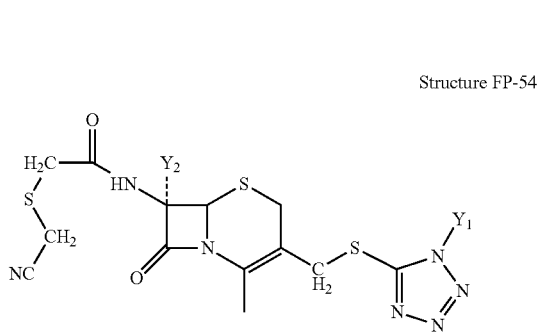
Structure FP-55
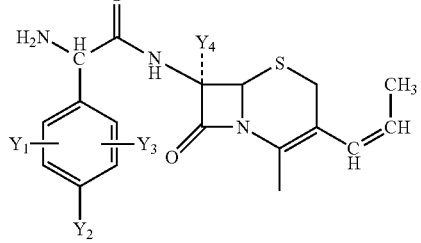
Structure FP-56
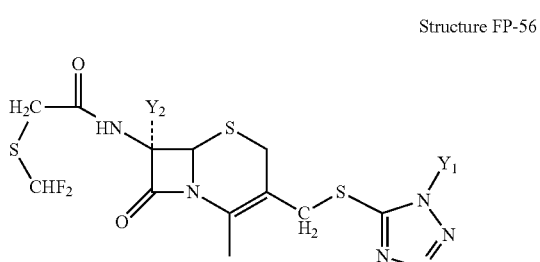

Structure FP-57
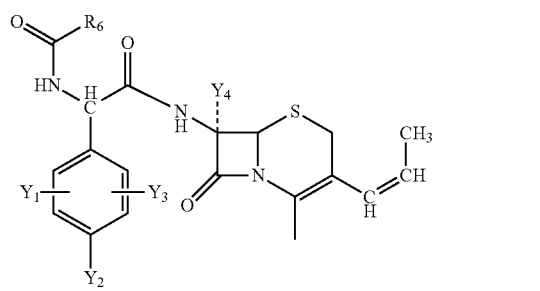
Structure FP-62
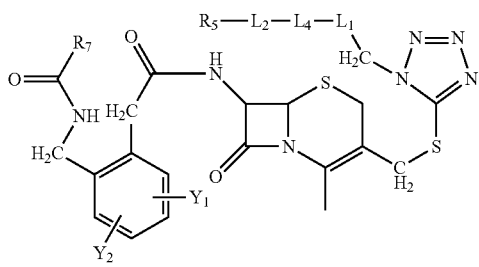
Structure FP-58
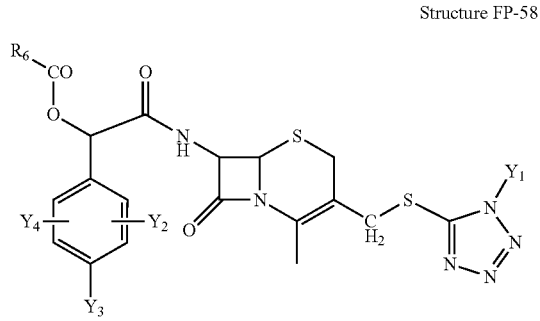
Structure FP-63
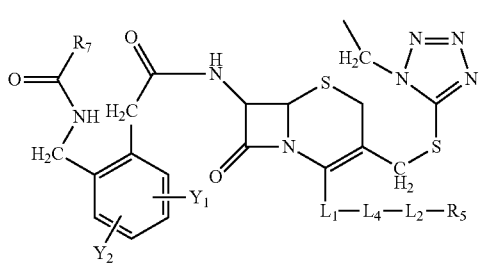
Structure FP-59
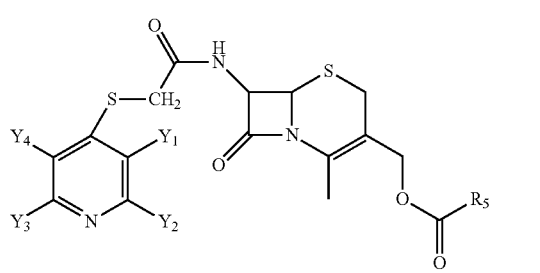
Structure FP-64
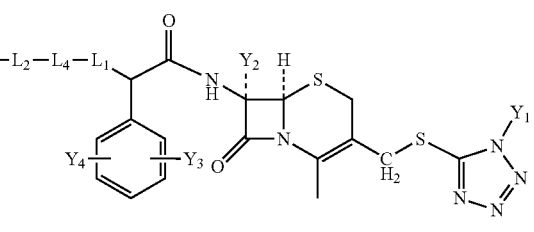
Structure FP-60
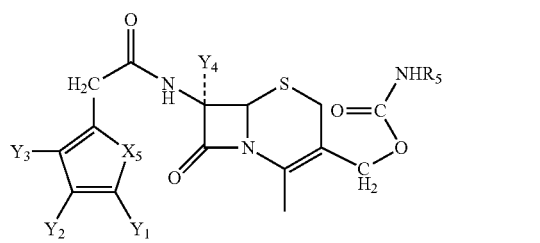
Structure FP-65
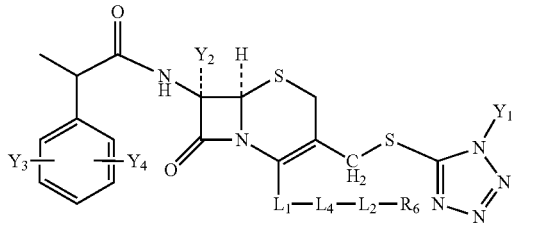
Structure FP-61
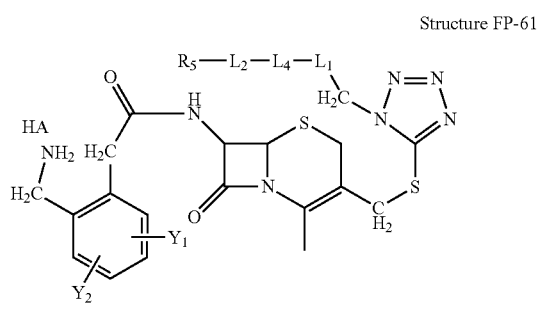
Structure FP-66
Structure FP-67
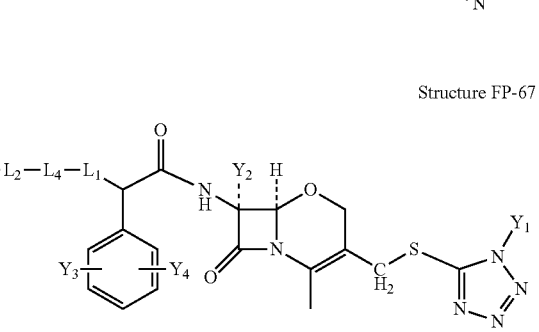

Structure FP-68
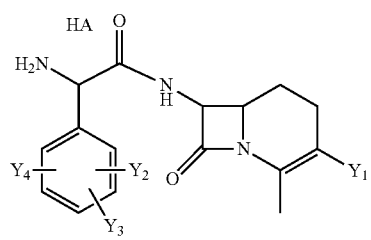
Structure FP-69
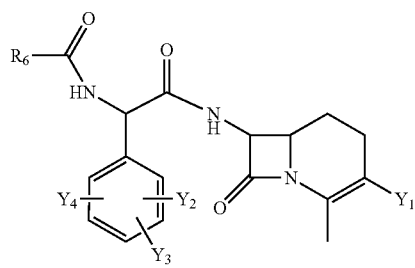
Structure FP-70
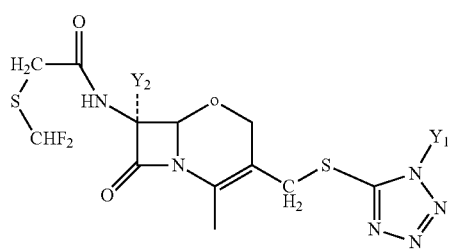
Structure FP-71
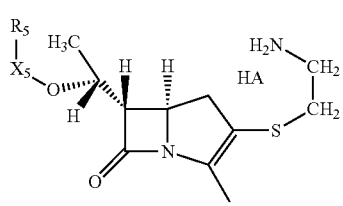
Structure FP-72
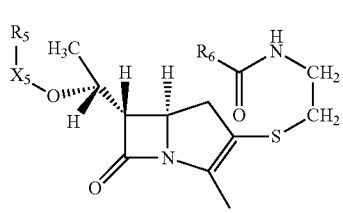
Structure FP-73
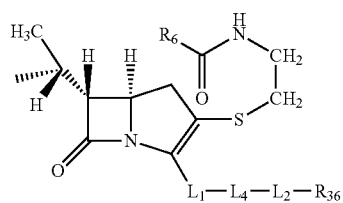
Structure FP-74
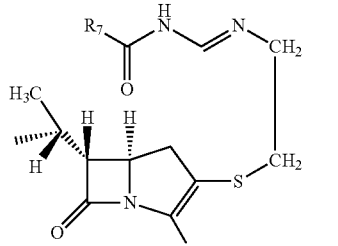
Structure FP-75
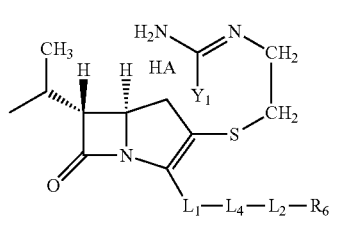
Structure FP-76
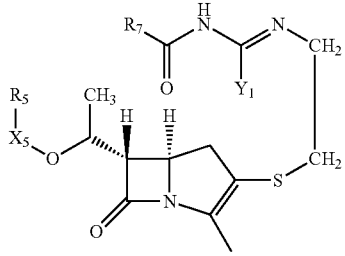
Structure FP-77
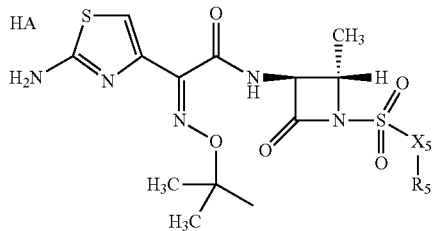
Structure FP-78
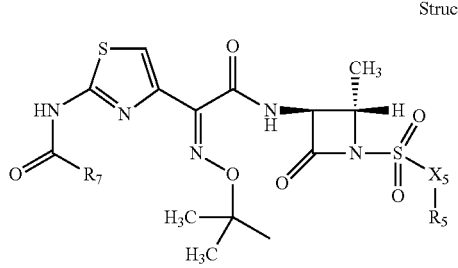
Structure FP-79
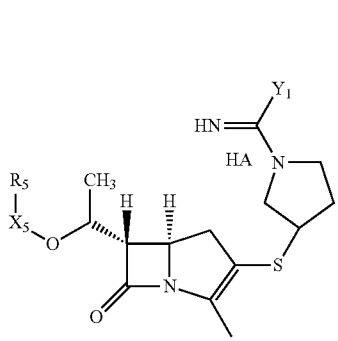

Structure FP-80
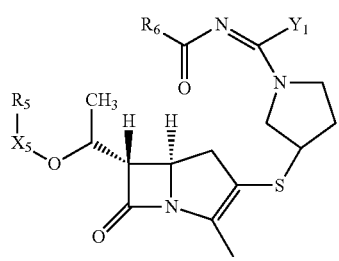
Structure FP-81
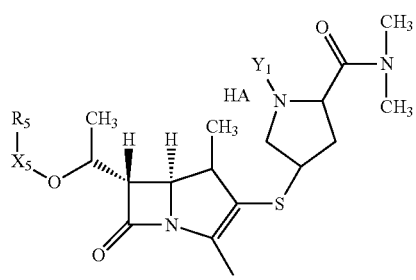
Structure FP-82
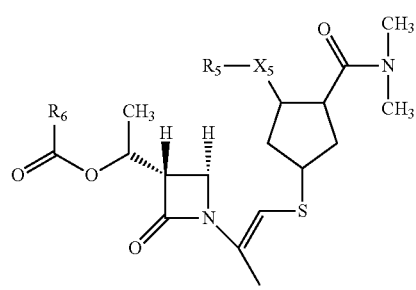
Structure FP-83
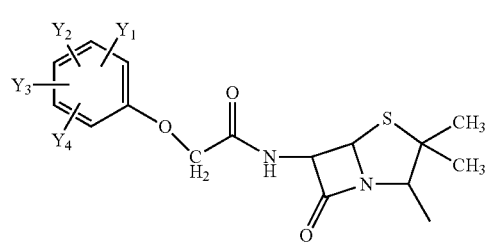
Structure FP-84
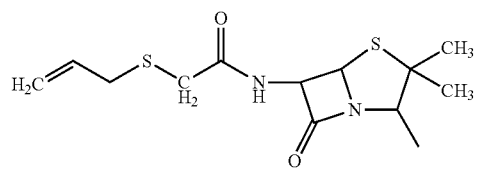
Structure FP-85
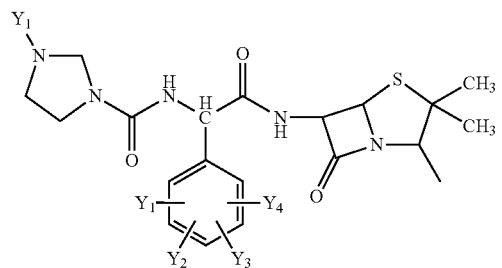
Structure FP-86
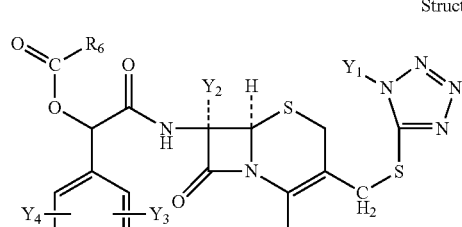
Structure FI-1
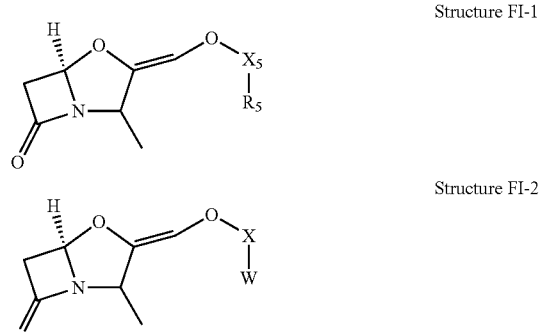
Structure FI-2
Structure FI-3
Structure FI-4
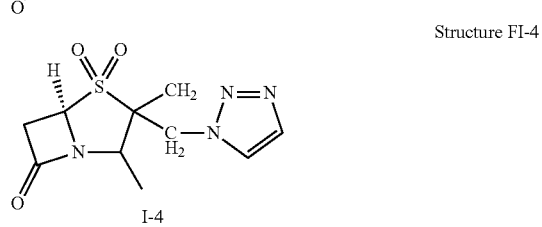
I-4
Structure FI-5
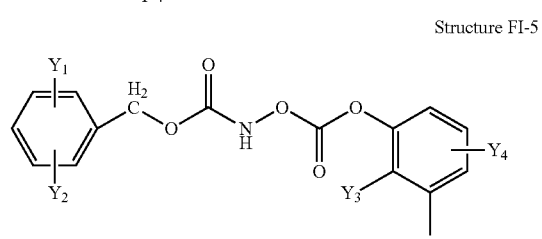
I-5
Structure FI-6
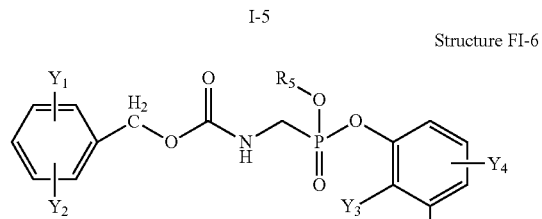
Structure FI-7
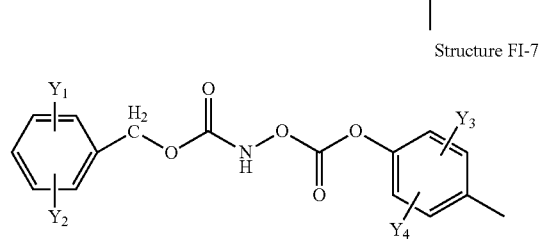

Structure FI-8
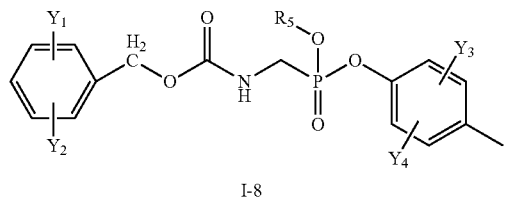
I-8
Structure FI-9
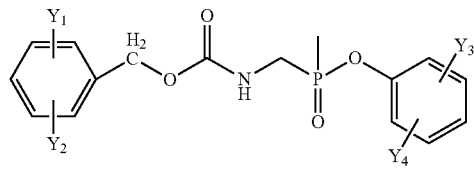
I-9
Structure FI-10
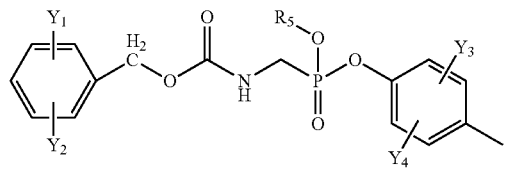
Structure FI-11
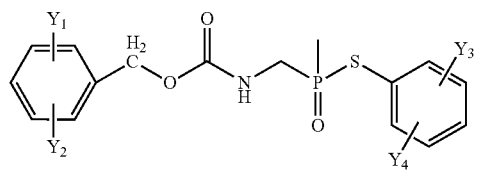
Structure FI-12
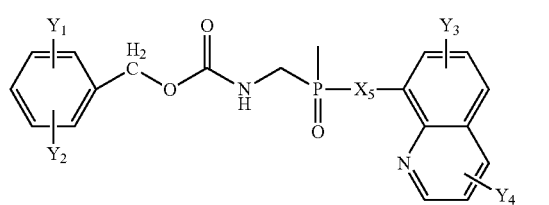
Structure FI-13
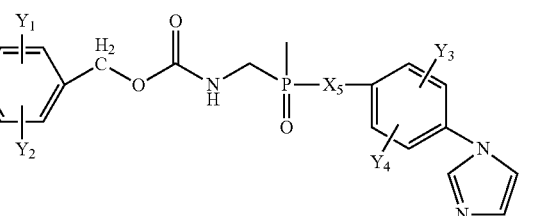
Structure FI-14
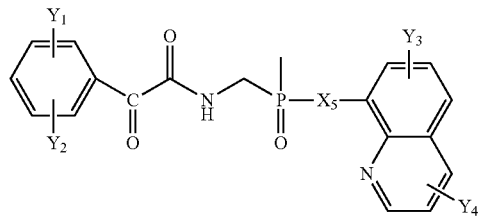
Structure FI-15
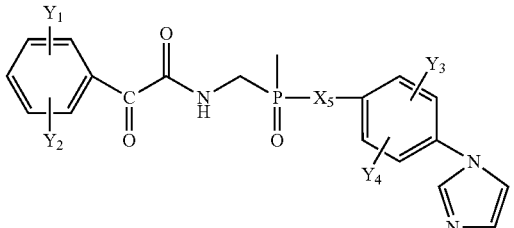
Structure FI-16
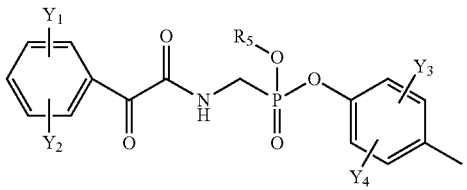
Structure FI-17
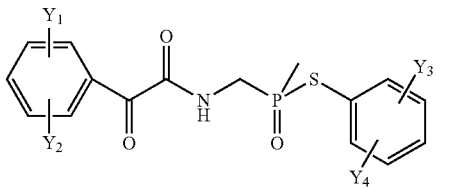
Structure FI-18
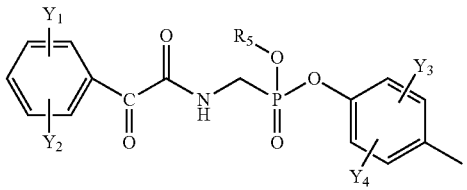
Structure FI-19
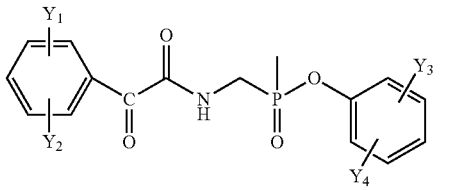
Structure FI-20
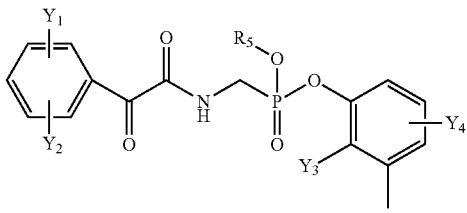
Structure FI-21
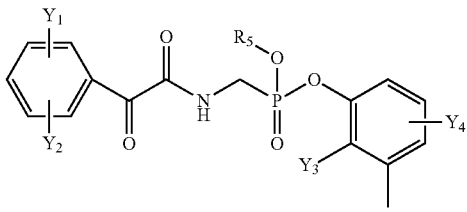

Structure FI-22
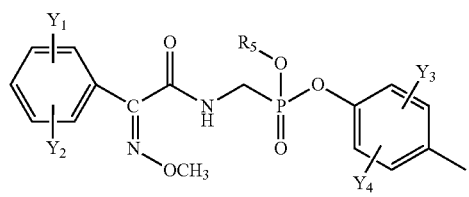
Structure FI-23
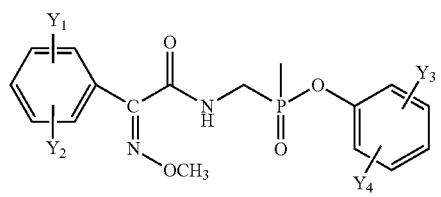
Structure FI-24
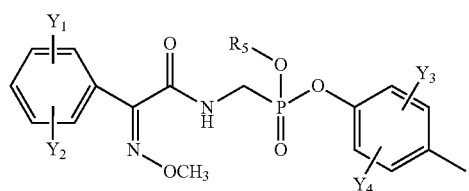
Structure FI-25
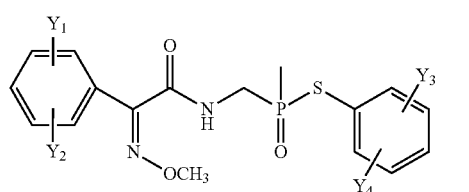
Structure FI-26
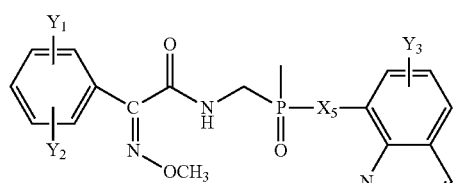
Structure FI-27
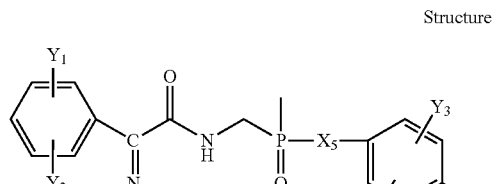
Structure FI-28
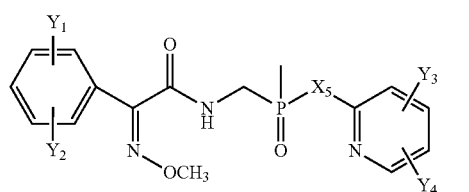
Structure FI-29
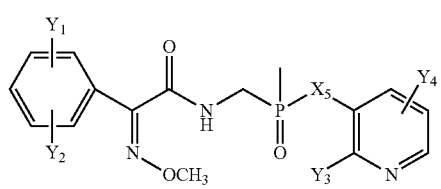
Structure FI-30
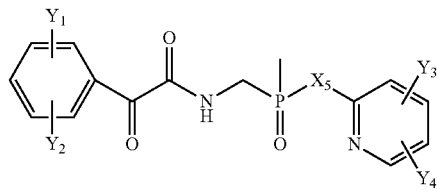
Structure FI-31
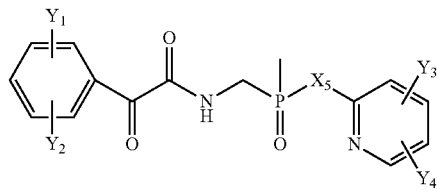
Structure FI-32
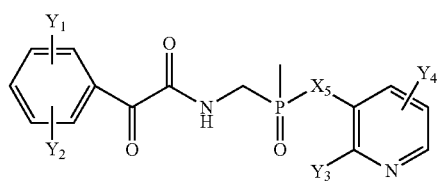
Structure FI-33
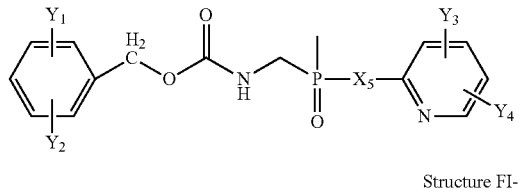
Structure FS-1
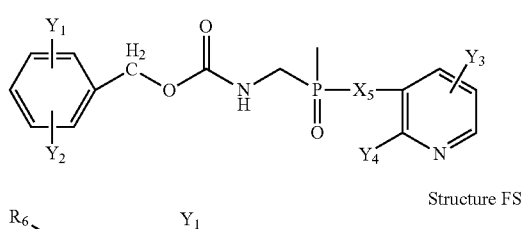
Structure FS-2
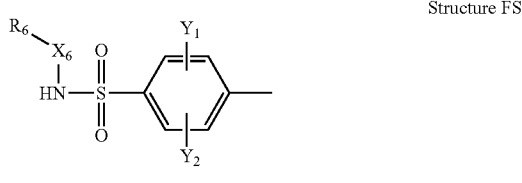
Structure FS-3
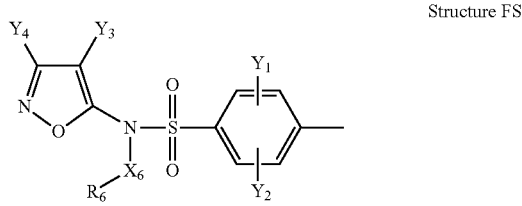

Structure FS-4
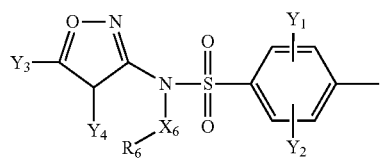
Structure FS-5
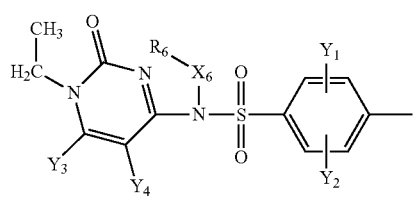
Structure FS-6
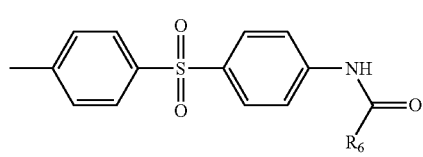
Structure FS-7
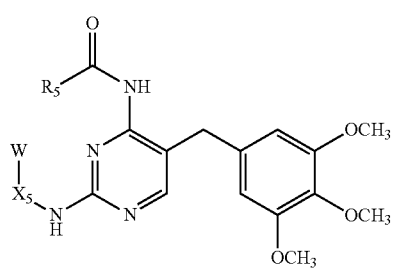
Structure FS-8
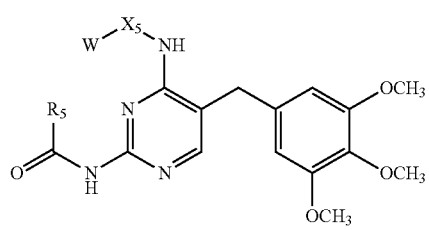
Structure FS-9
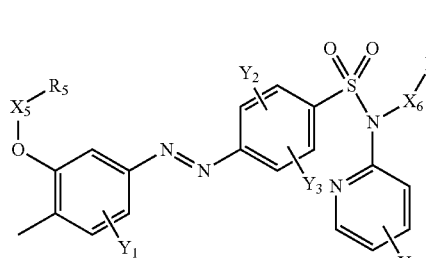
Structure FS-10
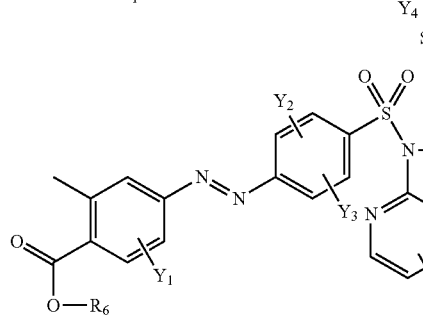
Structure FS-11
Structure FS-12
Structure FS-13
Structure FS-14
Structure FS-15
Structure FS-16
Structure FS-17

Structure FS-18
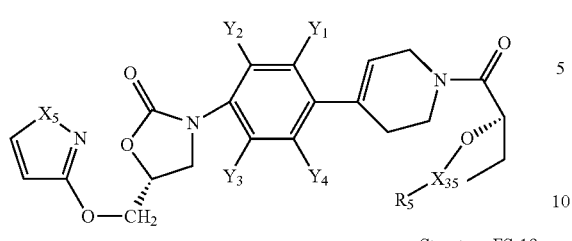
Structure FS-19
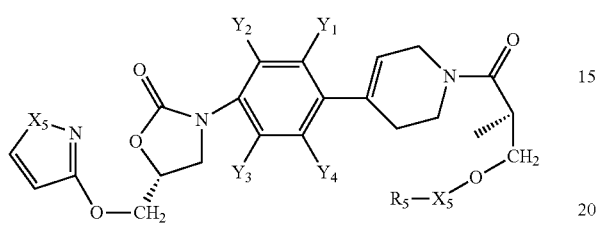
Structure FS-20
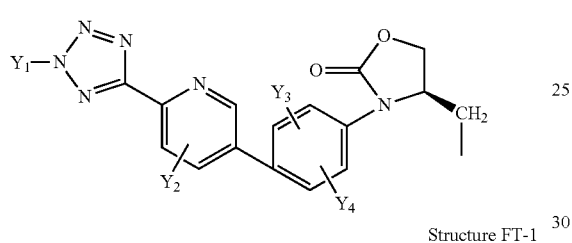
Structure FT-1
Structure FT-2
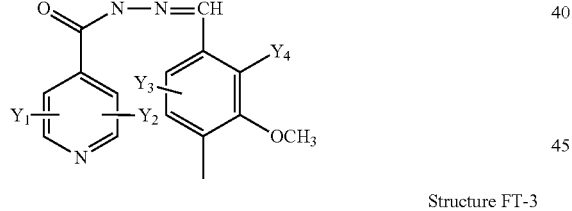
Structure FT-3
Structure FT-4
Structure FT-5
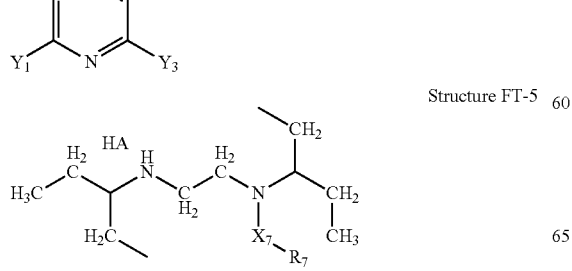
Structure FT-6
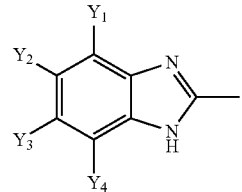
Structure FT-7
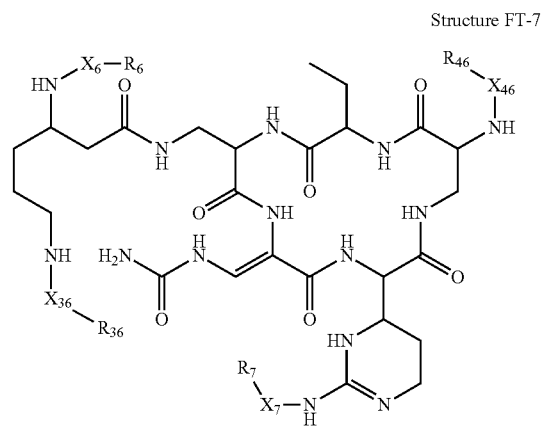
Structure FT-8
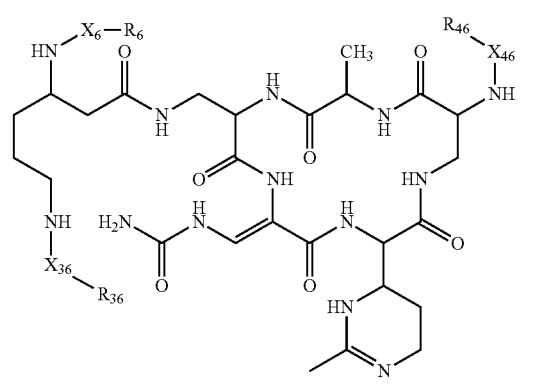
Structure FT-9
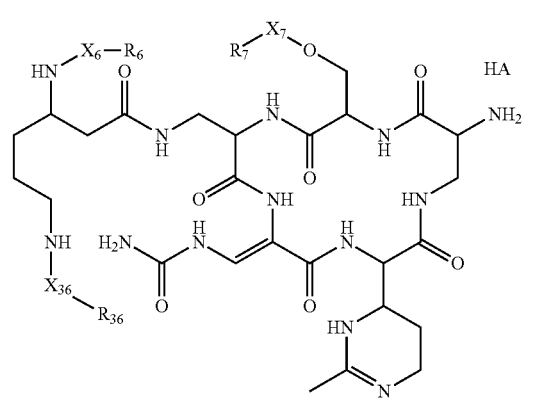

57

-continued

Structure FT-10

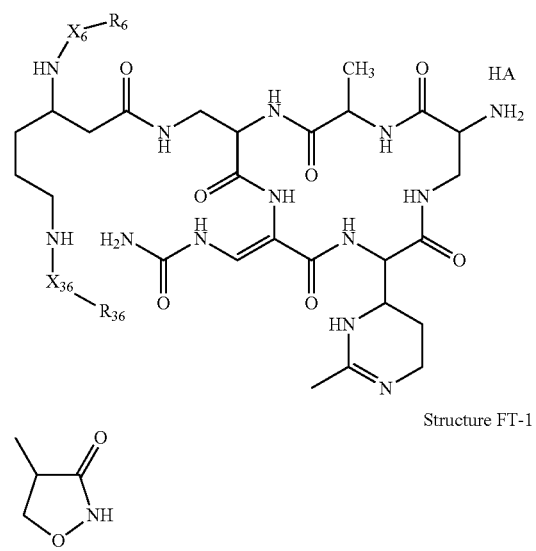

Structure FT-11

Structure FT-12

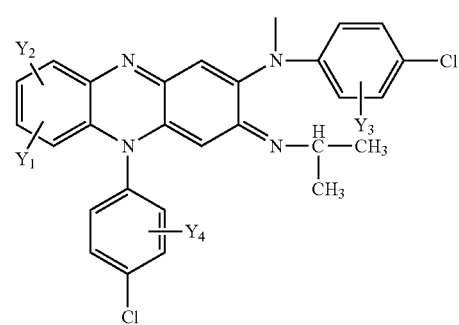

Structure FT-13

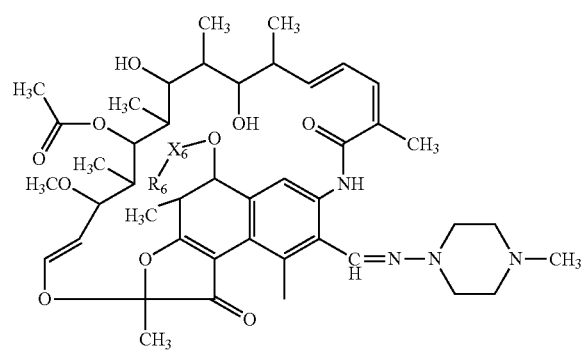

Structure FT-14

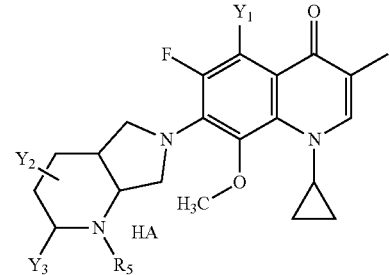

58

-continued

Structure FT-15

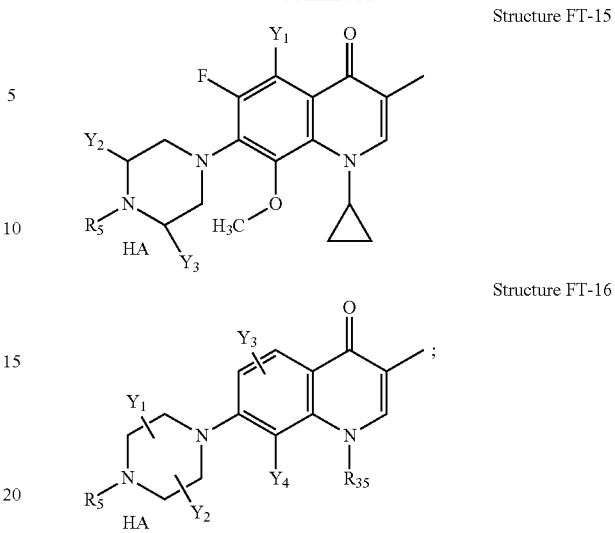

Structure FT-16 including stereoisomers and pharmaceutically acceptable salts thereof, wherein:

n, $R_6$, $R_{36}$, $R_{46}$, $R_7$, $X_5$, $X_{35}$, $Y_1$, $Y_2$, $Y_{31}$, $Y_{32}$, $Y_3$, and $Y_4$ are defined the same as supra;

$L_{31}$ is defined the same as $L_1$ as supra, $L_{32}$ is defined the same as $L_2$ as supra, $L_{34}$ is defined the same as $L_4$ as supra, in certain embodiments, -$L_1$-$L_4$-$L_2$- and -$L_{31}$-$L_{34}$-$L_{32}$- are independently selected from the group consisting of —O—, —X—, —O—X—, —N—X—, —S—X—, —$X_5$—, —O—$X_5$—, —N—$X_5$—, —S—$X_5$—, —NH—C(=O)—, —C(=O)—, —C(=O)—O—, —C(=O)—N—, and C(=O)—X—;

X is selected from the group consisting of nothing, C(=O), OC(=O), $CH_2$, CH, S, NH, $NR_6$, and O;

$X_6$, $X_{36}$ and $X_{46}$ are independently selected from the group consisting of nothing, C(=O), OC(=O), $CH_2$, CH, S, O and $NR_5$; and $X_7$ is selected from the group consisting of nothing, C(=O), OC(=O), $CH_2$, CH, S, O and $NR_5$.

In certain embodiments, a functional unit of a HPP of a antimicrobial and antimicrobial-related compound comprises a moiety having a structure of Structure F-1, Structure FP-1, Structure FP-2, Structure FP-3, Structure FP-4, Structure FP-5, Structure FP-6, Structure FP-7, Structure FP-8, Structure FP-9, Structure FP-10, Structure FP-11, Structure FP-12, Structure FP-13, Structure FP-14, Structure FP-15, Structure FP-16, Structure FP-17, Structure FP-18, Structure FP-19, Structure FP-20, Structure FP-21, Structure FP-22, Structure FP-23, Structure FP-24, Structure FP-25, Structure FP-26, Structure FP-27, Structure FP-28, Structure FP-29, Structure FP-30, Structure FP-31, Structure FP-32, Structure FP-33, Structure FP-34, Structure FP-35, Structure FP-36, Structure FP-37, Structure FP-38, Structure FP-39, Structure FP-40, Structure FP-41, Structure FP-42, Structure FP-43, Structure FP-44, Structure FP-45, Structure FP-46, Structure FP-47, Structure FP-48, Structure FP-49, Structure FP-50, Structure FP-51, Structure FP-52, Structure FP-53, Structure FP-54, Structure FP-55, Structure FP-56, Structure FP-57, Structure FP-58, Structure FP-59, Structure FP-60, Structure FP-61, Structure FP-62, Structure FP-63, Structure FP-64, Structure FP-65, Structure FP-66, Structure FP-67, Structure FP-68, Structure FP-69, Structure FP-70, Structure FP-71, Structure FP-72, Structure FP-73, Structure FP-74, Structure FP-75, Structure FP-76, Structure FP-77, Structure FP-78, Structure FP-79, Structure FP-80, Structure FP-81, Structure FP-82, Structure FP-83, Structure FP-84, Structure FP-85, Structure FP-86, Structure FI-1, Structure FI-2, Structure FI-3, Structure FI-4, Structure FI-5, Structure FI-6, Structure FI-7, Structure FI-8, Structure FI-9, Structure FI-10, Structure FI-11, Structure FI-12, Structure FI-13, Structure FI-14, Structure FI-15, Structure FI-16, Structure FI-17, Structure FI-18, Structure FI-19, Structure FI-20, Structure FI-21, Structure FI-22, Structure FI-23, Structure FI-24, Structure FI-25, Structure FI-26, Structure FI-27, Structure FI-28, Structure FI-29, Structure FI-30, Structure FI-31, Structure FI-32, Structure FI-33, Structure FS-1, Structure FS-2, Structure FS-3, Structure FS-4, Structure FS-5, Structure FS-6, Structure FS-7, Structure FS-8, Structure FS-9, Structure FS-10, Structure FS-11, Structure FS-12, Structure FS-13, Structure FS-14, Structure FS-15, Structure FS-16, Structure FS-17, Structure FS-18, Structure FS-19, Structure FS-20, Structure FT-1, Structure FT-2, Structure FT-3, Structure FT-4, Structure FT-5, Structure FT-6, Structure FT-7, Structure FT-8, Structure FT-9, Structure FT-10, Structure FT-11, Structure FT-12, Structure FT-13, Structure FT-14, Structure FT-15, and Structure FT-16 as defined supra, including stereoisomers and pharmaceutically acceptable salts thereof, wherein:

m=0, 1, 2, 3, 4, 5, 6, 7, 8, 9, 10, 11, 12, 13, 14, 15, 16, 17, 18, 19, 20, . . . ;

n=0, 1, 2, 3, 4, 5, 6, 7, 8, 9, 10, 11, 12, 13, 14, 15, 16, 17, 18, 19, 20, . . . ;

$R_1$ is selected from the group consisting of H, $C_1$-$C_{20}$ alkyl, $C_1$-$C_{20}$ alkyloxyl, $C_1$-$C_{20}$ alkenyl, $C_1$-$C_{20}$ alkynyl, aryl, and heteroaryl;

$R_2$ is selected from the group consisting of H, $C_1$-$C_{20}$ alkyl, $C_1$-$C_{20}$ alkyloxy, $C_1$-$C_{20}$ alkenyl, $C_1$-$C_{20}$ alkynyl, aryl, and heteroaryl residues;

$R_3$ is selected from the group consisting of H, $C_1$-$C_{20}$ alkyl, $C_1$-$C_{20}$ alkyloxy, $C_1$-$C_{20}$ alkenyl, $C_1$-$C_{20}$ alkynyl, aryl and heteroaryl residues;

$R_5$ and $R_{35}$ are independently selected from the group consisting of H, —C(═O)$NH_2$, $CH_2CH_2OR_6$, $CH_2CH_2N(CH_3)_2$, $CH_2CH_2N(CH_2CH_3)_2$, $CH_2CH_2OR_6$, Cl, F, Br, I, $C_1$-$C_{20}$ alkyl, $C_1$-$C_{20}$ cycloalkyl, $C_1$-$C_{20}$ alkyloxyl, $C_1$-$C_{20}$ cycloalkyloxyl, $C_1$-$C_{20}$ alkenyl, $C_1$-$C_{20}$ cycloalkenyl, $C_1$-$C_{20}$ cycloalkynyl, $C_1$-$C_{20}$ alkynyl, aryl, heteroaryl, C(═O)—W, and W;

$R_6$, $R_{36}$ and $R_{46}$ are independently selected from the group consisting of H, F, Cl, Br, I, $Na^+$, $K^+$, C(═O)$R_5$, 2-oxo-1-imidazolidinyl, phenyl, 5-indanyl, 2,3-dihydro-1H-inden-5-yl, 4-hydroxy-1,5-naphthyridin-3-yl, $C_1$-$C_{12}$ lkyl, $C_1$-$C_{12}$ cycloalkyl, $C_1$-$C_{12}$ alkyloxyl, $C_1$-$C_{12}$ cycloalkyloxyl, $C_1$-$C_{12}$ alkenyl, $C_1$-$C_{12}$ cycloalkenyl, $C_1$-$C_{12}$ cycloalkynyl, $C_1$-$C_{12}$ alkynyl, aryl, heteroaryl, C(═O)—W, and W;

$R_7$ and $R_{37}$ are independently selected from the group consisting of H, F, Cl, Br, I, $CH_3NHC$(═O)$CH_2CH(NHR_8)$C(═O), $R_5N$=C(NHR_6)NHC(═O)—, C(═O)$CH_3$, C(═O)$R_6$, PO(OR_5)OR_6, $C_1$-$C_{20}$ alkyl, $C_1$-$C_{20}$ alkyloxyl, $C_1$-$C_{20}$ alkenyl, $C_1$-$C_{20}$ alkynyl, aryl, heteroaryl, C(═O)—W, and W;

$R_8$ and $R_{38}$ are independently selected from the group consisting of H, F, Cl, Br, I, $CH_3$, $C_2H_5$, $CF_3$, $CH_2CH_2F$, $CH_2CH_2Cl$, $CH_2CH_2Br$, $CH_2CH_2I$, $CH_2CHF_2$, $CH_2CF_3$, $CH_2F$, $CH_2Cl$, $CH_2Br$, $CH_2I$, $CH_2NR_6R_7$, $CH(NHR_7)CH_2C$(═O)$NH_2$, $C_3H_7$, $C_4H_9$, $C_5H_{11}$, $R_6$, C(═O)$R_6$, C(═O)$NH_2$, $CH_2C$(═O)$NH_2$, $CH_2OC$(═O)$NH_2$, PO(OR_5)OR_6, C(CH_3)_2C(═O)OR_6, CH(CH_3)C(═O)OR_6, $CH_2C$(═O)$OR_6$, C(═O)—W;

$X_2$ is selected from the group consisting of nothing, H, $CH_2(CH_2)_nOR_8$, Cl, F, Br, I, $NO_2$, CN, $CF_3$, $C_2F_5$, $C_3F_7$, $OCF_3$, $OC_2F_5$, $NH_2$, $NHR_6$, $CH_3$, $C_2H_5$, $R_6$, C(═O)$NH_2$, $CH_2OC$(═O)$NH_2$, $CH_2C$(═O)$OR_5$, $CH_2(CH_2)_nN(CH_3)_2$, $CH_2(CH_2)_nSO_3R_5$, $C_{1-8}$ alkyl, $C_{1-8}$ alkylthio, $C_{1-8}$ alkylamino, and $C_{1-8}$ alkyloxyl;

$X_3$ is selected from the group consisting of nothing, H, $N_3$, $SO_3W$, F, Cl, Br, OH, $OCH_3$, $OR_6$, $CH_3$, $R_6$, C(═O)OW, OW, and I;

$X_4$ is selected from the group consisting of nothing, N, CH, and $CY_1$;

$X_5$ and $X_{35}$ are independently selected from the group consisting of nothing, C(═O), OC(═O), $CH_2$, CH, S, O and $NR_5$;

each $Y_1$, $Y_{31}$, $Y_2$, $Y_{32}$, $Y_3$, and $Y_4$ are independently selected from the group consisting of H, OH, OW, OC(═C)W, OC(═O)$CH_3$, $CH_3$, $C_2H_5$, $C_3H_7$, $C_4H_9$, $SO_3R_6$, $CH_2OR_6$, $CH_2OC$(═O)$R_6$, $CH_2C$(═O)$OR_8$, $OCH_3$, $OC_2H_5$, $CH_3SO_2$, $R_6SO_2$, $R_6SO_3OR_6$, $CH_3SO_3$, $R_6SO_3$, $NO_2$, CN, $CF_3$, $OCF_3$, CH═CHC(═O)NHCH_2C(═O)OW, $CH_2(CH_2)_nNR_5R_6$, $CH_2(CH_2)_nOR_6$, CH(C(═O)$NH_2$)NHR_6, $CH_2C$(═O)$NH_2$, F, Br, I, and Cl;

Z, AA, HA, R, $R_s$, Y, $R_{11}$-$R_{16}$, X, $L_1$, $L_2$, $L_4$, $L_{31}$, $L_{32}$, $L_{34}$ and W are defined the same as supra; and any $CH_2$ groups may be replaced with O, S, $NR_6$ or any other pharmaceutically acceptable groups.

As used herein, the term "pharmaceutically acceptable salt" means those salts of compounds of the invention that are safe for application in a subject. Pharmaceutically acceptable salts include salts of acidic or basic groups present in compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,11-methylene-bis-(2-hydroxy-3-naphthoate)) salts. Certain compounds of the invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see BERGE ET AL., 66 J. PHARM. SCI. 1-19 (1 977), incorporated herein by reference.

As used herein, unless specified otherwise, the term "alkyl" means a branched or unbranched, saturated or unsaturated, monovalent or multivalent hydrocarbon group, including saturated alkyl groups, alkenyl groups and alkynyl groups. Examples of alkyl include, but are not limited to, methyl, ethyl, propyl, isopropyl, butyl, isobutyl, t-butyl, pentyl, hexyl, heptyl, octyl, nonyl, decyl, undecyl, dodecyl, ethenyl, propenyl, butenyl, isobutenyl, pentenyl, hexenyl, heptenyl, octenyl, nonenyl, decenyl, undecenyl, dodecenyl, ethynyl, propynyl, butynyl, isobutynyl, pentynyl, hexynyl, heptynyl, octynyl, nonynyl, decynyl, undecynyl, dodecynyl, methylene, ethylene, propylene, isopropylene, butylene, isobutylene, t-butylene, pentylene, hexylene, heptylene, octylene, nonylene, decylene, undecylene and dodecylene. In certain embodiments, the hydrocarbon group contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "cycloalkyl" means an alkyl which contains at least one ring and no aromatic rings. Examples of cycloalkyl include, but are not limited to, cyclopropyl, cyclobutyl, cyclopentyl, cyclohexyl, cycloheptyl, cyclooctyl, cyclononyl, cyclodecyl, cycloundecyl and cyclododecyl. In certain embodiments, the hydrocarbon chain contains 1 to 30 carbons. In certain embodiments, the hydrocarbon group contains 1 to 20 carbons. In certain embodiments, the hydrocarbon group contains 1 to 12 carbons.

As used herein, unless specified otherwise, the term "heterocycloalkyl" means a cycloalkyl wherein at least one ring atom is a non-carbon atom. Examples of the non-carbon ring atom include, but are not limited to, S, O and N.

As used herein, unless specified otherwise, the term "alkoxyl" means an alkyl, cycloalkyl or heterocycloalkyl, which contains one or more oxygen atoms. Examples of alkoxyl include, but are not limited to, —CH$_2$—OH, —OCH$_3$, —O—R$_e$, —R$_e$—OH, —R$_{e1}$—O—R$_{e2}$—, wherein R$_e$, R$_{e1}$ and R$_{e2}$ can be the same or different alkyl, cycloalkyl or heterocycloalkyl.

As used herein, unless specified otherwise, the term "alkyl halide" means an alkyl, cycloalkyl or heterocycloalkyl, which contains one or more halogen atoms, wherein the halogen atoms can be the same or different. The term "halogen" means fluorine, chlorine, bromine or iodine. Examples of alkyl halide include, but are not limited to, —R$_e$—F, —R$_e$—Cl, —R$_e$—Br, —R$_e$—I, —R$_e$(F)—, —R$_e$(Cl)—, —R$_e$(Br)— and —R$_e$(I)—, wherein R$_e$ is an alkyl, cycloalkyl or heterocycloalkyl.

As used herein, unless specified otherwise, the term "alkylthio" means an alkyl, cycloalkyl or heterocycloalkyl, which contains one or more sulfur atoms. Examples of alkylthio include, but are not limited to, —CH$_2$—SH, —SCH$_3$, —S—R$_e$, —R$_e$—SH, —R$_{e1}$—S—R$_{e2}$—, wherein R$_e$, R$_{e1}$ and R$_{e2}$ are the same or different alkyl, cycloalkyl or heterocycloalkyl.

As used herein, unless specified otherwise, the term "alkylamino" means an alkyl, cycloalkyl or heterocycloalkyl, which contains one or more nitrogen atoms. Examples of alkylamino include, but are not limited to, —CH$_2$—NH, —NCH$_3$, —N(R$_{e1}$)—R$_{e2}$, —N—R$_e$, —R$_e$—NH$_2$, —R$_{e1}$—N—R$_{e2}$ and —R$_e$—N(R$_{e1}$)—R$_{e2}$ wherein R$_e$, R$_{e1}$ and R$_{e2}$ are the same or different alkyl, cycloalkyl or heterocycloalkyl.

As used herein, unless specified otherwise, the term "alkylcarbonyl" means an alkyl, cycloalkyl or heterocycloalkyl, which contains one or more carbonyl groups. Examples of alkylcarbonyl group include, but are not limited to, aldehyde group (—R$_e$—C(O)—H), ketone group (—R$_e$—C(O)—R$_{e1}$), carboxylic acid group (R$_e$—C(=O)OH), ester group (—R$_e$—C(=O)O—R$_{e1}$), carboxamide, (—R$_e$—C(=O)O—N(R$_{e1}$)R$_{e2}$), enone group (—R$_e$—C(O)—C(R$_{e1}$)=C(R$_{e2}$)R$_{e3}$), acyl halide group (—R$_e$—C(O)—X$_h$) and acid anhydride group (—R$_e$—C(O)—O—C(O)—R$_{e1}$), wherein R$_e$, R$_{e1}$, R$_{e2}$ and R$_{e3}$ are the same or different alkyl, cycloalkyl, or heterocycloalkyl; and X$_h$ is a halogen.

As used herein, unless specified otherwise, the term "perfluoroalkyl" means an alkyl, cycloalkyl or heterocycloalkyl, which contains one or more fluoro group, including, without limitation, perfluoromethyl, perfluoroethyl, perfluoropropyl.

As used herein, unless specified otherwise, the term "aryl" means a chemical structure comprising one or more aromatic rings. In certain embodiments, the ring atoms are all carbon. In certain embodiments, one or more ring atoms are non-carbon, e.g. oxygen, nitrogen, or sulfur ("heteroaryl"). Examples of aryl include, without limitation, phenyl, benzyl, naphthalenyl, anthracenyl, pyridyl, quinoyl, isoquinoyl, pyrazinyl, quinoxalinyl, acridinyl, pyrimidinyl, quinazolinyl, pyridazinyl, cinnolinyl, imidazolyl, benzimidazolyl, purinyl, indolyl, furanyl, benzofuranyl, isobenzofuranyl, pyrrolyl, indolyl, isoindolyl, thiophenyl, benzothiophenyl, pyrazolyl, indazolyl, oxazolyl, benzoxazolyl, isoxazolyl, benzisoxazolyl, thiaxolyl, quanidino and benzothiazolyl.

In certain embodiments, a transportational unit of a HPP comprises a protonatable amine group that is capable of facilitating the transportation or crossing of the HPP through one or more biological barriers (e.g., >about 20 times, >about 50 times, >about 100 times, >about 300 times, >about 500 times, >about 1,000 times faster than the parent drug). In certain embodiments, the protonatable amine group is substantially protonated at a physiological pH. In certain embodiments, the amine group can be reversibly protonated. In certain embodiments, a transportational unit may or may not be cleaved from the functional unit after the penetration of HPP through one or more biological barriers. In certain embodiments, a functional unit may also contain one or more transportational units, especially for antimicrobials and antimicrobial-related compounds that have at least a free amino group.

In certain embodiments, the protonatable amine group is selected from the group consisting of pharmaceutically acceptable substituted and unsubstituted primary amine groups, pharmaceutically acceptable substituted and unsubstituted secondary amine groups, and pharmaceutically acceptable substituted and unsubstituted tertiary amine groups.

In certain embodiments, the protonatable amine group is selected from the group consisting of Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18 as defined supra, including stereoisomers and pharmaceutically acceptable salts thereof.

In certain embodiments, a linker covalently linking a functional unit and a transportational unit of a HPP comprises a bond that is capable of being cleaved after the HPP penetrates across one or more BBs. The cleavable bond comprises, for example, a covalent bond, an ether, thioether, amide, ester, thioester, carbonate, carbamate, phosphate or oxime bond.

In certain embodiments, a HPP of a antimicrobials and antimicrobial-related compound has the following Structure L-1:

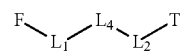

Structure L-1 including stereoisomers and pharmaceutically acceptable salts thereof, wherein:

F is a functional unit of a HPP of an antimicrobial or antimicrobial-related compound. Examples of F include Structure F-1, Structure FP-1, Structure FP-2, Structure FP-3, Structure FP-4, Structure FP-5, Structure FP-6, Structure FP-7, Structure FP-8, Structure FP-9, Structure FP-10, Structure FP-11, Structure FP-12, Structure FP-13, Structure FP-14, Structure FP-15, Structure FP-16, Structure FP-17, Structure FP-18, Structure FP-19, Structure FP-20, Structure FP-21, Structure FP-22, Structure FP-23, Structure FP-24, Structure FP-25, Structure FP-26, Structure FP-27, Structure FP-28, Structure FP-29, Structure FP-30, Structure FP-31, Structure FP-32, Structure FP-33, Structure FP-34, Structure FP-35, Structure FP-36, Structure FP-37, Structure FP-38, Structure FP-39, Structure FP-40, Structure FP-41, Structure FP-42, Structure FP-43, Structure FP-44, Structure FP-45, Structure FP-46, Structure FP-47, Structure FP-48, Structure FP-49, Structure FP-50, Structure FP-51, Structure FP-52, Structure FP-53, Structure FP-54, Structure FP-55, Structure FP-56, Structure FP-57, Structure FP-58, Structure FP-59, Structure FP-60, Structure FP-61, Structure FP-62, Structure FP-63, Structure FP-64, Structure FP-65, Structure FP-66, Structure FP-67, Structure FP-68, Structure FP-69, Structure FP-70, Structure FP-71, Structure FP-72, Structure FP-73, Structure FP-74, Structure FP-75, Structure FP-76, Structure FP-77, Structure FP-78, Structure FP-79, Structure FP-80, Structure FP-81, Structure FP-82, Structure FP-83, Structure FP-84, Structure FP-85, Structure FP-86, Structure FI-1, Structure FI-2, Structure FI-3, Structure FI-4, Structure FI-5, Structure FI-6, Structure FI-7, Structure FI-8, Structure FI-9, Structure FI-10, Structure FI-11, Structure FI-12, Structure FI-13, Structure FI-14, Structure FI-15, Structure FI-16, Structure FI-17, Structure FI-18, Structure FI-19, Structure FI-20, Structure FI-21, Structure FI-22, Structure FI-23, Structure FI-24, Structure FI-25, Structure FI-26, Structure FI-27, Structure FI-28, Structure FI-29, Structure FI-30, Structure FI-31, Structure FI-32, Structure FI-33, Structure FS-1, Structure FS-2, Structure FS-3, Structure FS-4, Structure FS-5, Structure FS-6, Structure FS-7, Structure FS-8, Structure FS-9, Structure FS-10, Structure FS-11, Structure FS-12, Structure FS-13, Structure FS-14, Structure FS-15, Structure FS-16, Structure FS-17, Structure FS-18, Structure FS-19, Structure FS-20, Structure FT-1, Structure FT-2, Structure FT-3, Structure FT-4, Structure FT-5, Structure FT-6, Structure FT-7, Structure FT-8, Structure FT-9, Structure FT-10, Structure FT-11, Structure FT-12, Structure FT-13, Structure FT-14, Structure FT-15, and Structure FT-16 as defined supra;

T is a transportational unit of a HPP of an antimicrobial or antimicrobial-related compound. For example, T is selected from the group consisting of Structure W-1, Structure W-2, Structure W-3, Structure W-4, Structure W-5, Structure W-6, Structure W-7, Structure W-8, Structure W-9, Structure W-10, Structure W-11, Structure W-12, Structure W-13, Structure W-14, Structure W-15, Structure W-16, Structure W-17 and Structure W-18 as defined supra; and $L_1$, $L_{31}$, $L_2$, $L_{32}$, $L_4$, and $L_{34}$ are defined the same as supra, in certain embodiments, -$L_1$-$L_4$-$L_2$- and -$L_{31}$-$L_{34}$-$L_{32}$- are independently selected from the group consisting of —O—, —X—, —O—X—, —N—X—, —S—X—, —$X_5$—, —O—$X_5$—, —N—$X_5$—, —S—$X_5$—, —O—$X_7$—, —O—C(=O)—, —NH—C(=O)—, —C(=O)—, —C(=O)—O—, —C(=O)—N—, and C(=O)—X— wherein X, $X_5$ and $X_7$ are defined the same as supra.

In certain embodiments, a HPP or HPC of antimicrobial or antimicrobial-related compound comprises a structure selected from the group consisting of Structure P-1, Structure P-2, Structure P-3, Structure P-4, Structure P-5, Structure P-6, Structure P-7, Structure P-8, Structure P-9, Structure P-10, Structure P-11, Structure P-12, Structure P-13, Structure P-14, Structure P-15, Structure P-16, Structure P-17, Structure P-18, Structure P-19, Structure P-20, Structure P-21, Structure P-22, Structure P-23, Structure P-24, Structure P-25, Structure P-26, Structure P-27, Structure P-28, Structure P-29, Structure P-30, Structure P-31, Structure P-32, Structure P-33, Structure P-34, Structure P-35, Structure P-36, Structure P-37, Structure P-38, Structure P-39, Structure P-40, Structure P-41, Structure P-42, Structure P-43, Structure P-44, Structure P-45, Structure P-46, Structure P-47, Structure P-48, Structure P-49, Structure P-50, Structure P-51, Structure P-52, Structure P-53, Structure P-54, Structure P-55, Structure P-56, Structure P-57, Structure P-58, Structure P-59, Structure P-60, Structure P-61, Structure P-62, Structure P-63, Structure P-64, Structure P-65, Structure P-66, Structure P-67, Structure P-68, Structure P-69, Structure P-70, Structure P-71, Structure P-72, Structure P-73, Structure P-74, Structure P-75, Structure P-76, Structure P-77, Structure P-78, Structure P-79, Structure P-80, Structure P-81, Structure P-82, Structure P-83, Structure P-84, Structure P-85, Structure P-86, Structure I-1, Structure I-2, Structure I-3, Structure I-4, Structure I-5, Structure I-6, Structure I-7, Structure I-8, Structure I-9, Structure I-10, Structure I-11, Structure I-12, Structure I-13, Structure I-14, Structure I-15, Structure I-16, Structure I-17, Structure I-18, Structure I-19, Structure I-20, Structure I-21, Structure I-22, Structure I-23, Structure I-24, Structure I-25, Structure I-26, Structure I-27, Structure I-28, Structure I-29, Structure I-30, Structure I-31, Structure I-32, Structure I-33, Structure S-1, Structure S-2, Structure S-3, Structure S-4, Structure S-5, Structure S-6, Structure S-7, Structure S-8, Structure S-9, Structure S-10, Structure S-11, Structure S-12, Structure S-13, Structure S-14, Structure S-15, Structure S-16, Structure S-17, Structure S-18, Structure S-19, Structure S-20, Structure T-1, Structure T-2, Structure T-3, Structure T-4, Structure T-5, Structure T-6, Structure T-7, Structure T-8, Structure T-9, Structure T-10, Structure T-11, Structure T-12, Structure T-13, Structure T-14, Structure T-15, and Structure T-16:

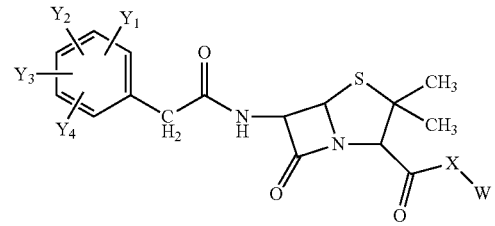

Structure P-1

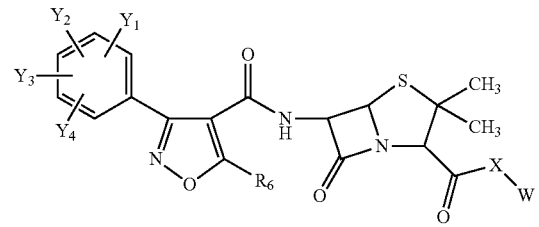

Structure P-2

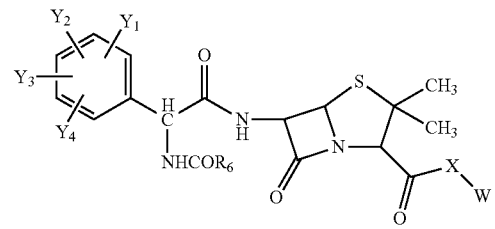

Structure P-3

Structure P-4
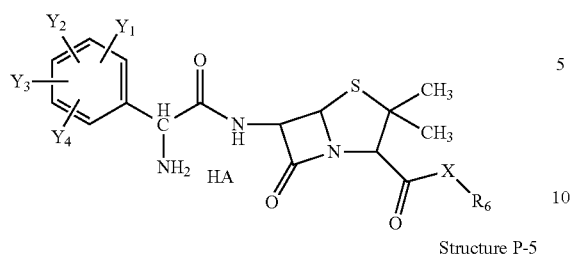
Structure P-5
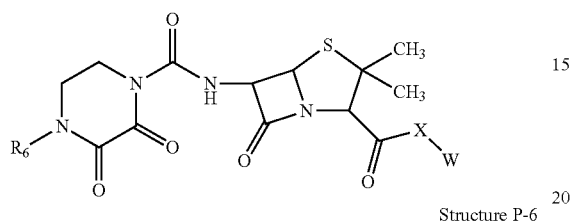
Structure P-6
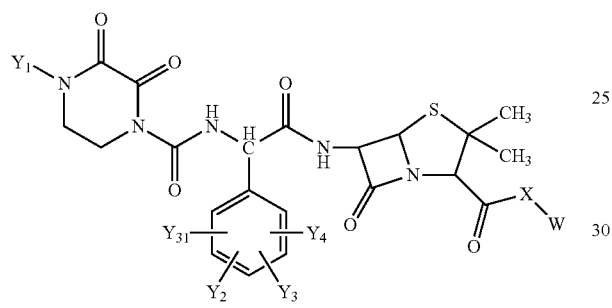
Structure P-7
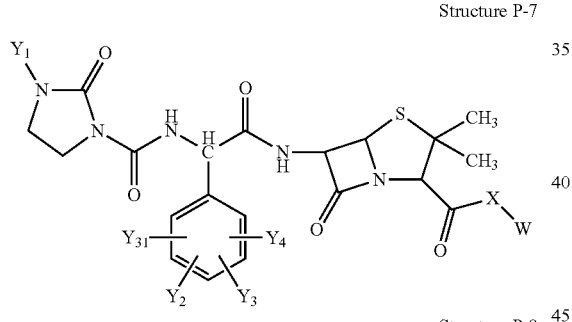
Structure P-8
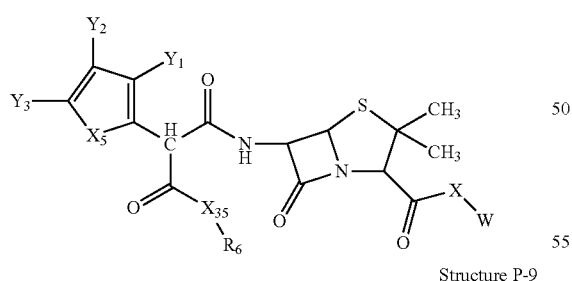
Structure P-9
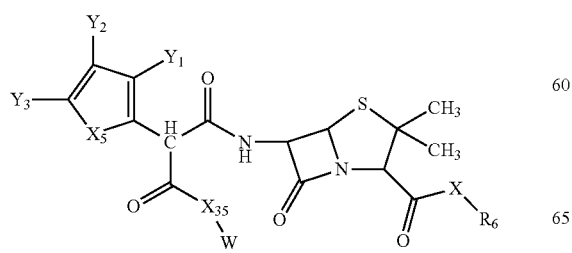
Structure P-10
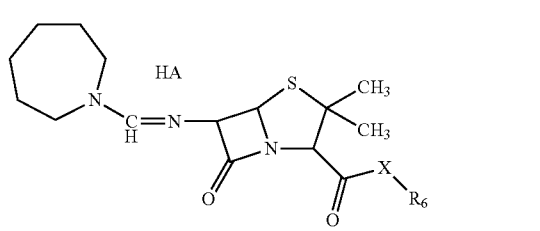
Structure P-11
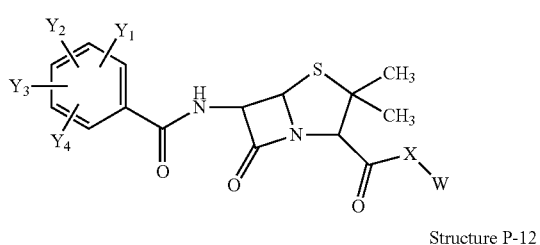
Structure P-12
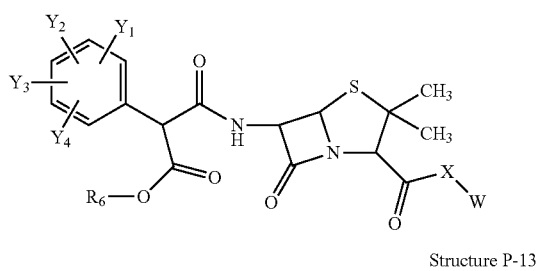
Structure P-13
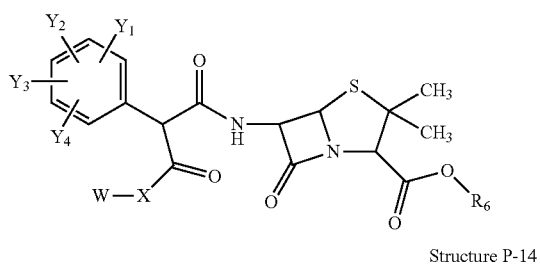
Structure P-14
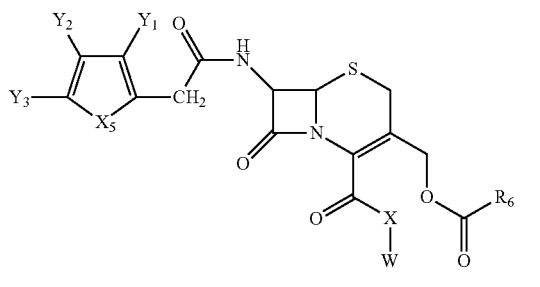
Structure P-15
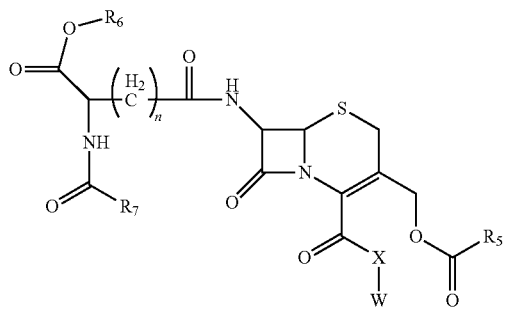

Structure P-16
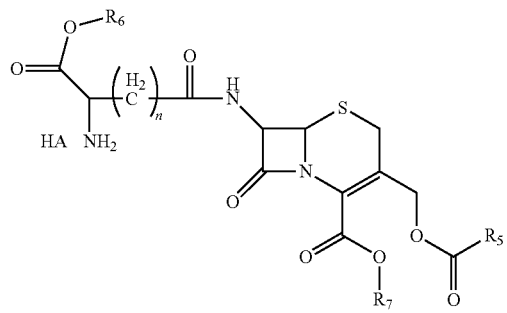
Structure P-17
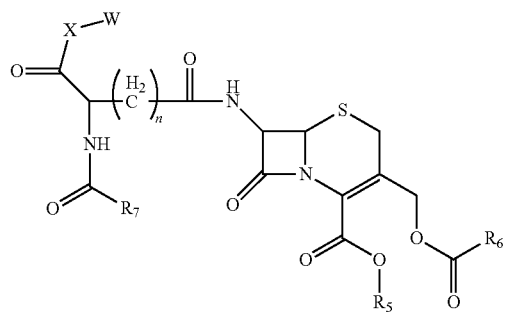
Structure P-18
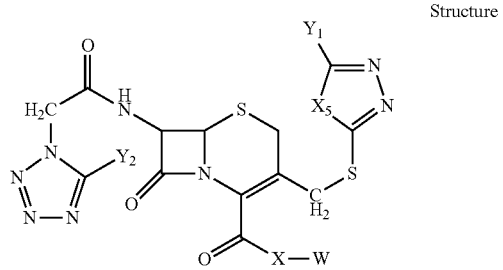
Structure P-19
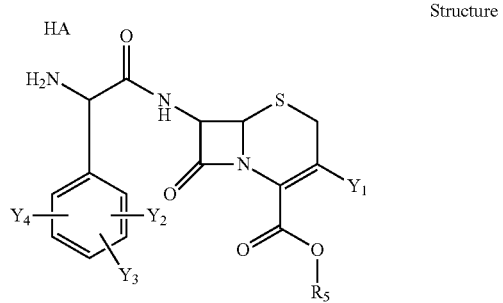
Structure P-20
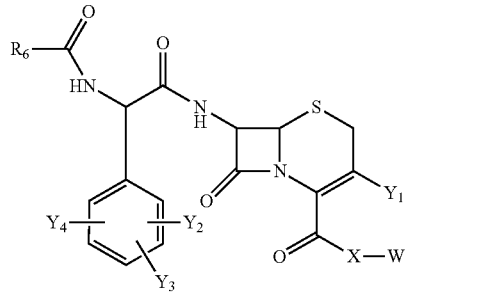
Structure P-21
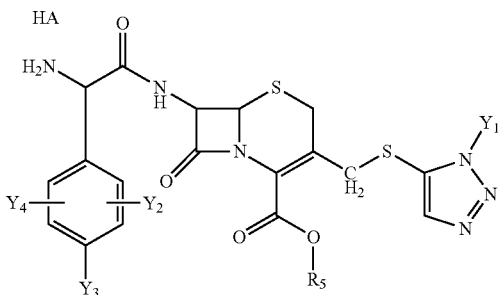
Structure P-22
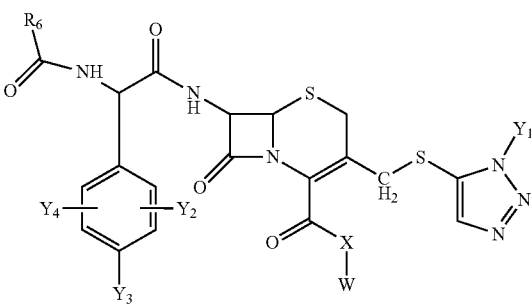
Structure P-23
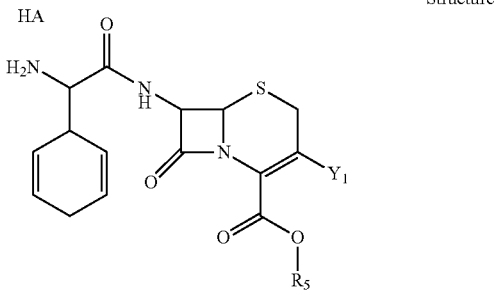
Structure P-24
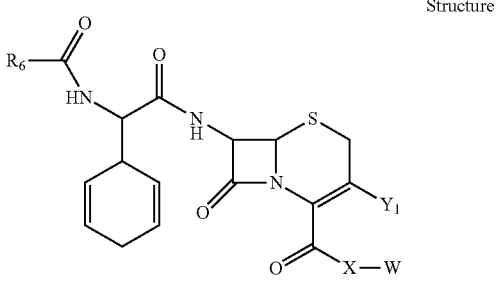
Structure P-25
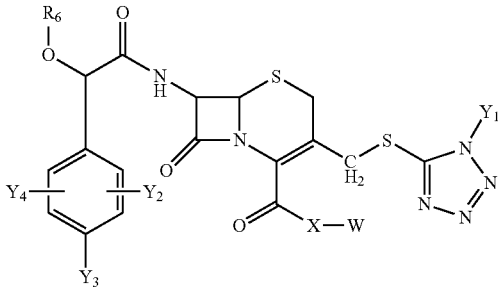

Structure P-26
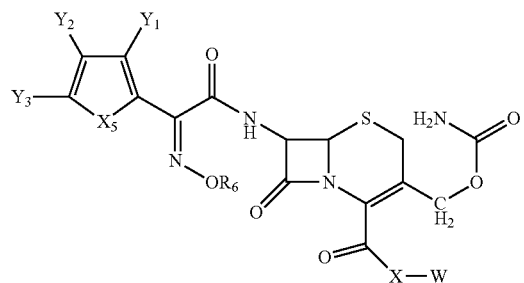
Structure P-27
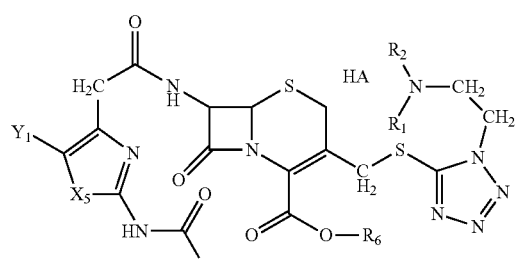
Structure P-28
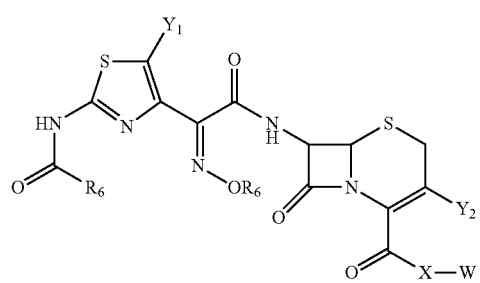
Structure P-29
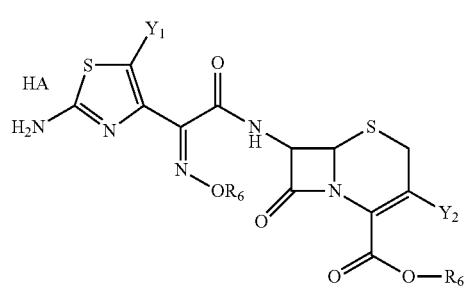
Structure P-30
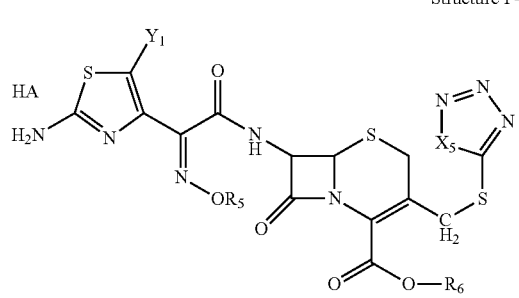
Structure P-31
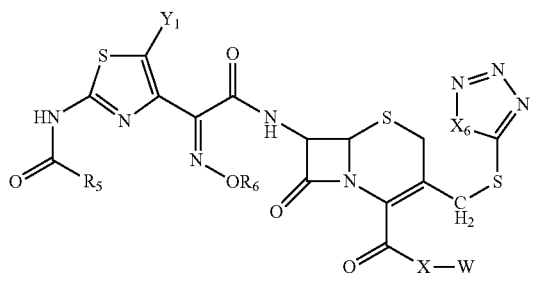
Structure P-32
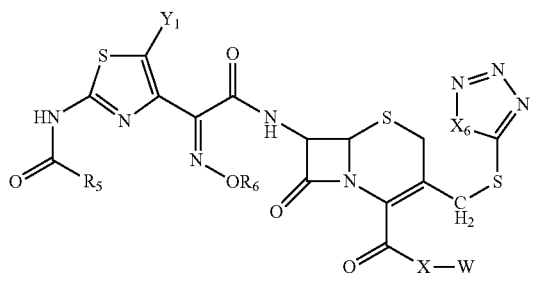
Structure P-33
Structure P-34
Structure P-35

Structure P-36
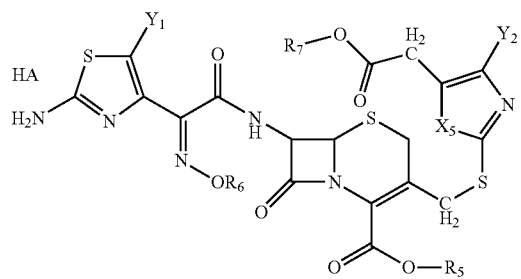
Structure P-37
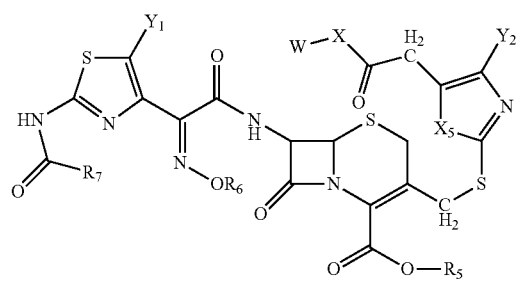
Structure P-38
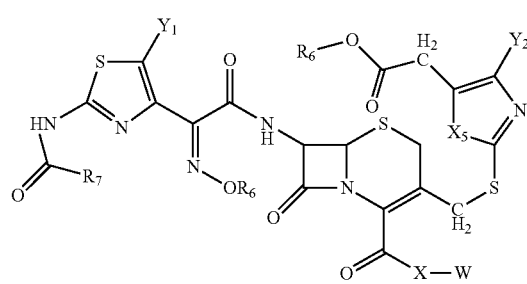
Structure P-39
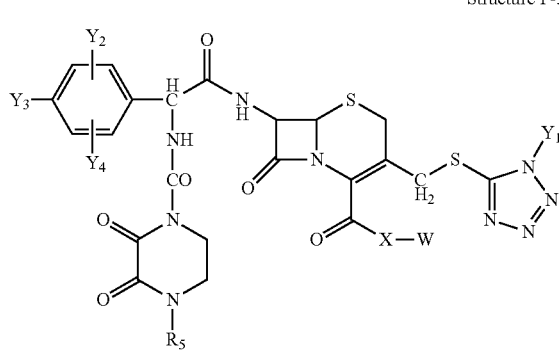
Structure P-40
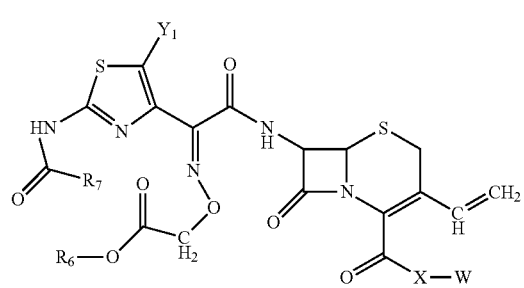
Structure P-41
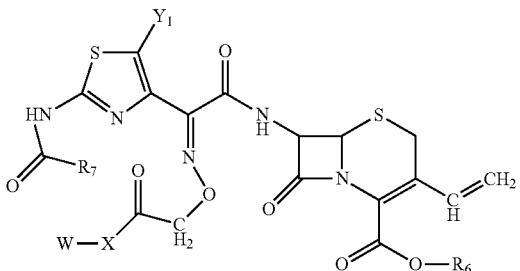
Structure P-42
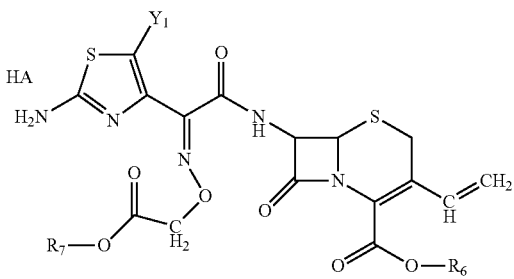
Structure P-43
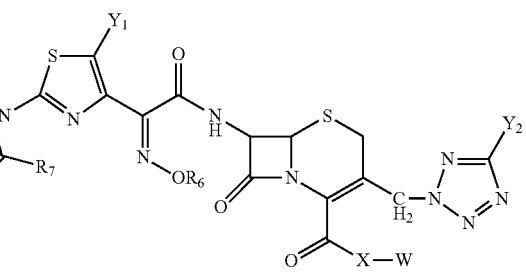
Structure P-44
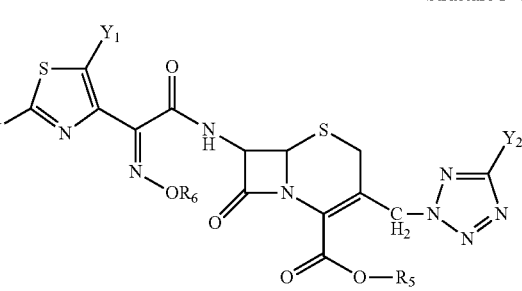
Structure P-45
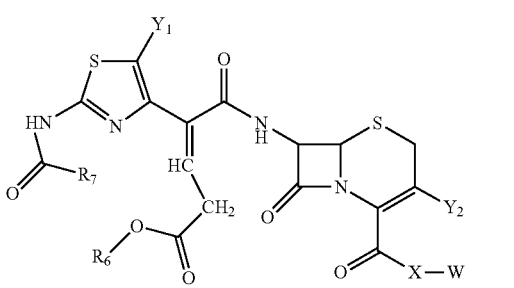

Structure P-46
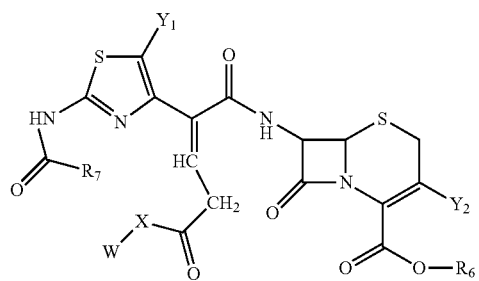
Structure P-47
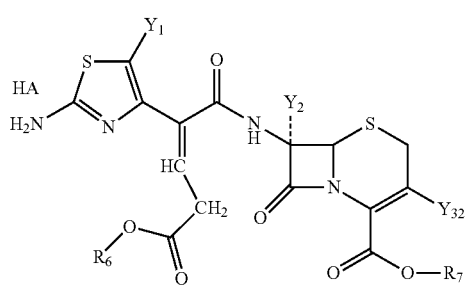
Structure P-48
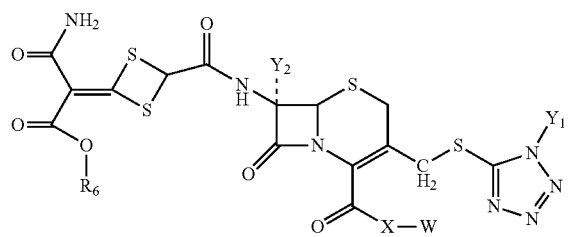
Structure P-49
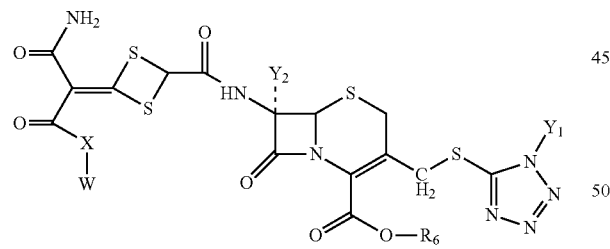
Structure P-50
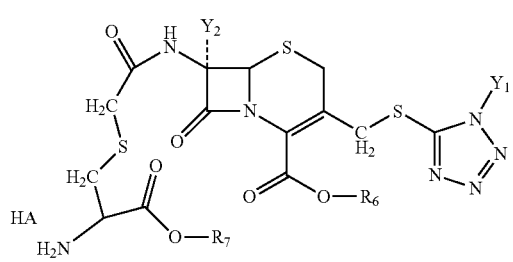
Structure P-51
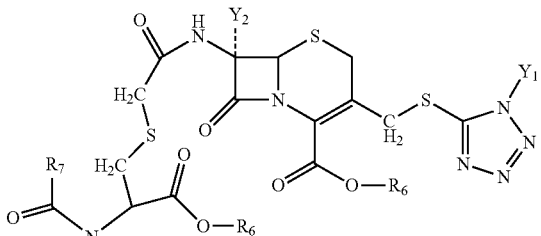
Structure P-52
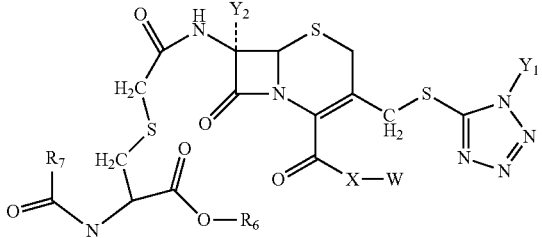
Structure P-53
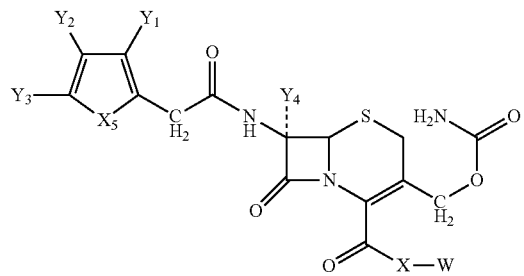
Structure P-54
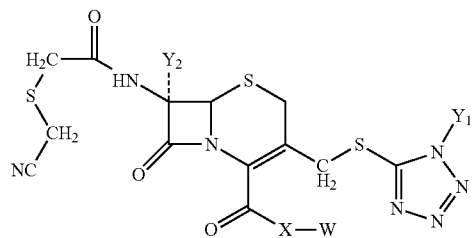
Structure P-55
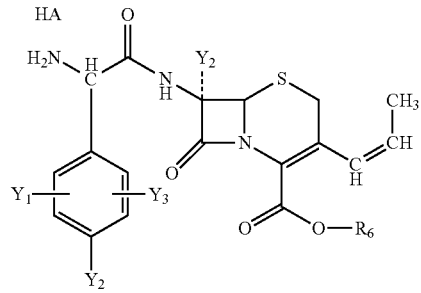

-continued
Structure P-56
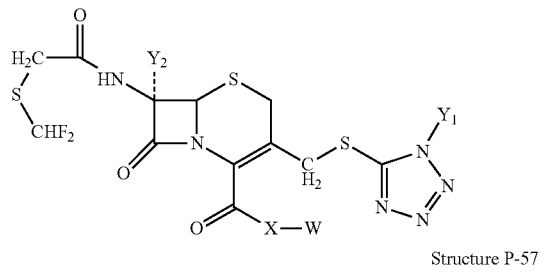
Structure P-57
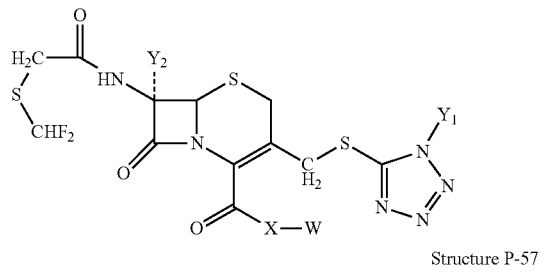
Structure P-58
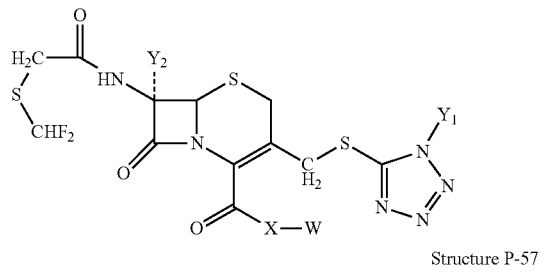
Structure P-59
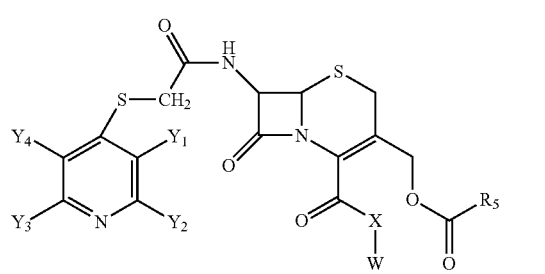
Structure P-60
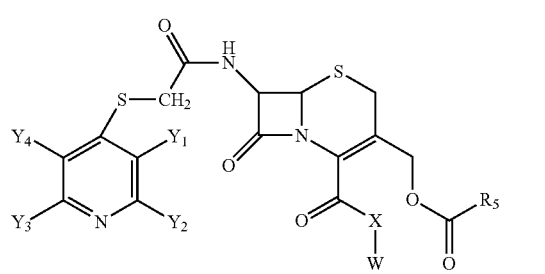
-continued
Structure P-61
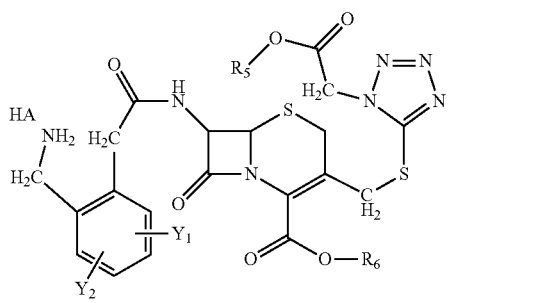
Structure P-62
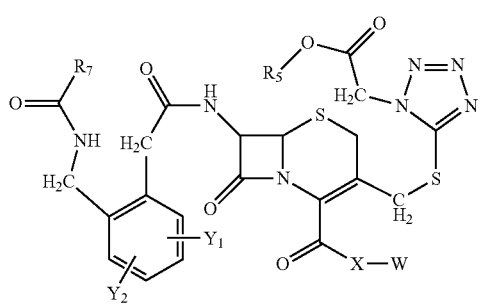
Structure P-64
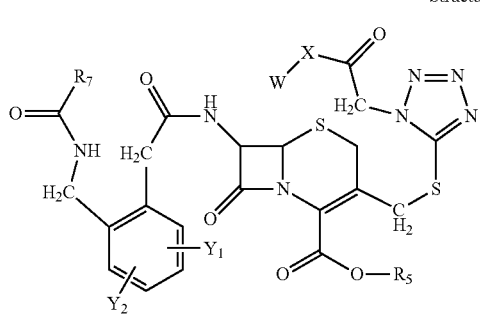
Structure P-64
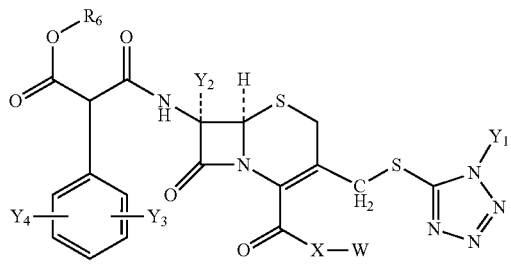
Structure P-65
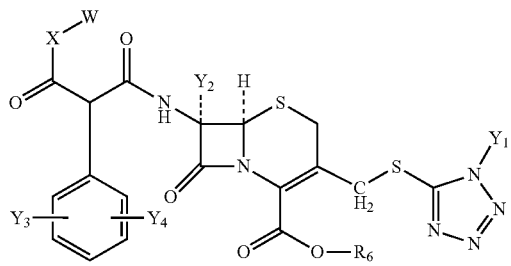

Structure P-66
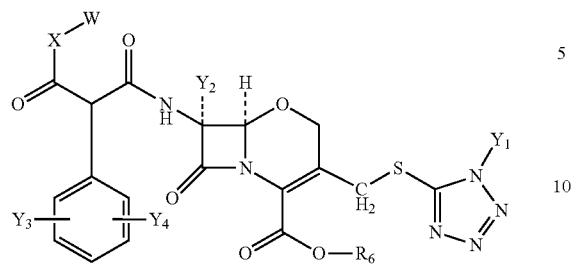
Structure P-67
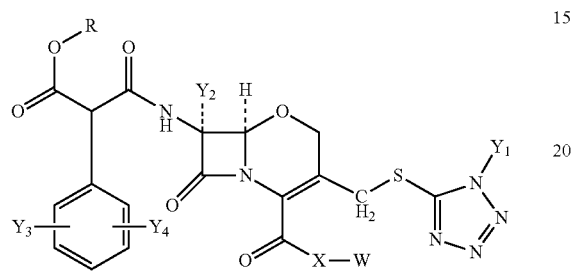
Structure P-68
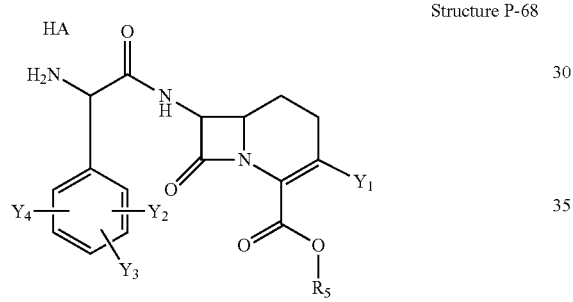
Structure P-69
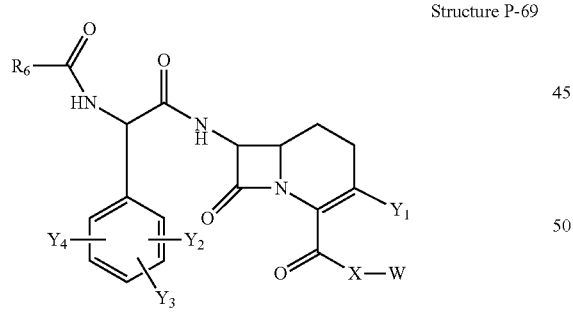
Structure P-70
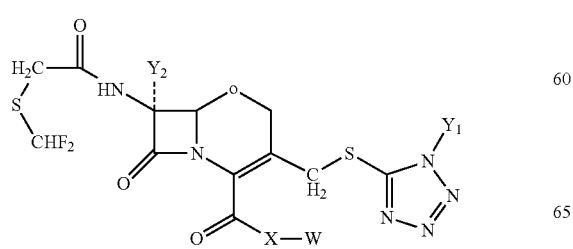
Structure P-71
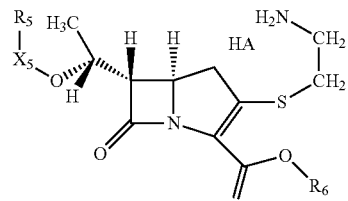
Structure P-72
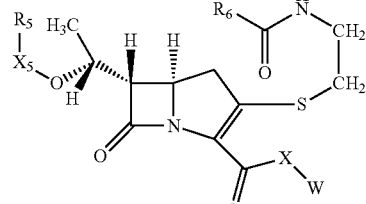
Structure P-73
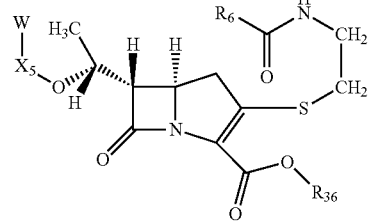
Structure P-74
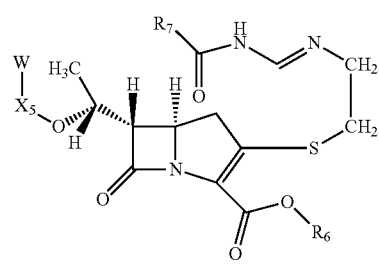
Structure P-75
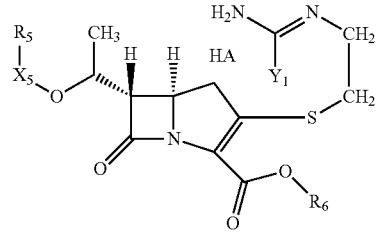
Structure P-76
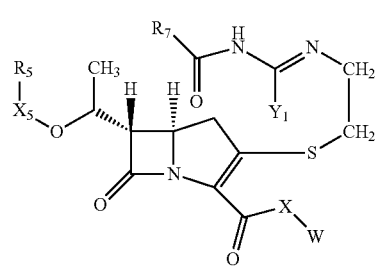

Structure P-77
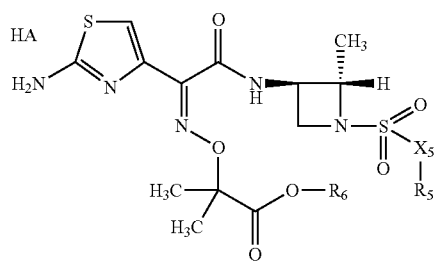
Structure P-78
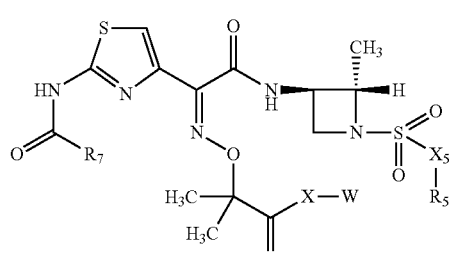
Structure P-79
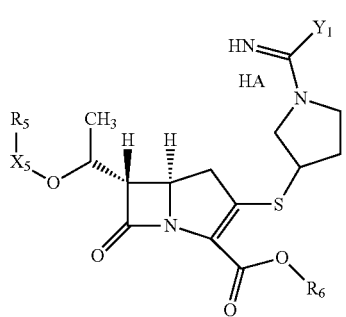
Structure P-80
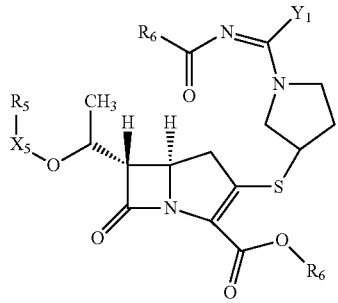
Structure P-81
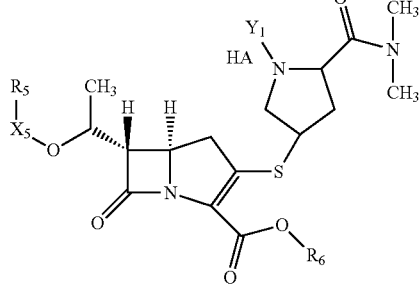
Structure P-82
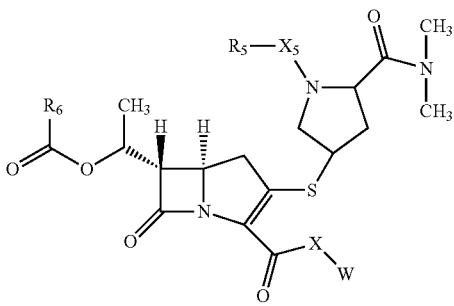
Structure P-83
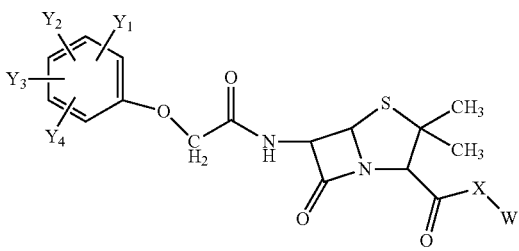
Structure P-84
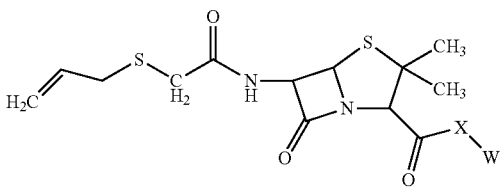
Structure P-85
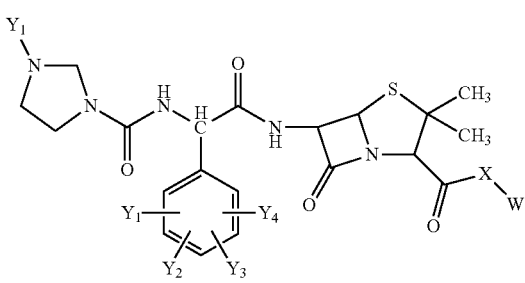
Structure P-86
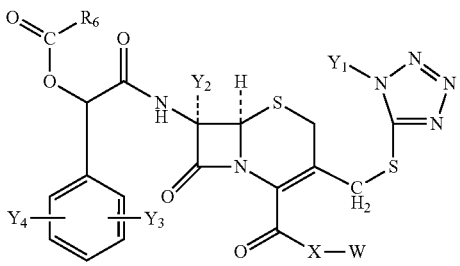
Structure I-1
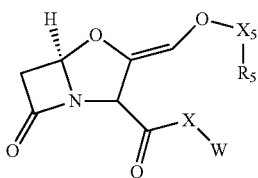

-continued
Structure I-2
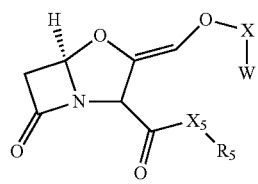
Structure I-3
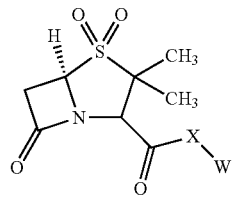
Structure I-4
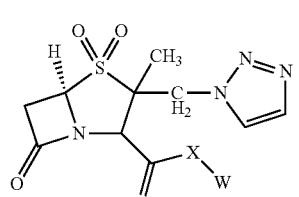
Structure I-5
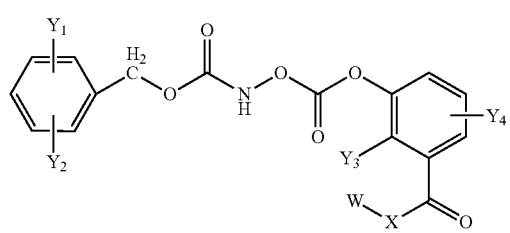
Structure I-6
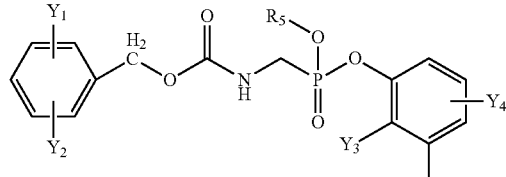
Structure I-7
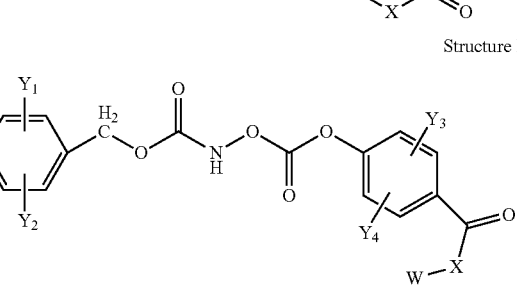
Structure I-8
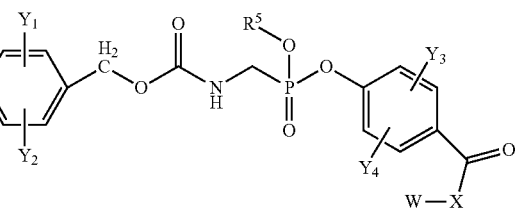
-continued
Structure I-90
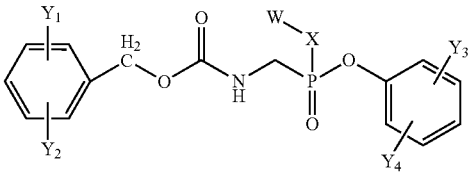
Structure I-10
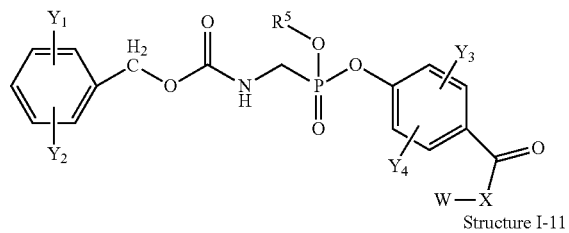
Structure I-11
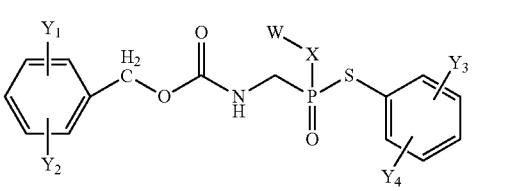
Structure I-12
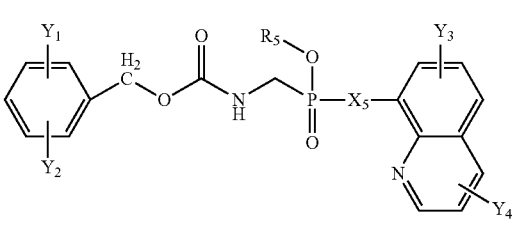
Structure I-13
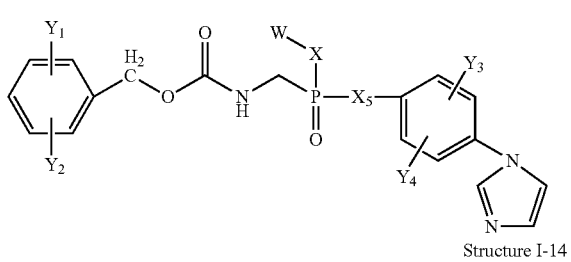
Structure I-14
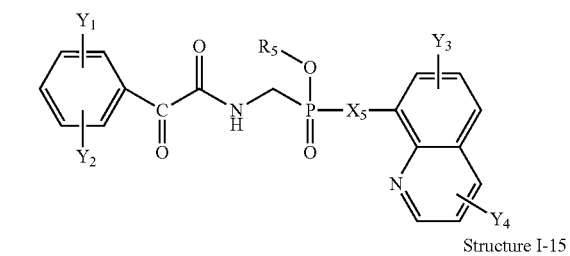
Structure I-15
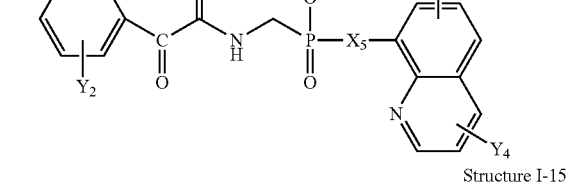

83
-continued
Structure I-16
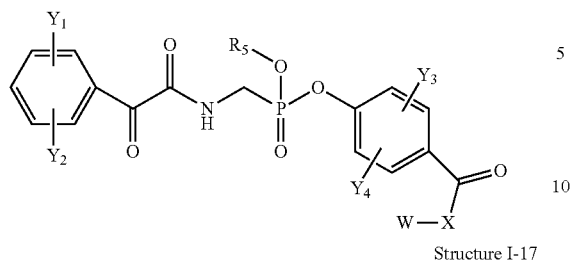
Structure I-17
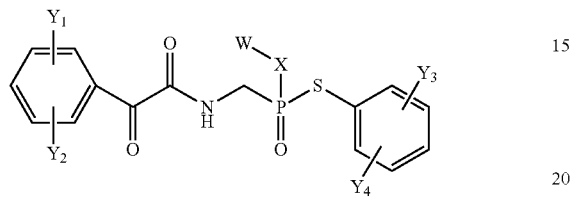
Structure I-18
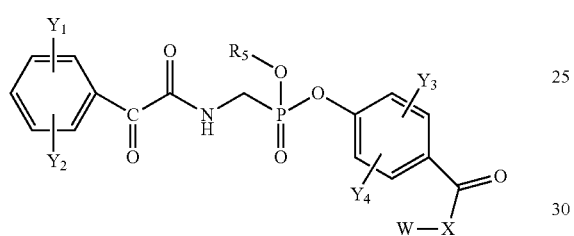
Structure I-19
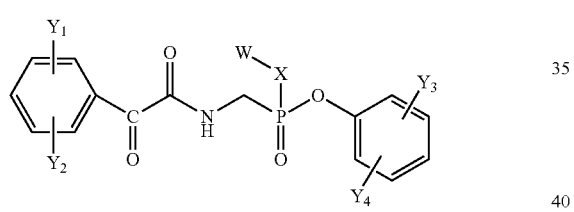
Structure I-20
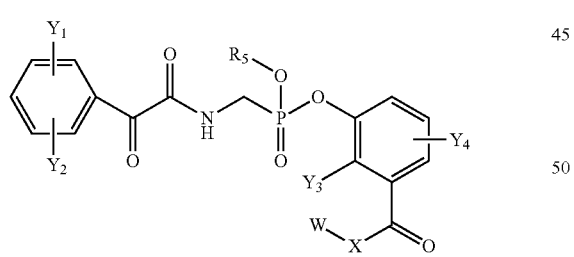
Structure I-21
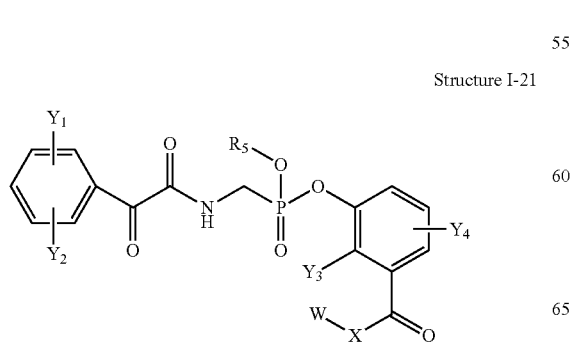
84
-continued
Structure I-22
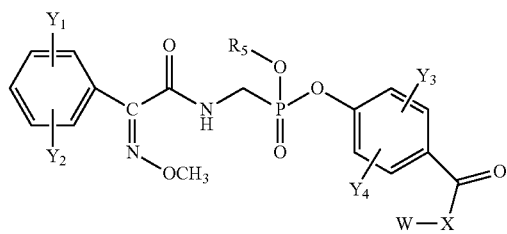
Structure I-23
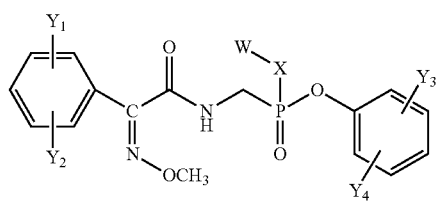
Structure I-24
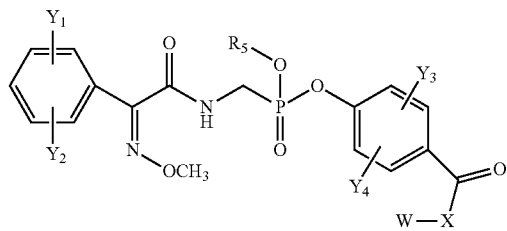
Structure I-25
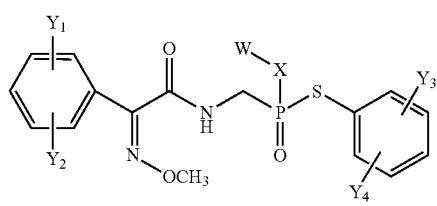
Structure I-26
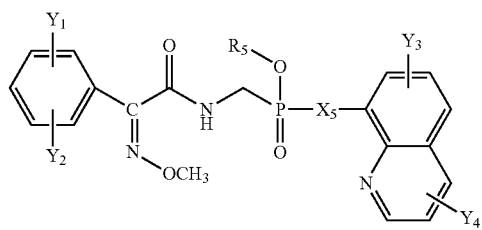
Structure I-27

Structure I-28
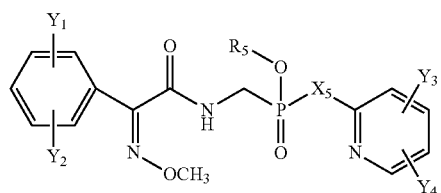
Structure I-29
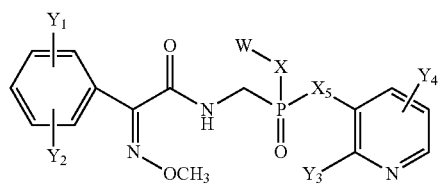
Structure I-30
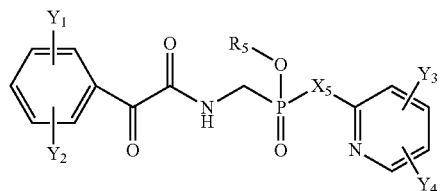
Structure I-31
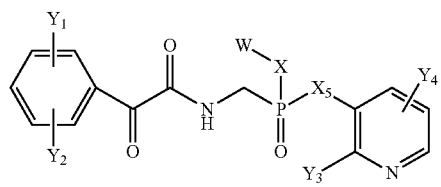
Structure I-32
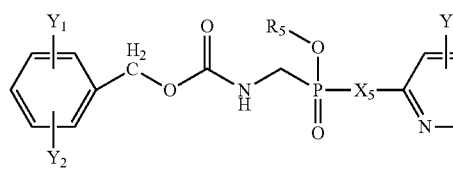
Structure I-33
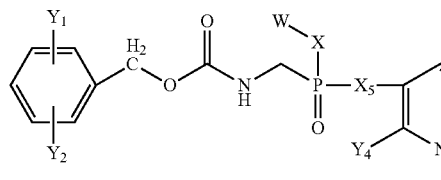
Structure S-1
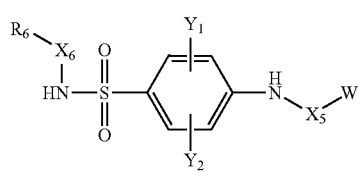
Structure S-2
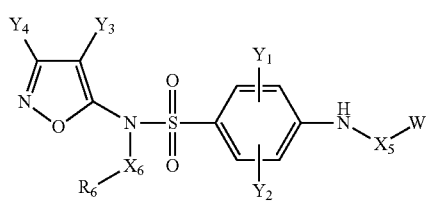
Structure S-3
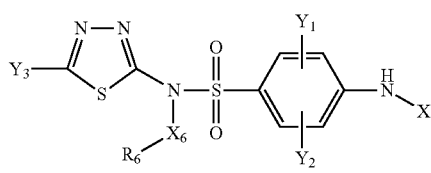
Structure S-4
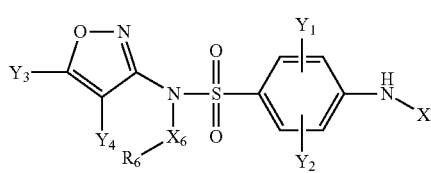
Structure S-5
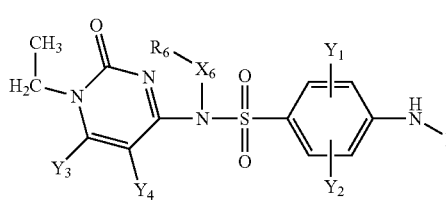
Structure S-6
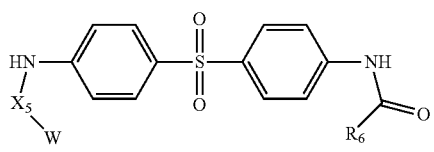
Structure S-7
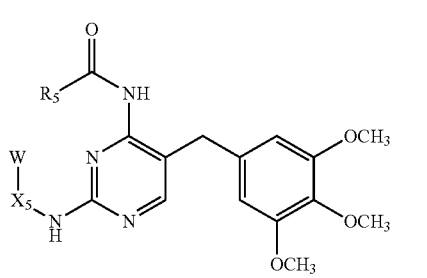
Structure S-8
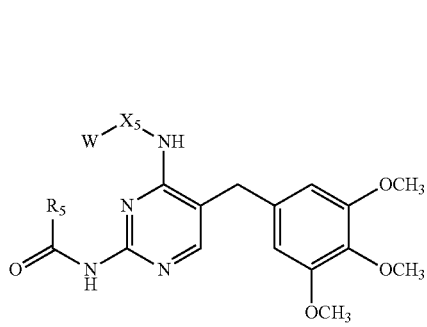

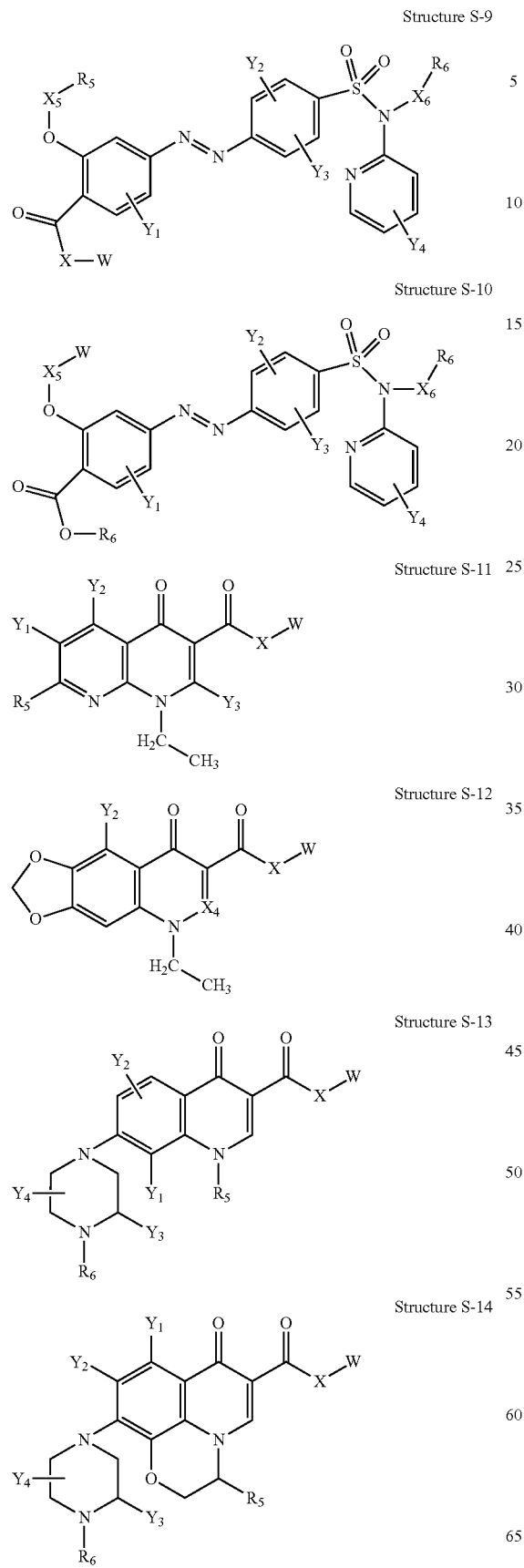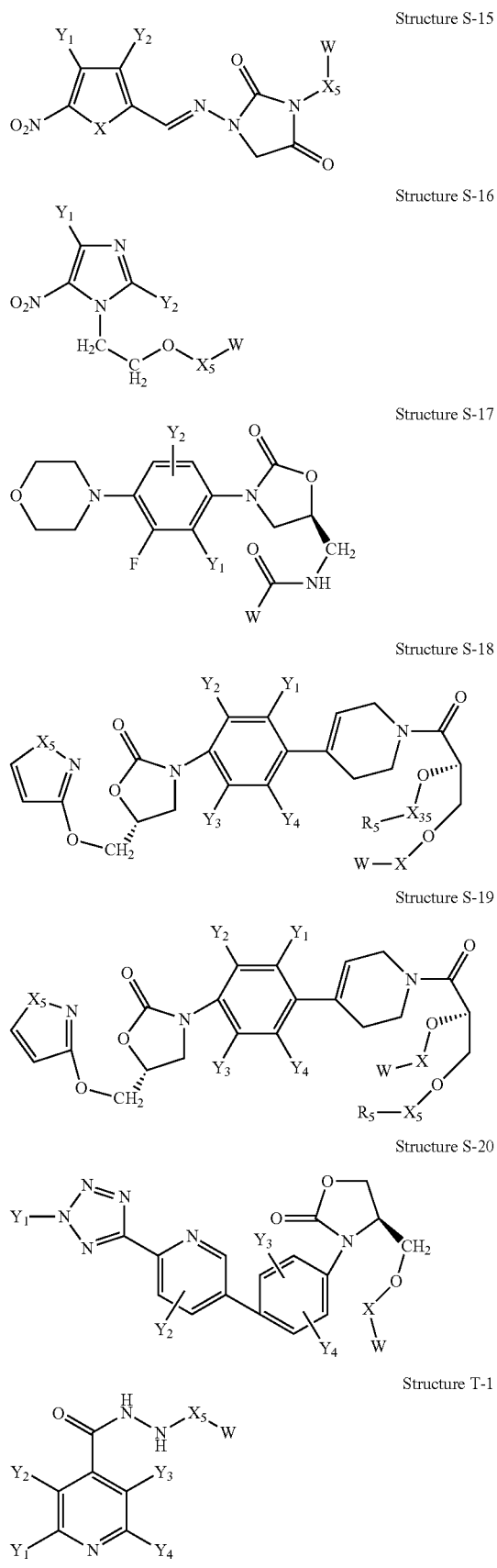

Structure T-2
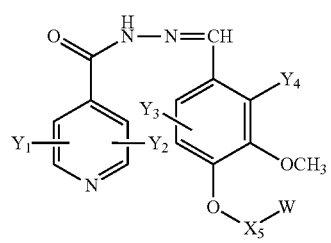
Structure T-3
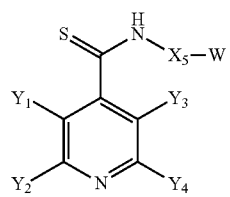
Structure T-4
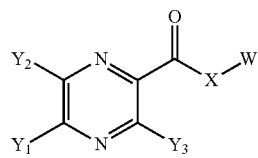
Structure T-5
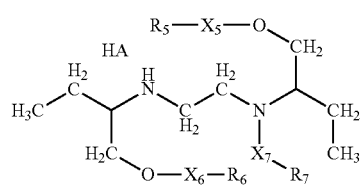
Structure T-6
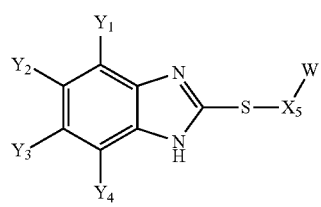
Structure T-7
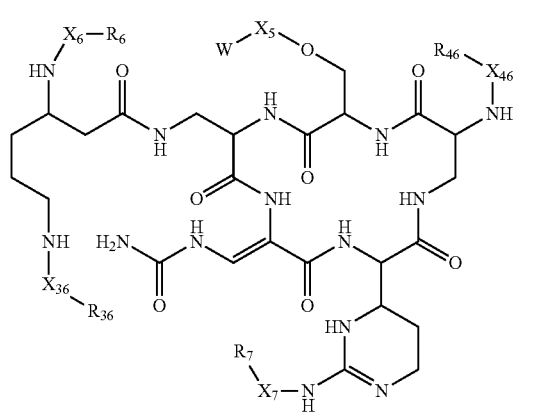
Structure T-8
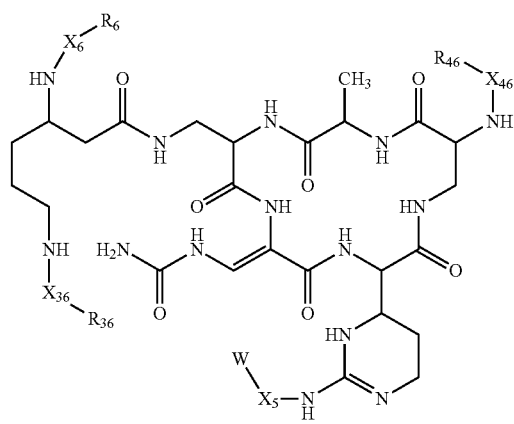
Structure T-9
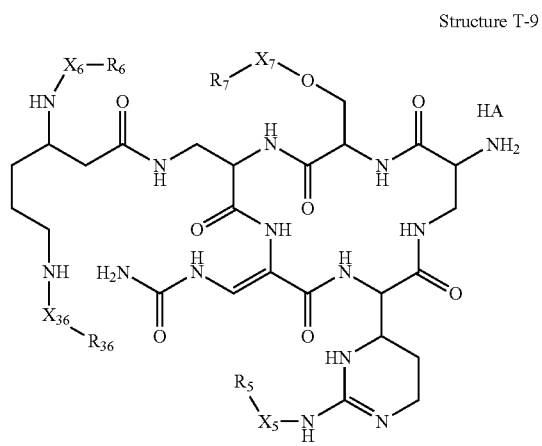
Structure T-10
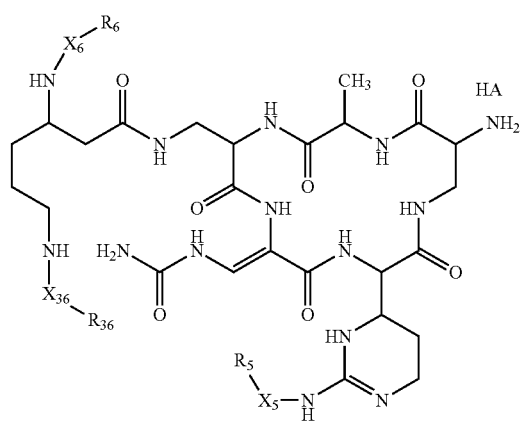
Structure T-11
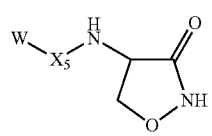

-continued

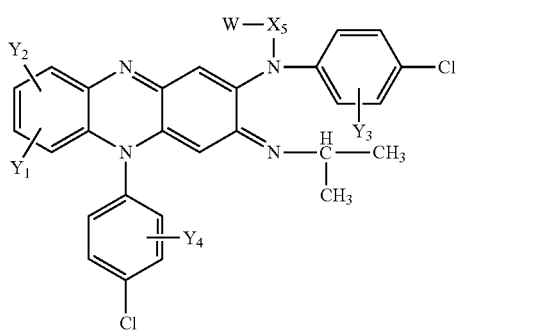

Structure T-12

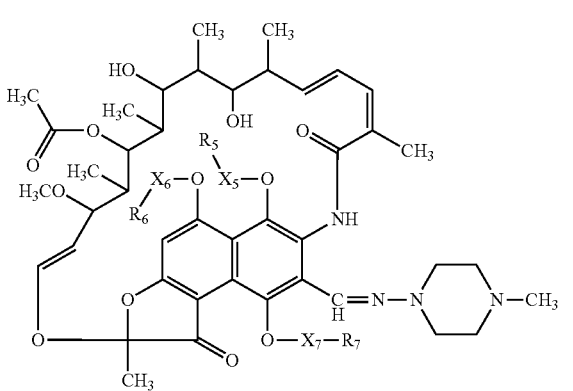

Structure T-13

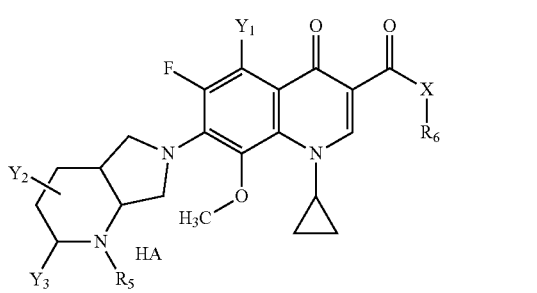

Structure T-14

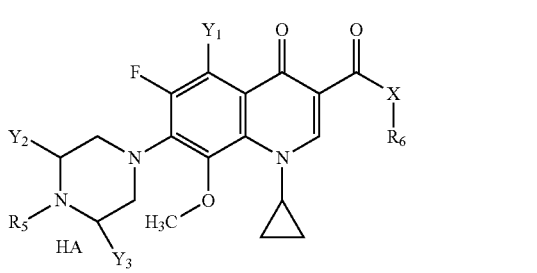

Strucuture T-15

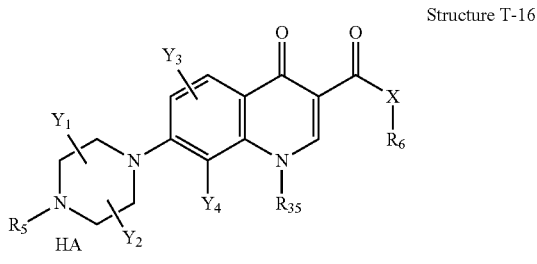

Structure T-16 including stereoisomers and pharmaceutically acceptable salts thereof, wherein m, n, $R_1$, $R_2$, $R_5$, $R_{35}$, $R_6$, $R_{36}$, $R_{46}$, $R_7$, $R_8$, $R_{38}$, W, X, $X_2$, $X_4$, $X_5$, $X_{35}$, $X_6$, $X_{36}$, $X_{46}$, $X_7$, $Y_1$, $Y_2$, $Y_{31}$, $Y_{32}$, $Y_3$, $Y_4$, Z, AA, HA, R, $R_s$, and $R_{11}$-$R_{16}$ are defined the same as supra.

II. Pharmaceutical Compositions Comprising HPPs

Another aspect of the invention relates to a pharmaceutical composition comprising at least one HPP of an antimicrobial or antimicrobial-related compound and a pharmaceutically acceptable carrier.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a HPP from one location, body fluid, tissue, organ (interior or exterior), or portion of the body, to another location, body fluid, tissue, organ, or portion of the body.

Each carrier is "pharmaceutically acceptable" in the sense of being compatible with the other ingredients, e.g., a HPP, of the formulation and suitable for use in contact with the tissue or organ of a biological system without excessive toxicity, irritation, allergic response, immunogenicity, or other problems or complications, commensurate with a reasonable benefit/risk ratio.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) alcohol, such as ethyl alcohol and propane alcohol; (20) phosphate buffer solutions; and (21) other non-toxic compatible substances employed in pharmaceutical formulations such as acetone.

The pharmaceutical compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

In one embodiment, the pharmaceutically acceptable carrier is an aqueous carrier, e.g. buffered saline and the like. In certain embodiments, the pharmaceutically acceptable carrier is a polar solvent, e.g. acetone and alcohol.

The concentration of HPP in these formulations can vary widely, and will be selected primarily based on fluid volumes, viscosities, body weight and the like in accordance with the particular mode of administration selected and the biological system's needs. For example, the concentration can be 0.0001% to 100%, 0.001% to 50%, 0.01% to 30%, 0.1% to 10% wt.

The compositions of the invention can be administered for prophylactic, therapeutic, and/or hygienic use. Such administration can be topical, mucosal, e.g., oral, nasal, vaginal, rectal, parenteral, transdermal, subcutaneous, intramuscular, intravenous, via inhalation, ophthalmic and other convenient routes. The pharmaceutical compositions can be administered in a variety of unit dosage forms depending upon the method of administration. For example, unit dosage forms suitable for oral administration include powder, tablets, pills, capsules and lozenges.

Thus, a typical pharmaceutical composition for intravenous administration would be about $10^{-10}$ g to about 100 g, about $10^{-10}$ g to about $10^{-3}$ g, about $10^{-9}$ g to about $10^{-6}$ g, about $10^{-6}$ g to about 100 g, about 0.001 g to about 100 g, about 0.01 g to about 10 g, or about 0.01 g to about 1 g per subject per day. Dosages from about 0.01 mg, up to about 5 g, per subject per day may be used. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

III. Applications of HPPs i) Methods for Penetrating a Biological Barrier.

Another aspect of the invention relates to a method of using a composition of the invention in penetrating one or more biological barriers in a biological subject. The method comprises a step of administering to a biological subject a HPP or an antimicrobial or antimicrobial-related compound, or a pharmaceutical composition thereof. In certain embodiments, a HPP exhibits more than about 20 times or higher, 50 times or higher, >about 100 times or higher, >about 200 time higher, >about 300 times or higher, >about 500 times or higher, >about 1,000 times or higher penetration rate through one or more biological barriers than its parent drug.

The term "biological barrier" as used herein refers to a biological layer that separates an environment into different spatial areas or compartments, which separation is capable of modulating (e.g. restricting, limiting, enhancing or taking no action in) the passing through, penetrating or translocation of substance or matter from one compartment/area to another. The different spatial areas or compartments as referred to herein may have the same or different chemical or biological environment(s). The biological layer as referred herein includes, but is not limited to, a biological membrane, a cell layer, a biological structure, an inner surface of subjects, organisms, organs or body cavities, an external surface of subjects, organisms, organs or body cavities, or any combination or plurality thereof.

Examples of a biological membrane include a lipid bilayer structure, eukaryotic cell membrane, prokaryotic cell membrane, and intracellular membrane (e.g., nucleus or organelle membrane, such as membrane or envelope of Golgi apparatus, rough and smooth endoplasmic reticulum (ER), ribosomes, vacuoles, vesicles, liposomes, mitochondria, lysosome, nucleus, chloroplasts, plastids, peroxisomes or microbodies).

The lipid bilayer referred to herein is a double layer of lipid-class molecules, including, but not limited to, phospholipids and cholesterol. In a particular embodiment, lipids for bilayer are amphiphilic molecules consisting of polar head groups and non-polar fatty acid tails. The bilayer is composed of two layers of lipids arranged so that their hydrocarbon tails face one another to form an oily core held together by the hydrophobic effect, while their charged heads face the aqueous solutions on either side of the membrane. In another particular embodiment, the lipid bilayer may contain one or more embedded protein and/or sugar molecule(s).

Examples of a cell layer include a lining of eukaryotic cells (e.g., epithelium, lamina propria and smooth muscle or muscularis mucosa (in gastrointestinal tract)), a lining of prokaryotic cells (e.g., surface layer or S-layer which refers to a two dimensional structure monomolecular layer composed of identical proteins or glycoproteins, specifically, an S-layer refers to a part of a cell envelope commonly found in bacteria and archaea), a biofilm (a structured community of microorganisms encapsulated within a self-developed polymeric matrix and adherent to a living or inert surface), and a plant cell layer (e.g., empidermis). The cells may be normal cells or pathological cells (e.g. disease cells, cancer cells).

Examples of biological structures include structures sealed by tight or occluding junctions that provide a barrier to the entry of toxins, bacteria and viruses, e.g. the blood milk barrier and the blood brain barrier (BBB). In particular, BBB is composed of an impermeable class of endothelium, which presents both a physical barrier through tight junctions adjoining neighboring endothelial cells and a transport barrier comprised of efflux transporters. The biological structure may also include a mixture of cells, proteins and sugars (e.g. blood clots).

Examples of the inner surface of subjects, organisms, organs or body cavities include buccal mucosa, esophageal mucosa, gastric mucosa, intestinal mucosa, olfactory mucosa, oral mucosa, bronchial mucosa, uterine mucosa and endometrium (the mucosa of the uterus, inner layer of the wall of a pollen grain or the inner wall layer of a spore), or a combination or plurality thereof.

Examples of the external surface of subjects, organisms, organs or body cavities include capillaries (e.g. capillaries in the heart tissue), mucous membranes that are continuous with skin (e.g. such as at the nostrils, the lips, the ears, the genital area, and the anus), outer surface of an organ (e.g. liver, lung, stomach, brain, kidney, heart, ear, eye, nose, mouth, tongue, colon, pancreas, gallbladder, duodenum, rectum stomach, colonrectum, intestine, vein, respiratory system, vascular, anorectum and pruritus ani), skin, cuticle (e.g. dead layers of epidermal cells or keratinocytes or superficial layer of overlapping cells covering the hair shaft of an animal, a multi-layered structure outside the epidermis of many invertebrates, plant cuticles or polymers cutin and/or cutan), external layer of the wall of a pollen grain or the external wall layer of a spore), and a combination or plurality thereof.

In addition, a biological barrier further includes a sugar layer, a protein layer or any other biological layer, or a combination or plurality thereof. For example, skin is a biological barrier that has a plurality of biological layers. A skin comprises an epidermis layer (outer surface), a demis layer and a subcutaneous layer. The epidermis layer contains several layers including a basal cell layer, a spinous cell layer, a granular cell layer, and a stratum corneum. The cells in the epidermis are called keratinocytes. The stratum corneum ("horny layer") is the outmost layer of the epidermis, wherein cells here are flat and scale-like ("squamous") in shape. These cells contain a lot of keratin and are arranged in overlapping layers that impart a tough and oilproof and waterproof character to the skin's surface.

ii) Methods for Diagnosing a Condition in a Biological System.

Another aspect of the invention relates to a method of using a composition of the invention in diagnosing a condition in a biological system. The method comprises the following steps:

1) administrating a composition comprising a HPP of an antimicrobial or antimicrobial-related compound to the biological subject;

2) detecting the presence, location or amount of the HPP, the functional unit of the HPP or a metabolite thereof in the biological subject; and 3) determining a condition in the biological system.

In certain embodiments, the HPP (or the agent cleaved from the HPP) aggregates in the site of action where a condition occurs. In certain embodiments, the presence, location or amount of the functional unit of the HPP is also detected. In certain embodiments, the onset, development, progress, or remission of a condition (e.g., infection) associated is also determined.

In certain embodiments, the HPP is labeled with or conjugated to a detectable agent. Alternatively, the HPP is prepared to include radioisotopes for detection. Numerous detectable agents are available which can be generally grouped into the following categories:

(a) Radioisotopes, such as $^{35}S$, $^{14}C$, $^{13}C$, $^{15}N$, $^{125}I$, $^{3}H$, and $^{131}I$. The diagnostic agent can be labeled with the radioisotope using the techniques known in the art and radioactivity can be measured using scintillation counting; in addition, the diagnostic agent can be spin labeled for electron paramagnetic resonance for carbon and nitrogen labeling.

(b) Fluorescent agents such as BODIPY, BODIPY analogs, rare earth chelates (europium chelates), fluorescein and its derivatives, FITC, 5,6 carboxyfluorescein, rhodamine and its derivatives, dansyl, Lissamine, phycoerythrin, green fluorescent protein, yellow fluorescent protein, red fluorescent protein and Texas Red. Fluorescence can be quantified using a fluorometer.

(c) Various enzyme-substrate agents, such luciferases (e.g., firefly luciferase and bacterial luciferase), luciferin, 2,3-dihydrophthalazinediones, malate dehydrogenase, urease, peroxidase such as horseradish peroxidase (HRPO), alkaline phosphatase, 6-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3'5, 5'-tetramethyl benzidine hydrochloride (TMB)); (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

In certain embodiments, the detectable agent is not necessarily conjugated to the diagnostic agent but is capable of recognizing the presence of the diagnostic agent and the diagnostic agent can be detected.

In certain embodiments, the HPP of the invention can be provided in a kit, i.e., a packaged combination of reagents in predetermined amounts with instructions for performing the diagnostic assay. Where the HPP is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

iii) Methods for Screening a Substance for a Desired Character

Another aspect of the invention relates to a method of screening a HPP for a desired character.

In certain embodiments, the method comprises: covalently linking a test functional unit to a transportational unit through a linker to form a test composition (or covalently linking a functional unit to a test transportational unit through a linker, or covalently linking a functional unit to a transportational unit through a test linker)

2) administrating the test composition to a biological system; and 3) determining whether the test composition has the desired nature or character.

In one embodiment, a desired character may include, for example, 1) the ability of a test functional unit to form a high penetration composition or convert back to a parent drug, 2) the penetration ability and/or rate of a test composition, 3) the efficiency and/or efficacy of a test composition, 4) the transportational ability of a test transportational unit, and 5) the cleavability of a test linker.

iv) Methods for Treating a Condition in a Biological Subject

Another aspect of the invention relates to a method of using a composition of the invention in treating a condition in a biological system. The method comprises administrating the pharmaceutical composition to the biological system.

The term "treating" as used herein means curing, alleviating, inhibiting, or preventing. The term "treat" as used herein means cure, alleviate, inhibit, or prevent. The term "treatment" as used herein means cure, alleviation, inhibition or prevention.

The term "biological system," "biological subject" or "subject" as used herein means an organ, a group of organs that work together to perform a certain task, an organism, or a group of organisms. The term "organism" as used herein means an assembly of molecules that function as a more or less stable whole and has the properties of life, such as animal, plant, fungus, or micro-organism.

The term "animal" as used herein means an eukaryotic organism characterized by voluntary movement. Examples of animal include, without limitation, vertebrata (e.g. human, mammals, birds, reptiles, amphibians, fishes, marsipobranchiata and leptocardia), tunicata (e.g. thaliacea, appendicularia, sorberacea and ascidioidea), articulata (e.g. insecta, myriapoda, malacapoda, arachnida, pycnogonida, merostomata, crustacea and annelida), gehyrea (anarthropoda), and helminthes (e.g. rotifera).

The term "plant" as used herein means organisms belonging to the kindom Plantae. Examples of plant include, without limitation, seed plants, bryophytes, ferns and fern allies. Examples of seed plants include, without limitation, cycads, ginkgo, conifers, gnetophytes, angiosperms. Examples of bryophytes include, without limitation, liverworts, hornworts and mosses. Examples of ferns include, without limitation, ophioglossales (e.g. adders-tongues, moonworts, and grape-ferns), marattiaceae and leptosporangiate ferns. Examples of fern allies include, without limitation, lycopsida (e.g. clubmosses, spikemosses and quillworts), psilotaceae (e.g. lycopodiophyta and whisk ferns) and equisetaceae (e.g. horsetails).

The term "fungus" as used herein means a eukaryotic organism that is a member of the kingdom Fungi. Examples of fungus include, without limitation, chytrids, blastocladiomycota, neocallimastigomycota, zygomycota, glomeromycota, ascomycota and basidiomycota.

The term "microorganism" as used herein means an organism that is microscopic (e.g. with length scale of micrometer). Examples of microorganism include, without limitation, bacteria, fungi, archaea, protists and microscopic plants (e.g. green algae) and microscopic animals (e.g. plankton, planarian and amoeba).

Some examples of the conditions the method can treat include conditions that can be treated by the parent drug of the HPP.

v). Methods of Using HPPs of Antimicrobials and Antimicrobial-Related Compounds and Pharmaceutical Compositions Thereof in Treatments.

Another aspect of the invention relates to a method of using HPPs of antimicrobials or antimicrobial-related compounds, or pharmaceutical compositions thereof in treating a condition in a biological system or subject by administrating a HPP of an antimicrobial or antimicrobial-related compound, or a pharmaceutical composition thereof to the biological system or subject.

Antimicrobials and antimicrobial-related compounds can be used to regulate a wide range of biological processes in a biological system. Conditions that are related to such biological processes are treatable by the corresponding antimicrobials or antimicrobial-related compounds, and therefore treatable by HPPs/HPCs of the antimicrobials or antimicrobial-related compounds, and a pharmaceutical composition thereof.

Such conditions include, but are not limited to, pain, injuries and microorganism related conditions. Microoranism related conditions are conditions that are caused by microorganisms such as bacteria, fungi, protozoans and viruses. For example, conditions caused by bacteria (bacteria-related conditions), conditions caused by protozoa (protozoa-related conditions), conditions caused by fungi (fungi-related conditions) and conditions caused by virus (virus-related conditions).

Bacteria-related conditions include, for example, infections (e.g. infection condition in an organ such as liver, lung, stomach, brain, kidney, heart, ear, eye, nose, mouth, tongue, colon, pancreas, gallbladder, duodenum, rectum stomach, colonrectum, intestine, vein, respiratory system, vascular, anorectum and pruritus ani, respiratory infections, upper respiratory tract infections, urinary tract infections, nosocomial infections, *pseudomonas* infection, Coagulase-positive staphylococcal infections (e.g. skin infection, toxinoses, acute infective endocarditis, septicemia, necrotizing pneumonia), infections of implanted prostheses, opportunistic infections with septicemia and pneumonia), plague (e.g. bubonic plague and pneumonic plague), anthrax (e.g. cutaneous anthrax, pulmonary anthrax and gastrointestinal antrax), lyme diseases, brucellosis, whooping cough, acute enteritis, respiratory infection, psittacosis, nongonococcal urethritis, trachoma, inclusion conjunctivitis of the newborn, lymphogranuloma venereum, pseudomembranous colitis, gas gangrene, food poisoning, anaerobic cellulitis, diphtheria, diarrhea, meningitis in infants, hemorrhagic colitis, hemolytic-uremic syndrome, tularemia, pneumonia, bronchitis, peptic ulcer, legionnaire's disease, Pontiac fever, leptospirosis, listeriosis, leprosy, turberculosis, *mycoplasma* pneumonia, gonorrhea, ophthalmia neonatorum, septic arthritis, meningococcal disease, waterhouse-friderichsen syndrome, Rocky mountain spotted fever, typhoid fever type *salmonellosis, salmonellosis* with gastroenteritis and enterocolitis, bacillary dysentery/shigellosis, cystitis, meningitis and septicemia, endometritis, otitis media, sinusitis, syphilis, necrotizing fasciitis, streptococcal pharyngitis, scarlet fever, rheumatic fever, impetigo, erysipelas, puerperal fever, and cholera.

Protozoa related conditions include, for example, malaria, sleeping sickness, and toxoplasmosis.

Fungi related conditions include, for example, aspergillosis, blastomycosis, ringworm, candidiasis, coccidioidomycois, cryptococcosis, histoplasmosis, paracoccidiomycosis, sporotrichosis, and zygomycosis.

Virus related conditions include, for example, influenza, yellow fever and AIDS.

In certain embodiments, a method of treating a condition in a subject amelioratable or treatable with antimicrobials or antimicrobial-related compounds comprises administering a therapeutic effective amount of a HPP of an antimicrobial or antimicrobial-related compound, or a pharmaceutical composition thereof to the subject.

A HPP or a pharmaceutical composition thereof can be administered to a biological system by any administration route known in the art, including without limitation, oral, enteral, buccal, nasal, topical, rectal, vaginal, aerosol, transmucosal, epidermal, transdermal, dermal, ophthalmic, pulmonary, subcutaneous, and/or parenteral administration. The pharmaceutical compositions can be administered in a variety of unit dosage forms depending upon the method of administration.

A parenteral administration refers to an administration route that typically relates to injection which includes but is not limited to intravenous, intramuscular, intraarterial, intrathecal, intracapsular, intraorbital, intra cardiac, intradermal, intraperitoneal, transtracheal, subcutaneous, subcuticular, intraarticular, subcapsular, subarachnoid, intraspinal, and/or intrasternal injection and/or infusion.

A HPP or a pharmaceutical composition thereof can be given to a subject in the form of formulations or preparations suitable for each administration route. The formulations useful in the methods of the invention include one or more HPPs, one or more pharmaceutically acceptable carriers therefor, and optionally other therapeutic ingredients. The formulations may conveniently be presented in unit dosage form and may be prepared by any methods well known in the art of pharmacy. The amount of active ingredient which can be combined with a carrier material to produce a single dosage form will vary depending upon the subject being treated and the particular mode of administration. The amount of a HPP which can be combined with a carrier material to produce a pharmaceutically effective dose will generally be that amount of a HPP which produces a therapeutic effect. Generally, out of one hundred percent, this amount will range from about 1 percent to about ninety-nine percent of the HPP, preferably from about 20 percent to about 70 percent.

Methods of preparing these formulations or compositions include the step of bringing into association a HPP with one or more pharmaceutically acceptable carriers and, optionally, one or more accessory ingredients. In general, the formulations are prepared by uniformly and intimately bringing into association a HPP with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a HPP as an active ingredient. A compound may also be administered as a bolus, electuary, or paste.

In solid dosage forms for oral administration (e. g., capsules, tablets, pills, dragees, powders, granules and the like), the HPP is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate, (5) solution retarding agents, such as paraffin, (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered antimicrobials or peptidomimetic moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of a HPP therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain pacifying agents and may be of a composition that they release the HPP(s) only, or preferentially, in a certain portion of the gastrointestinal tract, optionally, in a delayed manner. Examples of embedding compositions which can be used include polymeric substances and waxes. The HPP can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the HPP, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the HPP, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more HPPs with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Formulations for the topical or transdermal or epidermal or dermal administration of a HPP composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required. The ointments, pastes, creams and gels may contain, in addition to the HPP composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the HPP composition, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

A HPP or a pharmaceutical composition thereof can be alternatively administered by aerosol. This can be accomplished by preparing an aqueous aerosol, liposomal preparation or solid particles containing the HPPs. A nonaqueous (e. g., fluorocarbon propellant) suspension could be used. Sonic nebulizers can also be used. An aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches can also be used to deliver HPP compositions to a target site. Such formulations can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Formulations suitable for parenteral administration comprise a HPP in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacterostats, solutes which render the formulation isotonic with the blood of the intended recipient or suspending or thickening agents.

Examples of suitable aqueous and nonaqueous carriers which may be employed in the formulations suitable for parenteral administration include water, ethanol, polyols (e. g., such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Formulations suitable for parenteral administration may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Injectable depot forms are made by forming microencapsule matrices of a HPP or in biodegradable polymers such as polylactide-polyglycolide. Depending on the ratio of the HPP to polymer, and the nature of the particular polymer employed, the rate of drug release can be controlled. Examples of other biodegradable polymers include poly (orthoesters) and poly (anhydrides). Depot injectable formulations are also prepared by entrapping the HPP in liposomes or microemulsions which are compatible with body tissue.

In certain embodiments, a HPP of an antimicrobial or antimicrobial-related compound, or a pharmaceutical composition thereof is delivered to a disease or tumor site in a therapeutically effective dose. As is known in the art of pharmacology, the precise amount of the pharmaceutically effective dose of a HPP that will yield the most effective results in terms of efficacy of treatment in a given patient will depend upon, for example, the activity, the particular nature, pharmacokinetics, pharmacodynamics, and bioavailability of a particular HPP, physiological condition of the subject (including race, age, sex, weight, diet, disease type and stage, general physical condition, responsiveness to a given dosage and type of medication), the nature of pharmaceutically acceptable carriers in a formulation, the route and frequency of administration being used, and the severity or propensity of a disease caused by pathogenic target microbial organisms, to name a few. However, the above guidelines can be used as the basis for fine-tuning the treatment, e. g., determining the optimum dose of administration, which will require no more than routine experimentation consisting of monitoring the subject and adjusting the dosage. Remington: The Science and Practice of Pharmacy (Gennaro ed. 20.sup.th edition, Williams & Wilkins PA, USA) (2000).

IV. Advantages

Amtimicrobials (e.g. antibiotics) and antimicrobial-related compounds are often hydrophilic and are difficult to penetrate skin membrane barrier. When antimicrobials or antimicrobial-related compounds are taken orally, they may be inactivated by first pass metabolism. In the case of injection, administration of antimicrobials and amtimicrobial-related compounds is painful and may requires frequent and costly office visits.

In certain embodiments, since a HPP or HPC of the invention is capable of crossing one or more biological barriers, the HPP or HPC can be administered locally (e.g., topically or transdermally) to reach a location where a condition occurs without the necessity of a systematic administration (e.g., oral or parenteral administration). A local administration and penetration of a HPP or HPC allows the HPP or HPC to reach the same level of local concentration of an agent or drug with much less amount or dosage of HPP or HPC in comparison to a systematic administration of a parent agent or drug; alternatively, a higher level of local concentration which may not be afforded in the systematic administration, or if possible, requires significantly higher dosage of an agent in the systematic administration. The high local concentration of the HPP/HPC or its parent agent if being cleaved enables the treatment of a condition more effectively or much faster than a systematically delivered parent agent and the treatment of new conditions that may not be possible or observed before. The local administration of the HPP or HPC may allow a biological subject to reduce potential sufferings from a systemic administration, e.g., adverse reactions associated with the systematic exposure to the agent, gastrointestinal/renal effects. Additionally, the local administration may allow the HPP or HPC to cross a plurality of biological barriers and reach systematically through, for example, general circulation and thus avoid the needs for systematic administration (e.g., injection) and obviate the pain associated with the parenteral injection.

In certain embodiments, a HPP/HPC or a pharmaceutical composition according to the invention can be administered systematically (e.g., orally or parenterally). The HPP/HPC or the active agent (e.g., drug or metabolite) of the HPP/HPC may enter the general circulation with a faster rate than the parent agent and gain faster access to the action site a condition. Additionally, the HPP/HPC can cross a biological barrier (e.g., blood brain barrier and blood milk barrier) which has not been penetrated if a parent agent is administered alone and thus offer novel treatment of conditions that may not be possible or observed before.

For example, HPPs/HPCs of antimicrobials or antimicrobial-related compounds in the invention demonstrated high penetration rate through a biological barrier (e.g., >about 10 times, >about 50 times, >about 100 times, >about 200 times, >about 300 times, >about 1000 times higher than if the antimicrobials or antimicrobial-related compounds are administered alone). No or few adverse side effects were observed from the subjects that took antimicrobial HPP/HPC, while side effects (such as nausea) were observed from the subjects that took the parent antimicrobials at the similar dosage.

V. Examples

The following examples are provided to better illustrate the claimed invention and are not to be interpreted in any way as limiting the scope of the invention. All specific compositions, materials, and methods described below, in whole or in part, fall within the scope of the invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

Example 1. Preparation of a HPP from a Parent Drug

In certain embodiments, a parent compound having the following Structure F-C:

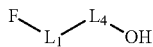

Structure F-C is converted to a HPP having Structure L-1:

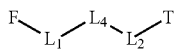

Structure L-1 including stereoisomers and pharmaceutically acceptable salts thereof, wherein:
F, L1, L2, and L4 are defined as supra;
T is a transportational unit of a HPP of an antimicrobial or antimicrobial-related compound. For example, T is selected from the group consisting of W and R6 as defined supra.

In certain embodiments of the invention, a HPP having Structure L-1 is prepared according to organic synthesis by reacting the parent compounds or derivatives of the parent compounds having Structure D (e.g. acid halides, mixed anhydrides of the parent compounds, etc.):

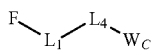

Structure D with compounds of Structure E (Scheme 1):

 Structure E wherein $W_C$ is selected from the group consisting of OH, halogen, alkoxycarbonyl and substituted aryloxycarbonyloxy; and
F, $L_1$, $L_2$, $L_4$ and T are defined as supra.

Scheme 1. Preparation of a HPP from a parent compound (I).

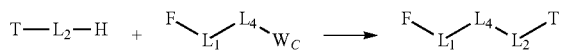

In certain embodiments, a HPP having Structure L-1 is prepared following Scheme 1 as described supra, wherein $L_4$ is C=O.

In certain embodiments, a parent compound having the following Structure F:

Structure F-N reacts with a compound having the following structure G:

Structure G to obtain a HPP of Structure L:

Structure L-1 including stereoisomers and pharmaceutically acceptable salts thereof, wherein:
F, L1, L2, and L4 are defined as supra;
T is a transportational unit of a HPP of an antimicrobial or antimicrobial-related compound. For example, T is selected from the group consisting of T is selected from the group consisting of W and $R_6$ as defined supra; and
$W_N$ is selected from the group consisting of OH, halogen, alkoxycarbonyl and substituted aryloxycarbonyloxy. (Scheme 2)

Scheme 2. Preparation of a HPP from a parent compound (II).

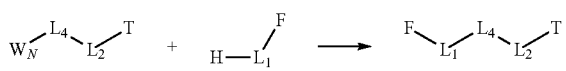

In certain embodiments, a HPP having a structure of Structure L-1 is prepared by organic synthesis wherein the unwanted reactive sites such as —C(=O)OH, —NH$_2$, —OH, or —SH are protected before linking a transportational unit with a functional unit according to one of the synthetic route as described supra. In certain embodiments, the obtained protected HPP may be further partially or completely deprotected to render a partially protected HPP or an unprotected HPP respectively.

Preparation of 6-phenoxyacetacetamidopenicillanic acid 2-diethylaminoethyl ester hydrochloride 39 g (0.1 mol) of Penicillin V potassium was dissolved in 100 ml of acetonitrile. 39 g (0.15 mol) of 2-Bromo-N,N-diethylethylamine. HBr in ethyl acetate was added into the reaction mixture. The mixture was stirred for 3 h at RT. Then 8 g of sodium bicarbonate was added into the reaction mixture. The mixture was stirred for another 2 h at RT. The solvents were evaporated off. 250 ml of ethyl acetate was added into the reaction mixture and the mixture was washed with water (3×100 ml). The organic solution was dried over anhydrous sodium sulfate. Sodium sulfate was removed by filtration. 3.5 g of HCl in 50 ml of ether was added into the reaction mixture with stirring. The solid product was collected by filtration. After drying, it yielded 38 g of the desired hygroscopic product (78.2%). Solubility in water: 50 mg/ml; elementary analysis: $C_{22}H_{32}ClN_3O_5S$; MW: 486.0. Calculated % C: 54.37; H: 6.64; N: 8.65; Cl: 7.29; O: 16.46; S: 6.60; Found % C: 54.32; H: 6.68; N: 8.61; Cl: 7.32; O: 16.51; S: 6.56.

Preparation of
6-(2,6-dimethoxybenzamido)penicillinic acid
2-diethylaminoethyl ester hydrochloride 38 g (0.1 mol) of 6-(2,6-dimethoxybenzamido)penicillinic acid was dissolved in 300 ml of chloroform. 0.6 g of N,N'-Dicyclohexylcarbodiimide was added into the reaction mixture. 1.7 g of N,N-dimethylaminoethanol and 2 g of 4-dimethylaminopyridine were added into the reaction mixture. The mixture was stirred for 10 hours at RT. The solid was removed by filtration. The chloroform solution was washed with 5% $NaHCO_3$ (2×100 ml) and water (3×100 ml). The organic solution was dried over anhydrous sodium sulfate. Sodium sulfate was removed by filtration. 3.5 g of HCl in 50 ml of ether was added into the reaction mixture with stirring. The solid product was collected by filtration. After drying, it yielded 40 g of the desired hygroscopic product (77.5%). Solubility in water: 50 mg/ml; elementary analysis: $C_{23}H_{34}ClN_3O_6S$; MW: 516.05. Calculated % C: 53.53; H: 6.64; N: 8.14; Cl: 6.87; O: 18.60; S: 6.21; Found % C: 53.49; H: 6.68; N: 8.11; Cl: 6.90; O: 18.64; S: 6.18.

Other HPPs of an antimicrobial or antimicrobial-related compound can be synthesized by similar procedure.

Example 2. HPPs of Antimicrobials and Antimicrobial-Related Compounds have Higher In Vitro Penetration Rates Across Human Skin Comparing to their Parent Drugs Penetration rates of HPPs and their parent drugs through human skin were measured in vitro by modified Franz cells. A Franz cell had two chambers, the top sample chamber and the bottom receiving chamber. The human skin tissue (360-400 μm thick) that separated the top and the receiving chambers was isolated from the anterior or posterior thigh areas.

Figure 1C:
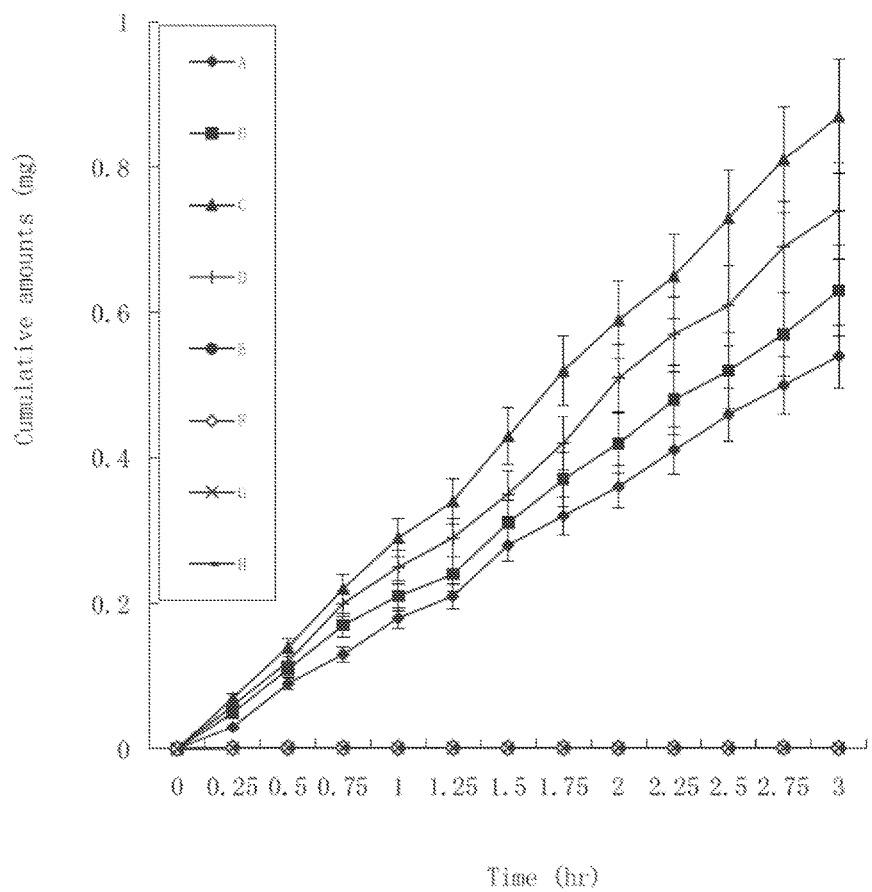
FIG. 1c: Cumulative amounts of 4-aminobenzenesulfonamide (sulfanilamide, E), 4-(4-dimethylaminobutyryl)amidobenzenesulfonamide.HCl salt (DMAB-sulfanilamide, A), 6-oxo-3-(2-[4-(N-pyridin-2-ylsulfamoyl)phenyl]hydrazono)cyclohexa-1,4-dienecarboxylic acid, 6-oxo-3-(2-[4-(N-pyridin-2-ylsulfamoyl)phenyl]hydrazono)cyclohexa-1,4-dienecarboxylic acid (sulfasalazine, F), 6-oxo-3-(2-[4-(N-pyridin-2-ylsulfamoyl)phenyl]hydrazono)cyclohexa-1,4-dienecarboxylic acid N,N-diethyaminopropyl ester.HCl salt (sulfasalazine-DEPE, B), 1-cyclopropyl-6-fluoro-4-oxo-7-piperazin-1-yl-quinoline-3-carboxylic acid (ciprofloxacin, G), 1-cyclopropyl-6-fluoro-4-oxo-7-piperazin-1-yl-quinoline-3-carboxylic acid butyl ester.HCl salt (ciprofloxacin-BE, C), 1-ethyl-7-methyl-4-oxo-[1,8]naphthyridine-3-carboxylic acid (nalidixic acid, H), 1-ethyl-7-methyl-4-oxo-[1,8]naphthyridine-3-carboxylic acid N,N-diethylaminoethyl ester.HCl salt (nalidixic acid-DEE, D), crossing isolated human skin tissue in Franz cells (n=5). In each case, the vehicle was pH 7.4 phosphate buffer (0.2 M).

A test compound (0.2 mL, 10% in 0.2 M phosphate buffer, pH 7.4) was added to the sample chamber of a Franz cell. The receiving chamber contained 2 ml of 2% bovine serum albumin in saline which was stirred at 600 rpm. The amount of the tested compound penetrating the skin was determined by high-performance liquid chromatography (HPLC) method. The results were shown in FIGS. 1a1, 1a2, 1a3, 1a4, 1b, and 1c. Apparent flux values of the tested compounds calculated from the slopes in the FIGS. 1a1, 1a2, 1a3 and 1a4 were summarized in Table 1a. Apparent flux values of the tested compounds calculated from the slopes in the FIGS. 1b and 1c are summarized in Tables 1b and 1c respectively.

Because the lowest detectable apparent flux values in this method was 1 μg/cm²/h, parent drugs that showed a apparent flux value equal to or less than 1 $\mu g/cm^2/h$ were considered as not detectable for penetrating across the skin tissue. For the parent compounds (e.g. penicillin V, penicillin O) which had apparent flux values <1 $\mu g/cm^2/h$, their HPPs had detectable apparent flux values. For the parent compounds which had apparent flux values >1 $\mu g/cm^2/h$, their HPPs had higher detectable apparent flux values. Therefore the HPPs of antimicrobials or antimicrobial-related compounds showed a higher penetration rate (340-600 times higher) across the skin tissue comparing to their parent compounds.

TABLE 1a

In vitro Penetration Rate of HPPs and their Parent Compounds (I)

| HPP Structure # | HPPs | mg/cm²/h | Parent compounds | mg/cm²/h |
|---|---|---|---|---|
| P-83 | 6-phenoxyacetacetamidopenicillanic acid 2-diethylaminoethyl ester hydrochloride | 0.72 ± 0.06 | penicillin V | <0.001 |
| P-84 | Allylmercaptomethylpenicillinic acid 2-dimethylaminoethyl ester hydrochloride | 0.65 ± 0.05 | penicillin O | <0.001 |
| P-11 | 6-(2,6-dimethoxybenzamido)penicillinic acid 2-dipropylaminoethyl ester hydrochloride | 0.52 ± 0.07 | Methicillin | <0.001 |
| P-2 | 6-(5-methyl-3-phenyl-2-isoxazoline-4-carboxamido)penicillinic acid 4-piperidineethyl ester hydrochloride | 0.77 ± 0.08 | Oxacillin | <0.001 |
| P-2 | 6-[3-(o-chlorophenyl)-5-methyl-4-isoxazolecarboxamido]penicillinic acid 3-piperidineethyl ester hydrochloride | 0.85 ± 0.05 | cloxacillin | <0.001 |
| P-2 | 6-[3-(2,6-dichlorophenyl)-5-methyl-4-isoxazolecarboxamido]penicillinic acid 1-piperidineethyl ester hydrochloride | 0.58 ± 0.05 | Dicloxacillin | <0.001 |
| P-3 | 6-[D(-)-α-aminophenylacetamidopenicillinic acid ethyl ester hydrochloride | 0.82 ± 0.06 | Ampicillin | <0.015 |
| P-7 | D-α-[(imidazolidin-2-on-1-yl)carbonylamino]benzylpenicillin 2-pyrrolidinemethyl ester hydrochloride | 0.72 ± 0.05 | Azlocillin | <0.001 |
| P-85 | 6R-[2-[3-(methylsulfonyl)-2-oxo-1-imidazolidinecarboxamido]-2-phenylacetamido]penicillinic acid 1-pyrrolidineethyl ester hydrochloride | 0.79 ± 0.07 | Mezlocillin | <0.001 |
| P-1 | 6-D(-)-α-(4-ethyl-2,3-dioxo-1-piperazinylcarbonylamino)-α-phenylacetamidopenicillinic acid 2-diethylaminoethyl ester hydrochloride | 0.74 ± 0.08 | piperacillin | <0.001 |

TABLE 1a-continued

In vitro Penetration Rate of HPPs and their Parent Compounds (I)

| HPP Structure # | HPPs | mg/cm²/h | Parent compounds | mg/cm²/h |
|---|---|---|---|---|
| P-19 | 7-(2-thienylacetamido)cephalosporanic acid 2-diethylaminoethyl ester hydrochloride | 0.62 ± 0.06 | Cephalothin | <0.001 |
| P-86 | 7-[(hydroxyphenylacetyl)amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride | 0.75 ± 0.05 | Cefamandole | <0.001 |
| P-26 | 3-[[(aminocarbonyl)oxy]methyl]-7-[[2-furanyl(methoxyimino)acetyl]amino]-8-oxo-5-thia-1-azabicyclo[4.2.0]oct-2-ene-2-carboxylic acid 2-diethylaminoethyl ester hydrochloride | 0.67 ± 0.04 | Cefuroxime | <0.001 |
| P-14 | 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride | 0.61 ± 0.05 | cefoxitin | <0.001 |
| P-62 | 7-[[[2-(acetylaminomethyl)phenyl]acetyl]amino]-3-[[[1-(ethoxylcarbonylmethyl)-1H-tetrazol-5-yl]thio]methyl]-8-oxo-5-thia-1-azabicyclo[4.2.0]oct-2-ene-2-carboxylic acid 2-diethylaminoethyl ester hydrochloride | 0.52 ± 0.04 | Ceforanide | <0.001 |
| P-20 | 7-[(acetylaminophenylacetyl)amino]-3-chloro-8-oxo-5-thia-1-azabicyclo[4.2.0]oct-2-ene-2-carboxylic acid 2-diethylaminoethyl ester hydrochloride | 0.71 ± 0.05 | Cefaclor | <0.016 |
| P-29 | 3-[(acetyloxy)methyl]-7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride | 0.73 ± 0.06 | Cefotaxime | <0.018 |
| P-28 | 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride | 0.62 ± 0.05 | Ceftizoxime | <0.010 |
| P-39 | 7-[[[[(4-ethyl-2,3-dioxo-1-piperazinyl)carbonyl]amino](4-acetoxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride | 0.57 ± 0.04 | Cefoperazone | <0.015 |
| P-46 | 7-[2-(2-acetylamino-4-thiazolyl)-2-((Z)-methoxyimino)acetamido]-3-(methoxymethyl)-8-oxo-5-thia-1-azabicyclo[4.2.0]oct-2-ene-2-carboxylic acid 2-diethylaminoethyl ester hydrochloride | 0.51 ± 0.03 | Cefpodoxime proxetil | <0.001 |
| P-45 | 7-[2-(2-acetylamino-4-thiazolyl)-2-((Z)-ethoxycarbonylmethoxy)imino]acetamido]-3-(vinyl)-8-oxo-5-thia-1-azabicyclo[4.2.0]oct-2-ene-2-carboxylic acid 2-diethylaminoethyl ester hydrochloride | 0.58 ± 0.05 | Cefixime | <0.010 |

TABLE 1b

In vitro Penetration Rate of HPPs of beta-lactamases inhibitors and their Parent Compounds (II)

| HPP Structure # | HPPs | mg/cm²/h | Parent compounds | mg/cm²/h |
|---|---|---|---|---|
| I-4 | [2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide 1-piperidineethyl ester•HCl salt (tazobactam-PEE), | 0.32 ± 0.03 | [2S-(2alpha,3beta,5alpha)]-3-Methyl-7-oxo-3-(1H-1,2,3-triazol-1-ylmethyl)-4-thia-1-azabicyclo[3.2.0]heptane-2-carboxylic acid 4,4-dioxide sodium salt (tazobactam) | <0.001 |
| I-3 | 2S,5R)-3,3-dimethyl-7-oxo-4-thia-1-azabicyclo[3.2.0]heptane-2-carboxylic acid 4,4-dioxide N,N-diethylaminoethyl ester•HCl salt (sulbactam-DEE), | 0.35 ± 0.03 | 2S,5R)-3,3-dimethyl-7-oxo-4-thia-1-azabicyclo[3.2.0]heptane-2-carboxylic acid 4,4-dioxide sodium (sulbactam), | <0.001 |
| I-2 | (2R,5R,Z)-3-(2-hydroxyethylidene)-7-oxo-4-oxa-1-aza-bicyclo[3.2.0]heptane-2-carboxylic acid 4-piperidineethyl ester•HCl salt (clavulanic acid-PEE) | 0.29 ± 0.02 | (2R,5R,Z)-3-(2-hydroxyethylidene)-7-oxo-4-oxa-1-aza-bicyclo[3.2.0]heptane-2-carboxylic acid (clavulanic acid) | <0.001 |
| I-9 | [(N-benzyloxycarbonylamino)methyl]-phosphonic acid (4-nitrophenyl)(N,N-diethylaminomethyl) ester•HCl salt | 0.37 ± 0.03 | [(N-benzyloxycarbonylamino)methyl]-phosphonic acid mono-(4-nitrophenyl) ester sodium salt | <0.001 |
| I-33 | [(N-benzyloxycarbonylamino)methyl]-phosphonic acid (3-pyridinyl)(1-piperidineethyl) ester•HCl salt | 0.25 ± 0.04 | [(N-benzyloxycarbonylamino)methyl]-phosphonic acid mono-(3-pyridinyl) ester sodium salt | <0.001 |

TABLE 1c

In vitro Penetration Rate of HPPs of sulfonamides, sulfones, quinolones and their Parent Compounds (III)

| HPP Structure | HPPs | mg/cm²/h | Parent compounds | mg/cm²/h |
|---|---|---|---|---|
| S-1 | 4-(4-dimethylaminobutyryl)amido-benzenesulfonamide•HCl salt(DMAB-sulfanilamide), | 0.18 ± 0.03 | 4-aminobenzene-sulfonamide(sulfanilamide), | <0.001 |
| S-9 | 6-oxo-3-(2-[4-(N-pyridin-2-ylsulfamoyl)phenyl]hydrazono)cyclohexa-1,4-dienecarboxylic acid N,N-diethyaminopropyl ester•HCl salt (sulfasalazine-DEPE), | 0.21 ± 0.03 | 6-oxo-3-(2-[4-(N-pyridin-2-ylsulfamoyl)phenyl]hydrazono)cyclohexa-1,4-dienecarboxylic acid(sulfasalazine) | <0.001 |
| T-15 | 1-cyclopropyl-6-fluoro-4-oxo-7-piperazin-1-yl-quinoline-3-carboxylic acid butyl ester•HCl salt(ciprofloxacin-BE), | 0.29 ± 0.02 | 1-cyclopropyl-6-fluoro-4-oxo-7-piperazin-1-yl-quinoline-3-carboxylic acid, | <0.001 |
| S-11 | 1-ethyl-7-methyl-4-oxo-[1,8]naphthyridine-3-carboxylic acid N,N-diethylaminoethyl ester•HCl salt(nalidixic acid-DEE), | 0.25 ± 0.04 | 1-ethyl-7-methyl-4-oxo-[1,8]naphthyridine-3-carboxylic acid(nalidixic acid), | <0.001 |

Example 3. In Vivo Penetration Rate of HPPs Through Skin and/or Blood-Brain Barrier In vivo rates of penetration of HPPs of beta-lactam antibiotics through skin and blood-brain barrier of intact hairless mice were studied. The donor consisted of a 20% solution of 6-(2,6-dimethoxybenzamido)penicillinic acid 2-diethylaminoethyl ester hydrochloride, 6-(5-methyl-3-phenyl-2-isoxazoline-4-carboxamido)penicillinic acid 2-diethylaminoethyl ester hydrochloride, 6-[3-(o-chlorophenyl)-5-methyl-4-isoxazolecarboxamido]penicillinic acid 2-diethylaminoethyl ester hydrochloride, methicillin, oxacillin, and cloxacillin in 1 mL of isopropanol were applied to a 10 cm² on the backs of hairless mice respectively. After 2 hours, the mice were killed. 5 ml of methanol was added to 1 g of homogenized blood, liver, kidney, muscle, or brain. The samples were centrifuged for 5 min and analyzed by HPLC (Table 2). No drug was detected for the mice treated with only the parent drug (methicillin, oxacillin, and cloxacillin). The results showed that these prodrugs have high pentration rate of blood-brain barrier while the respective parent drugs were not able to penetrate the skin.

TABLE 2

In vivo penetration results of HPPs of beta-lactam antibiotics

| | HPP | | |
|---|---|---|---|
| | 6-(2,6-dimethoxybenz-amido)penicillinic acid 2-diethylaminoethyl ester hydrochloride | 6-(5-methyl-3-phenyl-2-isoxazoline-4-carbox-amido)penicillinic acid 2-diethylaminoethyl ester hydrochloride | 6-[3-(o-chlorophenyl)-5-methyl-4-isoxazole-carbox-amido]penicillinic acid 2-diethylaminoethyl ester hydrochloride |
| parent drug | methicillin | oxacillin | cloxacillin |
| Amount of parent drug found in blood, liver, kidney, muscel and brain. | | | |
| Blood (µg/g) | 50 +/− 7 | 55 +/− 7 | 45 +/− 7 |
| Liver (µg/g) | 40 +/− 5 | 38 +/− 5 | 34 +/− 5 |
| Kidney (µg/g) | 35 +/− 5 | 36 +/− 5 | 32 +/− 5 |
| Muscel (µg/g) | 40 +/− 6 | 32 +/− 4 | 30 +/− 4 |
| Brain (µg/g) | 20 +/− 5 | 18 +/− 5 | 16 +/− 5 |

90 lactating dairy cows were recruited. 500 mg of 6-phenoxyacetacetamidopenicillanic acid 2-diethylaminoethyl ester hydrochloride (penicillin V-DEE), 6-(2,6-dimethoxybenzamido)penicillinic acid 2-diethylaminoethyl ester hydrochloride (methicillin-DEE), or 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride (ceftizoxime-DEE) in 10 ml of pH 7.4 phosphate buffer (0.2 M) was sprayed on the skin of udder twice per day. After 1 hours of topical application, milk samples were taken and analysized (Table 3). The amount of the parent drugs is, and. The results have shown that these prodrugs have very high penetration rate of blood-milk barrier. Their very high penetration rates of blood-milk or blood-brain barrier make them very valuable for treatment of brain, breast, prostate gland and other infections.

TABLE 3

In vivo penetration of HPP through blood-milk barrier

| HPP | Parent drug | Parent drug found in milk after topical application |
|---|---|---|
| penicillin V-DEE | penicillin V | 80 +/− 7 µg/g |
| methicillin-DEE | methicillin | 75 +/− 6 µg/g |
| ceftizoxime-DEE | ceftizoxime | 70 +/− 7 µg/g |

Example 4. HPPs of Antimicrobials or Antimicrobial-Related Compounds Penetrate Cell Wall of Bacteria Faster than that of their Parent Drugs 0.5 mmol of a test compound (6-phenoxyacetacetamidopenicillanic acid 1-piperidineethyl ester hydrochloride (penicillin V-PEE), penicillin V, 6-(2,6-dimethoxybenzamido)penicillinic acid 2-pyrrolidinemethyl ester hydrochloride (methicillin-PME), methicillin, 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride (ceftizoxime-DEE), or ceftizoxime) was added into 100 ml of E. coli suspension and stirred for 3 minutes. The mixture was centrifuged at 3000 rpm. The supernatant was discarded and the pellet was washed three times with pH 7.4 phosphate buffer. Acetonitril (100 ml) was added into the pellet and the mixture was heated to 60° C. for 2 minutes. The acetonitrile solution was collected and evaporated to dryness. The amount of test compound was determined using HPLC. The results were shown in Table 4.

TABLE 4

The amount of antibiotics and their HPPs entered cells of E. Coli.

| | penicillin | penicillin V-PEE | methicillin | methicillin-PME | ceftizoxime | ceftizoxime-DEE |
|---|---|---|---|---|---|---|
| Drug amount in cell (mmol/g wet cell) | 0.2 | 55 | 0.25 | 50 | 0.2 | 53 |

Example 5 Conversion of HPPs to their Parent Drugs

HPPs of antimicrobials or antimicrobial-related compounds converted to the parent antimicrobials or antimicrobial-related compounds quickly in good yield in human plasma.

A HPP of antimicrobial or antimicrobial-related compound (10 mg) was dissolved in 0.1 ml of 0.2M pH 7.4 phosphate buffer. 1 ml of human plasma, preheated to 37° C., was added into the mixture. The mixture was kept in a water bath at 37° C., and at every 2 min intervals 0.2 ml of samples were withdrawn and added to 0.4 ml of methanol to precipitate the plasma protein. The samples were centrifuged for 5 min and analyzed by HPLC. The results showed that most of the HPPs of antimicrobials or antimicrobial-related compounds were converted back to the parent antimicrobials or antimicrobial-related compounds (Table 5).

TABLE 5

Half life of HPPs in plasma

| HPP | Parent compounds | Half life (min) |
|---|---|---|
| 6-phenoxyacetacetamidopenicillanic acid 2-diethylaminoethyl ester hydrochloride | penicillin V | 8 +/− 1 |
| allylmercaptomethylpenicillinic acid 2-diethylaminoethyl ester hydrochloride | penicillin O | 8 +/− 1 |
| 6-(2,6-dimethoxybenzamido)penicillinic acid 2-diethylaminoethyl ester hydrochloride | Methicillin | 10 +/− 1 |
| 6-(5-methyl-3-phenyl-2-isoxazoline-4-carboxamido)penicillinic acid 2-diethylaminoethyl ester hydrochloride | Oxacillin | 12 +/− 1 |
| 6-[3-(o-chlorophenyl)-5-methyl-4-isoxazolecarboxamido]penicillinic acid 2-diethylaminoethyl ester hydrochloride | cloxacillin | 8 +/− 1 |
| 6-[3-(2,6-dichlorophenyl)-5-methyl-4-isoxazolecarboxamido]penicillinic acid 2-diethylaminoethyl ester hydrochloride | Dicloxacillin | 12 +/− 1 |
| 6-[D(−)-α-acetamidophenylacetamidopenicillinic acid 2-diethylaminoethyl ester hydrochloride | Ampicillin | 10 +/− 1 |
| D-α-[(imidazolidin-2-on-1-yl)carbonylamino]benzylpenicillin 2-diethylaminoethyl ester hydrochloride | Azlocillin | 9 +/− 1 |
| 6R-[2-[3-(methylsulfonyl)-2-oxo-1-imidazolidinecarboxamido]-2-phenylacetamido]penicillinic acid 2-diethylaminoethyl ester hydrochloride | Mezlocillin | 13 +/− 1 |
| 6-D(−)-α-(4-ethyl-2,3-dioxo-1-piperazinylcarbonylamino)-α-phenylacetamidopenicillinic acid 2-diethylaminoethyl ester hydrochloride | piperacillin | 15 +/− 1 |
| 7-(2-thienylacetamido)cephalosporanic acid 2-diethylaminoethyl ester hydrochloride | Cephalothin | 9 +/− 1 |
| 7-[(hydroxyphenylacetyl)amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride | Cefamandole | 10 +/− 1 |
| 3-[[(aminocarbonyl)oxy]methyl]-7-[[2-furanyl(methoxyimino)acetyl]amino]-8-oxo-5-thia-1-azabicyclo[4.2.0]oct-2-ene-2-carboxylic acid 2-diethylaminoethyl ester hydrochloride | Cefuroxime | 8 +/− 1 |
| 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride | cefoxitin | 7 +/− 1 |
| 7-[[[2-(acetylaminomethyl)phenyl]acetyl]amino]-3-[[[1-(ethoxylcarbonylmethyl)-1H-tetrazol-5-yl]thio]methyl]-8-oxo-5-thia-1-azabicyclo[4.2.0]oct-2-ene-2-carboxylic acid 2-diethylaminoethyl ester hydrochloride | Ceforanide | 9 +/− 1 |
| 7-[(acetylaminophenylacetyl)amino]-3-chloro-8-oxo-5-thia-1-azabicyclo[4.2.0]oct-2-ene-2-carboxylic acid 2-diethylaminoethyl ester hydrochloride | Cefaclor | 8 +/− 1 |
| 3-[(acetyloxy)methyl]-7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride | Cefotaxime | 10 +/− 1 |
| 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride | Ceftizoxime | 11 +/− 1 |
| 7-[[[[(4-ethyl-2,3-dioxo-1-piperazinyl)carbonyl]amino](4-acetoxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride | Cefoperazone | 12 +/− 1 |
| 7-[2-(2-acetylamino-4-thiazolyl)-2-((Z)-methoxyimino)acetamido]-3-(methoxymethyl)-8-oxo-5-thia-1-azabicyclo[4.2.0]oct-2-ene-2-carboxylic acid 2-diethylaminoethyl ester hydrochloride | Cefpodoxime proxetil | 8 +/− 1 |
| 7-[2-(2-acetylamino-4-thiazolyl)-2-((Z)-ethoxycarbonylmethoxy)imino]acetamido]-3-(vinyl)-8-oxo-5-thia-1-azabicyclo[4.2.0]oct-2-ene-2-carboxylic acid 2-diethylaminoethyl ester hydrochloride | Cefixime | 9 +/− 1 |

Example 6. Minimum Inhibitory Concentrations (MICs) of HPPs of Antimicrobials or Antimicrobial-Related Compounds Minimum inhibitory concentrations (MICs) of the antimicrobials and their pro-drugs were assessed according to Jennifer M. Andrews, Journal of Antimicrobial Chemotherapy 48, suppl. S1, 5-16 (2001). The results (Tables 6a-6c) showed that the HPPs of antimicrobials were able to overcome β-lactam resistance in methicillin-resistant *Staphylococcus aureus* (MRSA) according to Minimum inhibitory concentrations (MICS).

TABLE 6a

MICs (mg/L) of various antimicrobials and their pro-drugs to methicillin-resistant *Staphylococcus aureus* (MRSA)

| | Penicillin V | Penicillin V-PEE | Methicillin | Methicillin-PME | Ceftizoxime | Ceftizoxime-DEE |
|---|---|---|---|---|---|---|
| MIC (mg/L) | 3524 | 1 | 2157 | 10 | 2786 | 0.5 |

TABLE 6b

MICs (mg/L) of various antibiotics plus bata-lactamase inhibitors or their pro-drugs.

| Antibiotic | E. coli | K. pneumonlae | E. cloacae | B. fragilis |
|---|---|---|---|---|
| Ceftriaxone | 16 | 0.5 | 1 | 8 |
| ceftriaxone/tazobactam | 8/1 | 0.3/0.0375 | 0.3/0.0375 | 4/0.5 |
| Ceftriaxone/tazobactam-PEE | 2/0.25 | 0.05/0.00625 | 0.1/0.0125 | 1/0.125 |
| ampicillin | 6 | 0.3 | 5 | 68 |
| Ampicillin/sulbactam | 3/0.375 | 0.1/0.0125 | 3/0.375 | 30/3.75 |
| Ampicillin/sulbactam-DEE | 0.5/0.0625 | 0.01/0.00125 | 0.05/0.00625 | 5/0.625 |

TABLE 6c

MICs (mg/L) of sulfonamide and quinolones and their pro-drugs.

| Antibiotic | E. coli | S. aureus | E. faecalis |
|---|---|---|---|
| Sulfisoxazole | 16 | 64 | 55 |
| DMAB-acetylsulfisoxazole | 0.5 | 1 | 1 |
| Ciprofloxacin | 10 | 128 | 2 |
| ciprofloxacin-BE | 0.2 | 5 | 0.05 |
| nalidixic acid | 6 | 158 | 64 |
| nalidixic acid-DEE | 0.2 | 5 | 1 |

Example 7. Antifungal Activities of HPPs of Antimicrobials or Antimicrobial-Related Compounds Antifungal activities of 6-phenoxyacetacetamidopenicillanic acid 2-diethylaminoethyl ester hydrochloride (penicillin V-DEE), 6-(2,6-dimethoxybenzamido)penicillinic acid 2-diethylaminoethyl ester hydrochloride (methicillin-DEE), and 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride (ceftizoxime-DEE) were assessed according to Roether W. et al., Mykosen 27 (1), 14-28 (1984). The results were listed in Table 7 below.

TABLE 7

Minimum inhibitory concentration (mg/l) of some prodrugs of beta-lactam antibiotics towards fungi in vitro.

| Pathogens | Penicillin V-DEE | Methicillin-DEE | Ceftizoxime-DEE |
|---|---|---|---|
| *Aspergillus nidulans* | 3 | 8 | 4 |
| *Trichophyton mentagrophytes* | 12 | 22 | 9 |
| *Microsporum canis* | 2 | 8 | 2 |
| *Candida albicans* | 7 | 16 | 8 |
| *Aspergillus niger* | 3 | 9 | 4 |

TABLE 7-continued

Minimum inhibitory concentration (mg/l) of some prodrugs of beta-lactam antibiotics towards fungi in vitro.

| Pathogens | Penicillin V-DEE | Methicillin-DEE | Ceftizoxime-DEE |
|---|---|---|---|
| *Aspergillus tereus* | 2 | 12 | 4 |
| *Penicillium carylophilium* | 2 | 9 | 3 |
| *Fusarium oxisporum* | 3 | 8 | 5 |
| *Fusarium aquaductum* | 2 | 10 | 3 |
| *Aspergillus giganteus* | 3 | 9 | 5 |

Example 8. Treatment of Clinical Mastitis Using HPPs of Beta-Lactam Antibiotics or Related Compounds 90 lactating dairy cows were recruited. Bacteriological cure was considered to have been achieved if the samples taken from the affected quarter on day 17 and day 22 were free of the bacterial species isolated in the pretreatment sample. Clinical cure was defined as the disappearance of clinical signs of disease which were observed on day 1 before treatment, in other words by the return to normal feed intake, rectal temperature<39.0° C., good general condition, absence of udder edema, normal milk appearance, and normal milk yield.

500 mg of 6-phenoxyacetacetamidopenicillanic acid 2-diethylaminoethyl ester hydrochloride (penicillin V-DEE), 6-(2,6-dimethoxybenzamido)penicillinic acid 2-diethylaminoethyl ester hydrochloride (methicillin-DEE), or 7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester hydrochloride (ceftizoxime-DEE) in 10 ml of pH 7.4 phosphate buffer (0.2 M) was sprayed on the skin of udder twice per day. The results are shown in Tables 8a and 8b. The prodrugs have demonstrated very high Clinical cure rates and Bacteriological cure rates.

TABLE 8a

Clinical cure rates of the topical treatment of cow mastitis with the novel prodrugs of antibiotics

| Prodrugs | Number of Cows | Cure Rate (%) Day 3 | Day 8 | Day 15 | Day 22 |
|---|---|---|---|---|---|
| Penicillin V-DEE | 30 | 50 | 90 | 93 | 97 |
| Methicillin-DEE | 30 | 43 | 90 | 97 | 100 |
| Ceftizoxime-DEE | 30 | 53 | 93 | 99 | 100 |

TABLE 8b

Bacteriological cure rates (day 22) of the topical treatment of cow mastitis with the novel prodrugs of antibiotics

| Pathogens | HPP Penicillin V-DEE | Methicillin-DEE | Ceftizoxime-DEE |
|---|---|---|---|
| *Staphylococcus aureus* | | | |
| No of cows | 6 | 5 | 6 |
| No. cured (%) | 4 (67%) | 4 (80%) | 5 (83%) |
| *Streptococcus uberis* | | | |
| No of cows | 10 | 10 | 11 |
| No. cured (%) | 8 (80%) | 7 (70%) | 9 (82%) |
| *E. coli* | | | |
| No of cows | 8 | 10 | 8 |
| No. cured (%) | 7 (87.5%) | 8 (80%) | 7 (87.5%) |
| Coagulase-negative staphylococci | | | |
| No of cows | 9 | 7 | 8 |
| No. cured (%) | 7 (78%) | 6 (85.7%) | 7 (87.5%) |
| Enterobacteriaceae | | | |
| No of cows | 7 | 8 | 6 |
| No. cured (%) | 6 (85.7%) | 6 (75%) | 5 (83.3%) |

Example 9. Anti-*M. tuberculosis* Activity of the Pro-Drugs of Antimicrobial Drugs Six-week-old female mice (BALB/c mice) were infected with $2.21 \pm 0.15 \times 10^3$ CFU of *M. tuberculosis* H37Rv by an airborne route. 20 days later, the mean CFU in lungs was $8.23 \pm 0.27 \times 10^7$ CFU, then the treatments began. Group A was untreated group (n=20), group B was the treated group with isoniazid/moxifoxacin/pyrazinamide (0.18/0.22/1.2 mmol/kg, were given orally) for 45 days, group C was the treated group with isoniazid/moxifoxacin/pyrazinamide (0.18/0.22/1.2 mmol/kg, were given orally) for 90 days, group D was the treated group with N—(N-methyl-phenylalanyl)isoniazid (pro-isoniazid, made from N-methylphenylalanine and isoniazid, were given tansdermally)/1-cyclopropyl-7-[(1S,6S)-2,8-diazabicyclo[4.3.0]non-8-yl]-6-fluoro-8-methoxy-4-oxo-quinoline-3-carboxylic acid butyl ester(pro-moxifoxacin)/pyrazinoic acid N,N-diethylaminoethyl ester (pro-pyrazinoic acid, 0.18/0.22/1.2 mmol/kg, were given tansdermally) for 45 days, group E was the treated group with pro-isoniazid/pro-moxifoxacin/pro-pyrazinoic acid (0.18/0.22/1.2 mmol/kg, were given tansdermally) for 90 days, group F is the treated group with pro-isoniazid/pro-moxifoxacin/pro-pyrazinoic acid (0.06/0.07/0.4 mmol/kg, were given tansdermally) for 45 days, and group G was the treated group with pro-isoniazid/pro-moxifoxacin/pro-pyrazinoic acid (0.06/0.07/0.4 mmol/kg, were given tansdermally) for 90 days. After the treatment stopped, the mice were held for an additional 90 days without treatment and then sacrificed to determine the proportion with negative lung cultures indicating cure. The results showed that the pro-drugs were superior to their parent drugs and they can be used transdermally (Tables 9a and 9b).

TABLE 9a

Treatment regimens and results

| Treatment regimen | Mean lung CFU Before treatment | After 45 days of treatment | After 90 days of treatment |
|---|---|---|---|
| Untreated (A) | $8.23 \pm 0.27 \times 10^7$ | Died | Died |
| isoniazid/moxifoxacin/pyrazinamide 0.18/0.22/1.2 mmol/kg, orally (B) | | $3.23 \pm 0.35 \times 10^3$ | |
| isoniazid/moxifoxacin/pyrazinamide 0.18/0.22/1.2 mmol/kg, orally (C) | | | $10.23 \pm 1.55$ |
| Pro-isoniazid/pro-moxifoxacin/pro-pyrazinamide 0.18/0.22/1.2 mmol/kg, transdermally (D) | | $1.23 \pm 0.35$ | |
| Pro-isoniazid/pro-moxifoxacin/pro-pyrazinamide 0.18/0.22/1.2 mmol/kg, transdermally (E) | | | 0 |
| Pro-isoniazid/pro-moxifoxacin/pro-pyrazinamide 0.06/0.07/0.4 mmol/kg, transdermally (F) | | $4.23 \pm 0.55$ | |
| Pro-isoniazid/pro-moxifoxacin/pro-pyrazinamide, 0.06/0.07/0.4 mmol/kg, transdermally (G) | | | 0 |

TABLE 9b

Outcomes of test-of-cure assessments

| Treatment regimen | Proportion (%) of mice cured after treatment for | |
|---|---|---|
| | After 45 days of treatment | After 90 days of treatment |
| Untreated (A) | 0/20 (0) | 0/20 (0) |
| isoniazid/moxifoxacin/pyrazinamide 0.18/0.22/1.2 mmol/kg, orally (B) | 2/20 (10) | |
| isoniazid/moxifoxacin/pyrazinamide 0.18/0.22/1.2 mmol/kg, orally (C) | | 5/20 (25) |
| Pro-isoniazid/pro-moxifoxacin/pro-pyrazinamide 0.18/0.22/1.2 mmol/kg, transdermally(D) | 18/20 (90) | |
| Pro-isoniazid/pro-moxifoxacin/pro-pyrazinamide 0.18/0.22/1.2 mmol/kg, transdermally (E) | | 20/20 (100) |
| Pro-isoniazid/pro-moxifoxacin/pro-pyrazinamide 0.06/0.07/0.4 mmol/kg, transdermally (F) | 10/20 (50) | |
| Pro-isoniazid/pro-moxifoxacin/pro-pyrazinamide, 0.06/0.07/0.4 mmol/kg, transdermally (G) | | 20/20 (100) |

Example 10. Treatment of Tuberculosis in Adults (Reduced Dosage for Child)

40 mg of N—(N-methyl-phenylalanyl)isoniazid (pro-isoniazid)/50 mg of 1-cyclopropyl-7-[(1S,6S)-2,8-diazabicyclo[4.3.0]non-8-yl]-6-fluoro-8-methoxy-4-oxo-quinoline-3-carboxylic acid butyl ester(pro-moxifoxacin)/40 mg of pyrazinoic acid N,N-diethylaminoethyl ester (pro-pyrazinoic acid) in 3 ml of water is applied to the skin of chest or any other skin of the patient's body (near the infected organs) every morning and evening (twice per day) for 90 days or until the disease-free.

Example 11. Treatment of Leprosy or Hansen's Disease (HD) in Adults (Reduced Dosage for Child)

30 mg of 4-dimethylaminobutyrylamidophenyl-4'-aminophenylsulfone (pro-dapsone)/50 mg of 1-cyclopropyl-7-[(1S,6S)-2,8-diazabicyclo [4.3.0]non-8-yl]-6-fluoro-8-methoxy-4-oxo-quinoline-3-carboxylic acid butyl ester(pro-moxifoxacin)/15 mg of 2(4-dimethylaminobutyrylthiobenzimidazole in 3 ml of water is applied to the skin near the infected organs of the patient's body every morning and evening (twice per day) for 6 months or until the disease-free.

Example 12. Treatment of Ear Infection 10 mg of 6-phenoxyacetacetamidopenicillanic acid 2-diethylaminoethyl ester hydrochloride in 1 ml of water is applied to the skin near the infected ears of the patient every morning and evening (twice per day) for 2 weeks or until the disease-free.

Example 13. Treatment of Lower Respiratory Tract Infection in Adults (Reduced Dosage for Child)

50 mg of D-α-[(imidazolidin-2-on-1-yl)carbonylamino]benzylpenicillin 2-pyrrolidinemethyl ester hydrochloride in 3 ml of water is applied to the skin near the neck and/or chest of the patient every morning and evening (twice per day) for 2 weeks or until the disease-free.

Example 14. Treatment of Upper Respiratory Tract Infection in Adults (Reduced Dosage for Child)

30 mg of 6-DH-α-(4-ethyl-2,3-dioxo-1-piperazinylcarbonylamino)-α-phenylacetamidopenicillinic acid 2-diethylaminoethyl ester hydrochloride in 2 ml of water is applied to the skin near the neck of the patient every morning and evening (twice per day) for 2 weeks or until the disease-free.

Example 15. Treatment of Upper Respiratory Tract Infection in Adults (Reduced Dosage for Child)

30 mg of 3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester hydrochloride in 2 ml of water is spayed into the mouth or nose of the patient every morning and evening (twice per day) for 2 weeks or until the disease-free Example 16. Treatment of Meningitis in Adults (Reduced Dosage for Child)

80 mg of 6-DH-α-(4-ethyl-2,3-dioxo-1-piperazinylcarbonylamino)-α-phenylacetamidopenicillinic acid 2-diethylaminoethyl ester hydrochloride in 3 ml of water is applied to the skin near the neck and head of the patient every morning and evening (twice per day) for 2 weeks or until the disease-free.

Example 17. Treatment of Diarrheal Diseases (Reduced Dosage for Child)

80 mg of 7-(2-thienylacetamido)cephalosporanic acid 2-diethylaminoethyl ester hydrochloride in 3 ml of water is applied to the skin near the navel of the patient every morning and evening (twice per day) for 2 weeks or until the disease-free.

Example 18. Treatment of Breast Infection 30 mg of 7-[(hydroxyphenylacetyl)amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester hydrochloride in 2 ml of water is applied to the skin near the breast of the patient every morning and evening (twice per day) for 2 weeks or until the disease-free.

Example 19. Treatment of Male or Female Reproductive System Infection (Reduced Dosage for Child)

50 mg of 3-[[(aminocarbonyl)oxy]methyl]-7-[[2-furanyl(methoxyimino)acetyl]amino]-8-oxo-5-thia-1-azabicyclo[4.2.0]oct-2-ene-2-carboxylic acid 2-diethylaminoethyl ester hydrochloride in 3 ml of water is applied to the skin near the pubic area of the patient every morning and evening (twice per day) for 2 weeks or until the disease-free.

What is claimed is:
1. A method for treating a bacteria-related condition in a biological subject, comprising transdermally administering to the biological subject a compound, wherein the compound is selected from:

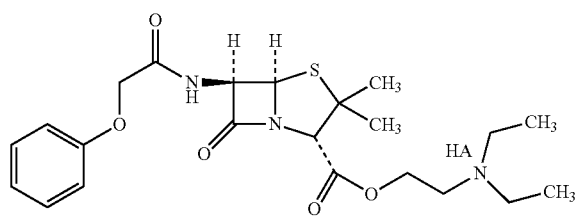

6-phenoxyacetacetamidopenicillanic acid 2-diethylaminoethyl ester•HA;

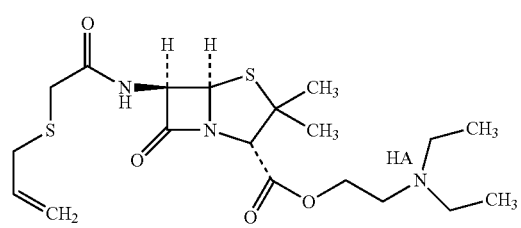

allylmercaptomethylpenicillinic acid 2-diethylaminoethyl ester•HA;

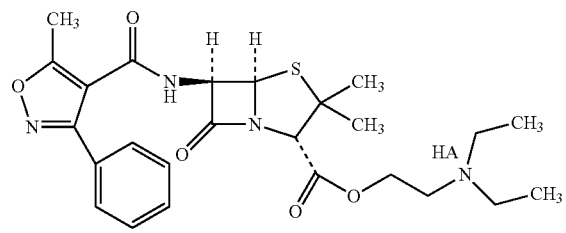

6-(5-methyl-3-phenyl-2-isoxazoline-4-carboxamido) penicillinic acid 2-diethylaminoethyl ester•HA;

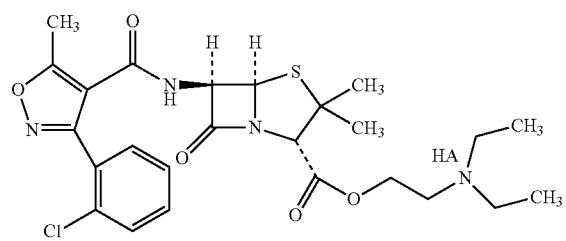

6-[3-(o-chlorophenyl)-5-methyl-4-isoxazolecarbox-amido]penicillinic acid 2-diethylaminoethyl ester•HA;

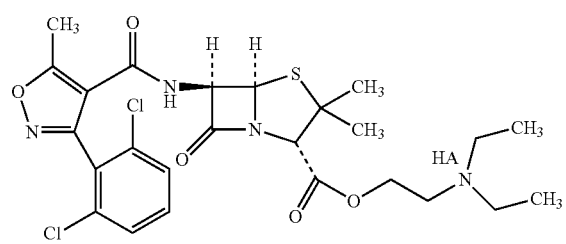

6-[3-(2,6-dichlorophenyl)-5-methyl-4-isoxazolecarbox-amido]penicillinic acid 2-diethylaminoethyl ester•HA;

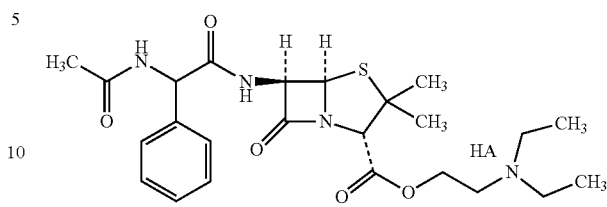

6-D(−)-α-acetamidophenylacetamidopenicillinic acid 2-diethylaminoethyl ester•HA;

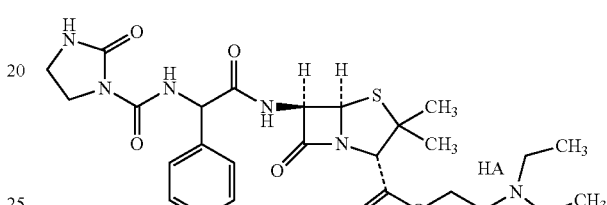

D-α-[(imidazolidin-2-on-1-yl)carbonylamino]ben-zylpenicillin 2-diethylaminoethyl ester•HA;

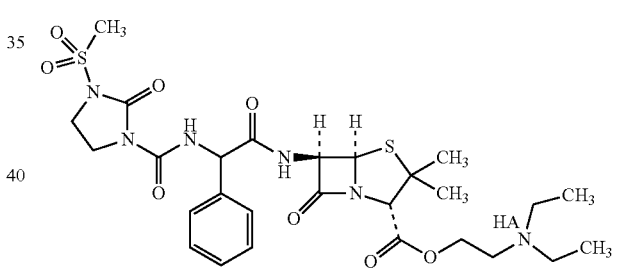

6R-[2-[3-(methylsulfonyl)-2-oxo-1-imidazolidinecarbox-amido]-2-phenylacetamido]penicillinic acid 2-diethyl-aminoethyl ester•HA;

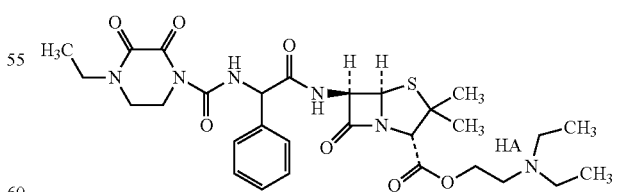

6-D(−)-α-(4-ethyl-2,3-dioxo-1-piperazinylcarbo-nylamino)-α-phenylacetamidopenicillinic acid 2-diethylaminoethyl ester•HA;

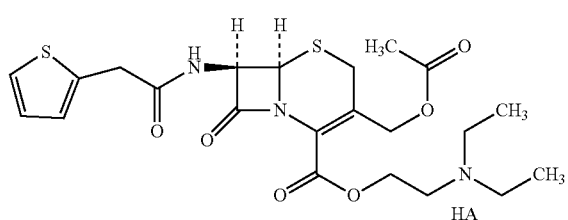

7-(2-thienylacetamido)cephalosporanic acid 2-diethylaminoethyl ester•HA;

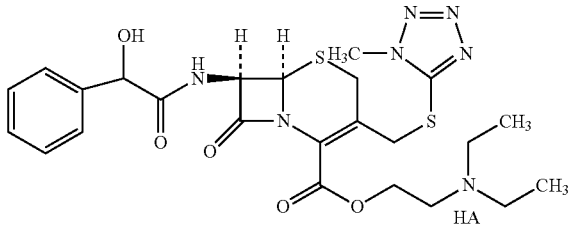

7-[(hydroxyphenylacetyl)amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester•HA;

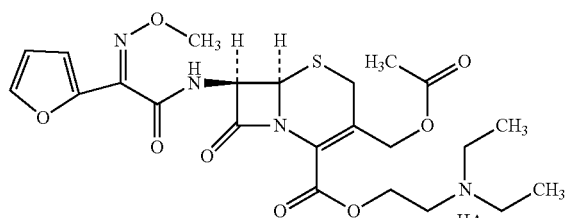

3-[[(aminocarbonyl)oxy]methyl]-7-[[2-furanyl(methoxyimino)acetyl]amino]-8-oxo-5-thia-1-azabicyclo[4.2.0]oct-2-ene-2-carboxylic acid 2-diethylaminoethyl ester•HA;

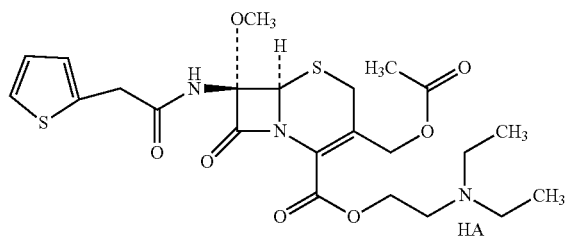

3-[[(aminocarbonyl)oxy]methyl]-7-methoxy-8-oxo-7-[(2-thienylacetyl)amino]-5-thia-1-azabicyclo[4.2.0]oct-2-ene-2-carboxylic acid 2-diethylaminoethyl ester•HA;

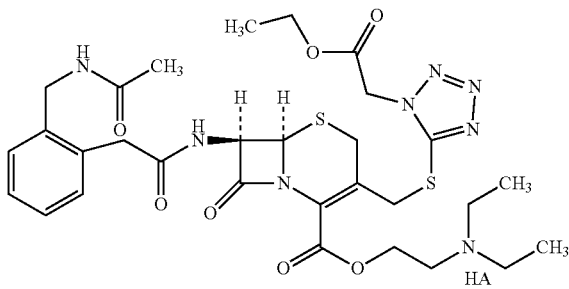

7-[[[2-(acetylaminomethyl)phenyl]acetyl]amino]-3-[[[1-(ethoxylcarbonylmethyl)-1H-tetrazol-5-yl]thio]methyl]-8-oxo-5-thia-1-azabicyclo[4.2.0]oct-2-ene-2-carboxylic acid 2-diethylaminoethyl ester•HA;

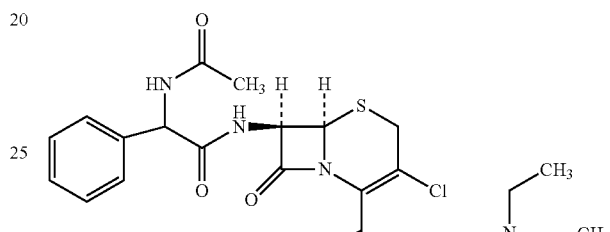

7-[(acetylaminophenylacetyl)amino]-3-chloro-8-oxo-5-thia-1-azabicyclo[4.2.0]oct-2-ene-2-carboxylic acid 2-diethylaminoethyl ester•HA;

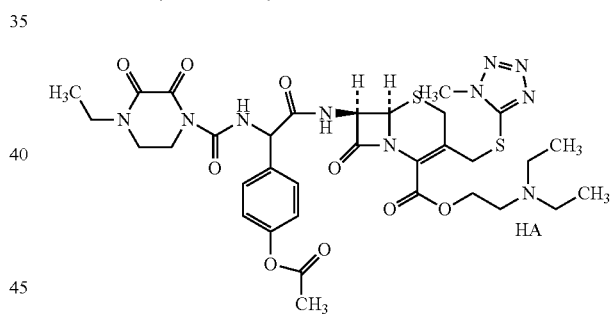

7-[[[[(4-ethyl-2,3-dioxo-1-piperazinyl)carbonyl]amino](4-acetoxyphenyl)acetyl]amino]-3-[[(1-methyl-1H-tetrazol-5-yl)thio]methyl]-8-oxo-5-thia-1-azabicyclo[4.2.0]oct-2-ene-2-carboxylic acid 2-diethylaminoethyl ester•HA;

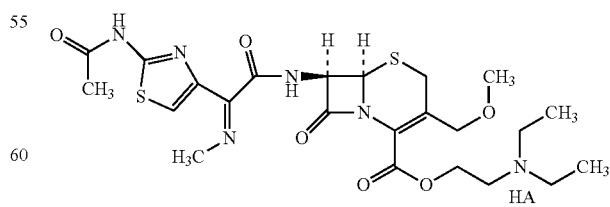

7-[2-(2-acetylamino-4-thiazolyl)-2-((Z)-methoxyimino)acetamido]-3-(methoxymethyl)-8-oxo-5-thia-1-azabicyclo[4.2.0]oct-2-ene-2-carboxylic acid 2-diethylaminoethyl ester•HA; and

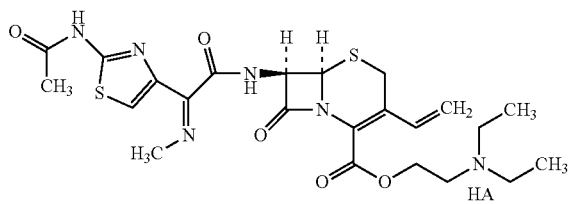

7-[[2-(2-acetylamino-4-thiazolyl)-2-((Z)-ethoxycarbonylmethoxy)imino]acetamido]-3-(vinyl)-8-oxo-5-thia-1-azabicyclo[4.2.0]oct-2-ene-2-carboxylic acid 2-diethylaminoethyl ester•HA, wherein HA is selected from nothing, hydrochloric acid, hydrobromic acid, hydroiodic acid, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, and pamoic acid.

2. The method according to claim 1, wherein the bacteria-related condition is an infection.

3. The method of claim 2, wherein the infection is selected from a liver infection, a stomach infection, a brain infection, a kidney infection, a heart infection, an ear infection, an eye infection, a nose infection, a mouth infection, a tongue infection, a colon infection, a pancreas infection, a gallbladder infection, a duodenum infection, a rectum stomach infection, a colonrectum infection, an intestine infection, a vein infection, a respiratory system infection, a vascular infection, an anorectum and pruritus ani infection, a urinary tract infection, a nosocomial infection, a *pseudomonas* infection, a coagulase-positive staphylococcal infection, a skin infection, toxinosis, acute infective endocarditis, a septicemia infection, necrotizing pneumonia, an infection of an implanted prosthesis, and an opportunistic infection with septicemia and pneumonia.

4. The method of claim 3, wherein the respiratory system infection is a lung infection.

5. The method of claim 1, wherein the bacteria-related condition is selected from plague, anthrax, lyme disease, brucellosis, whooping cough, acute enteritis, psittacosis, nongonococcal urethritis, trachoma, inclusion conjunctivitis of the newborn, lymphogranuloma venereum, pseudomembranous colitis, gas gangrene, food poisoning, anaerobic cellulitis, diphtheria, diarrhea, meningitis in infants, hemorrhagic colitis, hemolytic-uremic syndrome, tularemia, pneumonia, bronchitis, peptic ulcer, legionnaire's disease, Pontiac fever, leptospirosis, listeriosis, leprosy, tuberculosis, *mycoplasma* pneumonia, gonorrhea, ophthalmia neonatorum, septic arthritis, meningococcal disease, waterhouse-friderichsen syndrome, Rocky mountain spotted fever, typhoid fever type *salmonellosis, salmonellosis* with gastroenteritis and enterocolitis, bacillary dysentery/shigellosis, cystitis, meningitis and septicemia, endometritis, otitis media, sinusitis, syphilis, necrotizing fasciitis, streptococcal pharyngitis, scarlet fever, rheumatic fever, impetigo, erysipelas, puerperal fever, and cholera.

6. A method for treating a bacteria-related condition in a biological subject, comprising transdermally administering to the biological subject a compound which is:

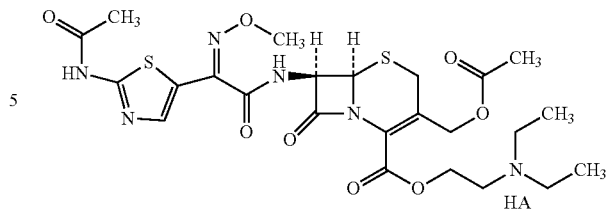

3-[(acetyloxy)methyl]-7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester•HA;

or

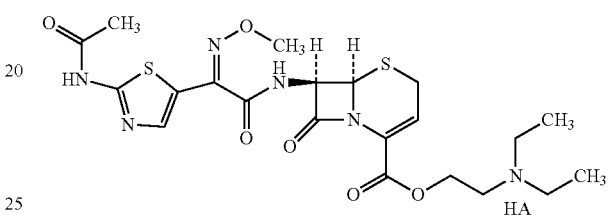

7-[[(2-acetylamino-4-thiazolyl)(methoxyimino)acetyl]amino]-8-oxo-5-thia-1-azabicyclo[4.2.0]oct-2-ene-2-carboxylic acid 2-diethylaminoethyl ester•HA;

wherein HA is selected from nothing, hydrochloric acid, hydrobromic acid, hydroiodic acid, nitric acid, sulfic acid, bisulfic acid, phosphoric acid, phosphorous acid, phosphonic acid, isonicotinic acid, acetic acid, lactic acid, salicylic acid, citric acid, tartaric acid, pantothenic acid, bitartaric acid, ascorbic acid, succinic acid, maleic acid, gentisinic acid, fumaric acid, gluconic acid, glucaronic acid, saccharic acid, formic acid, benzoic acid, glutamic acid, methanesulfonic acid, ethanesulfonic acid, benzensulfonic acid, p-toluenesulfonic acid, and pamoic acid.

7. The method according to claim 6, wherein the bacteria-related condition is an infection.

8. The method of claim 7, wherein the infection is selected from a liver infection, a stomach infection, a brain infection, a kidney infection, a heart infection, an ear infection, an eye infection, a nose infection, a mouth infection, a tongue infection, a colon infection, a pancreas infection, a gallbladder infection, a duodenum infection, a rectum stomach infection, a colonrectum infection, an intestine infection, a vein infection, a respiratory system infection, a vascular infection, an anorectum and pruritus ani infection, a urinary tract infection, a nosocomial infection, a *pseudomonas* infection, a coagulase-positive staphylococcal infection, a skin infection, toxinosis, acute infective endocarditis, a septicemia infection, necrotizing pneumonia, an infection of an implanted prosthesis, and an opportunistic infection with septicemia and pneumonia.

9. The method of claim 8, wherein the respiratory system infection is a lung infection.

10. The method according to claim 6, comprising transdermally administering to the biological subject a pharmaceutical composition comprising the compound and a pharmaceutically acceptable carrier.

11. The method according to claim 10, wherein the pharmaceutically acceptable carrier is polar.

12. The method according to claim 11, wherein the pharmaceutically acceptable carrier is selected from the group of alcohol, acetone, ester, water, and aqueous solution.

13. The method of claim 6, wherein the bacteria-related condition is selected from plague, anthrax, lyme disease, brucellosis, whooping cough, acute enteritis, psittacosis, nongonococcal urethritis, trachoma, inclusion conjunctivitis of the newborn, lymphogranuloma venereum, pseudomembranous colitis, gas gangrene, food poisoning, anaerobic cellulitis, diphtheria, diarrhea, meningitis in infants, hemorrhagic colitis, hemolytic-uremic syndrome, tularemia, pneumonia, bronchitis, peptic ulcer, legionnaire's disease, Pontiac fever, leptospirosis, listeriosis, leprosy, tuberculosis, *mycoplasma* pneumonia, gonorrhea, ophthalmia neonatorum, septic arthritis, meningococcal disease, waterhouse-friderichsen syndrome, Rocky mountain spotted fever, typhoid fever type *salmonellosis, salmonellosis* with gastroenteritis and enterocolitis, bacillary dysentery/shigellosis, cystitis, meningitis and septicemia, endometritis, otitis media, sinusitis, syphilis, necrotizing fasciitis, streptococcal pharyngitis, scarlet fever, rheumatic fever, impetigo, erysipelas, puerperal fever, and cholera.

\* \* \* \* \*